United States Patent
Niyikiza et al.

(10) Patent No.: US 12,161,757 B2
(45) Date of Patent: Dec. 10, 2024

(54) PLATINUM COMPLEXES AND USES THEREOF

(71) Applicant: L.E.A.F. HOLDINGS GROUP LLC, Gulph Mills, PA (US)

(72) Inventors: Clet Niyikiza, Gulph Mills, PA (US); Victor M. Moyo, Ringoes, NJ (US)

(73) Assignee: L.E.A.F. HOLDINGS GROUP LLC, Gulph Mills, PA (US)

( * ) Notice: Subject to any disclaimer, the term of this patent is extended or adjusted under 35 U.S.C. 154(b) by 133 days.

(21) Appl. No.: 17/307,441

(22) Filed: May 4, 2021

(65) Prior Publication Data
US 2021/0259970 A1   Aug. 26, 2021

Related U.S. Application Data

(63) Continuation of application No. 16/185,003, filed on Nov. 8, 2018, now abandoned.
(60) Provisional application No. 62/583,432, filed on Nov. 8, 2017.

(51) Int. Cl.
| | | |
|---|---|---|
| A61K 9/127 | (2006.01) | |
| A61K 31/555 | (2006.01) | |
| A61K 33/243 | (2019.01) | |
| A61K 47/26 | (2006.01) | |
| A61K 47/40 | (2006.01) | |
| A61K 47/42 | (2017.01) | |
| A61K 47/64 | (2017.01) | |
| A61K 47/68 | (2017.01) | |
| A61K 47/69 | (2017.01) | |
| A61P 35/00 | (2006.01) | |

(52) U.S. Cl.
CPC .......... *A61K 9/1271* (2013.01); *A61K 31/555* (2013.01); *A61K 33/243* (2019.01); *A61K 47/26* (2013.01); *A61K 47/40* (2013.01); *A61K 47/42* (2013.01); *A61K 47/645* (2017.08); *A61K 47/6849* (2017.08); *A61K 47/6911* (2017.08); *A61K 47/6951* (2017.08); *A61P 35/00* (2018.01)

(58) Field of Classification Search
CPC .. A61K 9/1271; A61K 31/555; A61K 33/243; A61K 47/26; A61K 47/40; A61K 47/42; A61K 47/645; A61K 47/6803; A61K 47/6849; A61K 47/6911; A61K 47/6951; A61P 35/00
See application file for complete search history.

(56) References Cited

U.S. PATENT DOCUMENTS

| | | | |
|---|---|---|---|
| 9,968,583 B2 * | 5/2018 | Kikuchi | A61K 31/337 |
| 10,266,609 B2 * | 4/2019 | Siedlecki | C07H 3/06 |
| 2001/0038830 A1 * | 11/2001 | Stewart | A61P 35/04 |
| | | | 556/136 |

OTHER PUBLICATIONS

Philippova et al Swiss Med Wkly, 144:w14037, pp. 1-10, 2014.*
Bochkov et al, Antioxidants and Redox Signaling, 12 (8), p. 1009, 2010.*
O'Shannessey et al (Oncotarget, 2(12), pp. 1227-1243, 2011.*

* cited by examiner

*Primary Examiner* — Gollamudi S Kishore
(74) *Attorney, Agent, or Firm* — Nixon & Vanderhye, PC

(57) ABSTRACT

The disclosure generally relates to compositions comprising therapeutic agent complexes and to methods of making and using the compositions. In particular embodiments, the disclosure provides compositions comprising platinum-based drug complexes and to methods of making and using these compositions.

30 Claims, 3 Drawing Sheets
Specification includes a Sequence Listing.

FIG. 1

Example L-gamma- polyglutamated antifolates
- PMX-[L-glutamyl]$_n$
- MTX-[L-glutamyl]$_n$
- LTX-[L-glutamyl]$_n$
- RTX-[L-glutamyl]$_n$
- piritrexim-[L-glutamyl]$_n$
- pralatrexate-[L-glutamyl]$_n$
- AG2034-[L-glutamyl]$_n$
- GW1843-[L-glutamyl]$_n$
- aminopterin-[L-glutamyl]$_n$
- LY309887-[L-glutamyl]$_n$

Wherein: the L-glutamyl groups are in gamma linkage (linked by their gamma carboxyl groups) and n = 4, 5, 2-10, 4-6, or >5

FIG. 2

Exemplary polyglutamated antifolates
- PMX-[glutamyl]$_n$
- MTX-[glutamyl]$_n$
- LTX-[glutamyl]$_n$
- RTX-[glutamyl]$_n$
- piritrexim-[glutamyl]$_n$
- pralatrexate-[glutamyl]$_n$
- AG2034-[glutamyl]$_n$
- GW1843-[glutamyl]$_n$
- aminopterin-[glutamyl]$_n$
- LY309887-[glutamyl]$_n$

Wherein:
each glutamyl (even in the same molecule) can be independently D-gamma-glutamic acid, L-alpha glutamic acid, or D-alpha glutamic
n = 4, 5, 2-10, 4-6, or >5

FIG. 3A
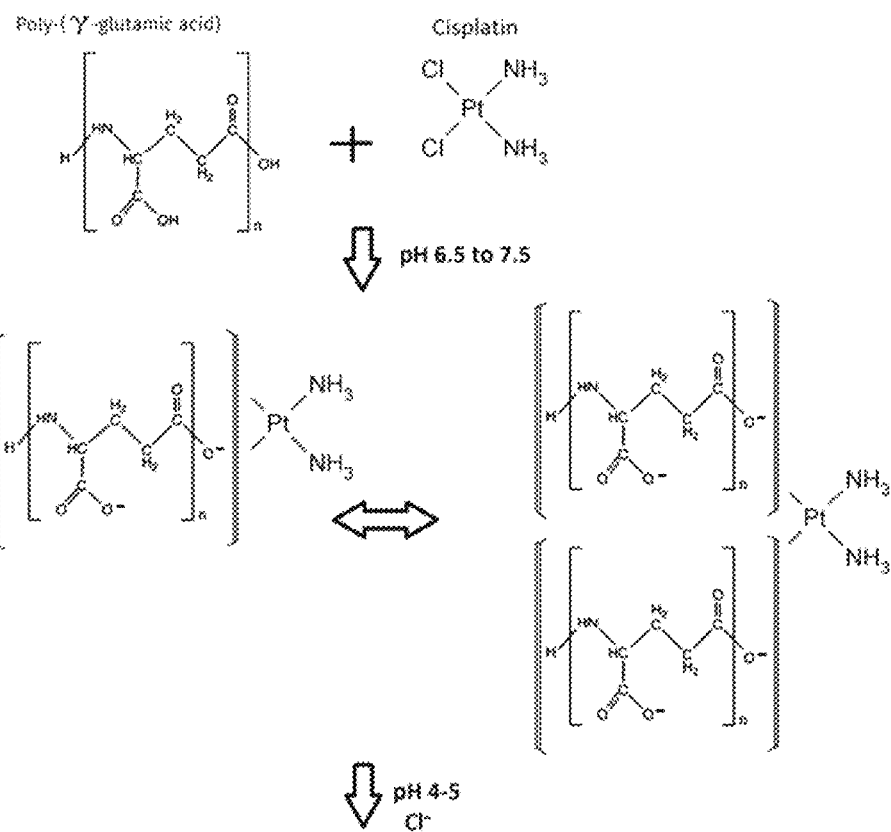
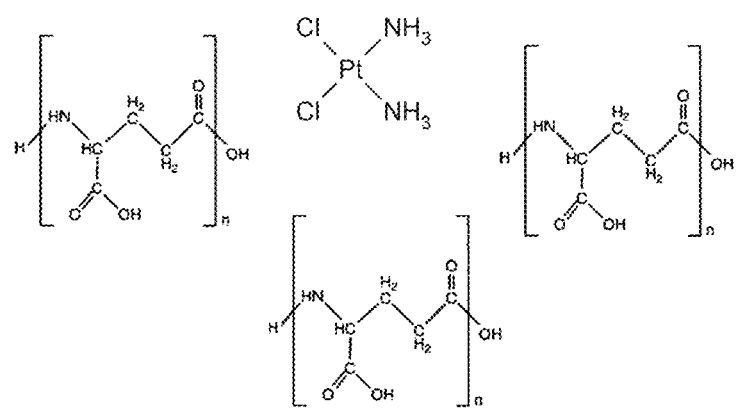

SEQUENCE LISTING

```
<160> NUMBER OF SEQ ID NOS: 44

<210> SEQ ID NO 1
<211> LENGTH: 25
<212> TYPE: PRT
<213> ORGANISM: Artificial Sequence
<220> FEATURE:
<223> OTHER INFORMATION: synthetic construct

<400> SEQUENCE: 1

Arg Gln Ile Lys Ile Trp Phe Gln Asn Arg Arg Met Lys Trp Lys Lys
1               5                   10                  15

Arg Lys Lys Arg Arg Gln Arg Arg Arg
            20                  25
```

```
<210> SEQ ID NO 2
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (6)..(6)
<223> OTHER INFORMATION: Xaa can be any naturally occurring amino acid

<400> SEQUENCE: 2

Arg Lys Lys Arg Arg Xaa Arg Arg Arg Gly Cys
1               5                   10

<210> SEQ ID NO 3
<211> LENGTH: 13
<212> TYPE: DNA
<213> ORGANISM: Artificial Sequence
<220> FEATURE:
<223> OTHER INFORMATION: synthetic construct

<400> SEQUENCE: 3
ccgccaagaa gcg                                                          13

<210> SEQ ID NO 4
<211> LENGTH: 100
<212> TYPE: DNA
<213> ORGANISM: Artificial Sequence
<220> FEATURE:
<223> OTHER INFORMATION: synthetic construct

<400> SEQUENCE: 4
gcgtgcacac gcgcgtagac ttcccccgca agtcactcgt tagcccgcca agaagcgacc       60
cctccggggc gagctgagcg gcgtggcgcg ggggcgtcat                            100

<210> SEQ ID NO 5
<211> LENGTH: 101
<212> TYPE: DNA
<213> ORGANISM: Artificial Sequence
<220> FEATURE:
<223> OTHER INFORMATION: synthetic construct

<400> SEQUENCE: 5
acgtgcatac gcacgtagac attccccgct tcccactcca aagtccgcca agaagcgtat       60
cccgctgagc ggcgtggcgc gggggcgtca tccgtcagct c                         101

<210> SEQ ID NO 6
<211> LENGTH: 58
<212> TYPE: DNA
<213> ORGANISM: Artificial Sequence
<220> FEATURE:
<223> OTHER INFORMATION: synthetic construct

<400> SEQUENCE: 6
acttcccccg caagtcactc gttagcccgc caagaagcga ccctccgggg cgagctg         58

<210> SEQ ID NO 7
<211> LENGTH: 9
<212> TYPE: PRT
<213> ORGANISM: Artificial Sequence
<220> FEATURE:
<223> OTHER INFORMATION: synthetic construct

<400> SEQUENCE: 7

Arg Lys Lys Arg Arg Gln Arg Arg Arg
```

```
<210> SEQ ID NO 8
<211> LENGTH: 13
<212> TYPE: PRT
<213> ORGANISM: Artificial Sequence
<220> FEATURE:
<223> OTHER INFORMATION: synthetic construct

<400> SEQUENCE: 8

Gly Arg Lys Lys Arg Arg Gln Arg Arg Arg Thr Pro Gln
1               5                   10

<210> SEQ ID NO 9
<211> LENGTH: 11
<212> TYPE: PRT
<213> ORGANISM: Artificial Sequence
<220> FEATURE:
<223> OTHER INFORMATION: synthetic construct

<400> SEQUENCE: 9

Tyr Gly Arg Lys Lys Arg Arg Gln Arg Arg Arg
1               5                   10

<210> SEQ ID NO 10
<211> LENGTH: 15
<212> TYPE: PRT
<213> ORGANISM: Artificial Sequence
<220> FEATURE:
<223> OTHER INFORMATION: synthetic construct

<400> SEQUENCE: 10

Ala Ala Val Ala Leu Leu Pro Ala Val Leu Leu Ala Leu Leu Ala
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: synthetic construct

<400> SEQUENCE: 11

Met Gly Leu Gly Leu His Leu Leu Val Leu Ala Ala Ala Leu Gln
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: synthetic construct

<400> SEQUENCE: 12

Gly Ala Leu Phe Leu Gly Phe Leu Gly Ala Ala Gly Ser Thr Met
1               5                   10                  15

<210> SEQ ID NO 13
<211> LENGTH: 21
<212> TYPE: PRT
<213> ORGANISM: Artificial Sequence
<220> FEATURE:
<223> OTHER INFORMATION: synthetic construct

<400> SEQUENCE: 13

Ala Gly Tyr Leu Leu Gly Lys Ile Asn Leu Lys Ala Leu Ala Ala Leu
1               5                   10                  15
```

Ala Lys Lys Ile Leu
            20

<210> SEQ ID NO 14
<211> LENGTH: 16
<212> TYPE: PRT
<213> ORGANISM: Artificial Sequence
<220> FEATURE:
<223> OTHER INFORMATION: synthetic construct

<400> SEQUENCE: 14

Arg Val Ile Arg Val Trp Phe Gln Asn Lys Arg Cys Lys Asp Lys Lys
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: synthetic construct

<400> SEQUENCE: 15

Arg Gln Ile Lys Ile Trp Phe Gln Asn Arg Arg Met Lys Trp Lys Lys
1               5                   10                  15

<210> SEQ ID NO 16
<211> LENGTH: 20
<212> TYPE: PRT
<213> ORGANISM: Artificial Sequence
<220> FEATURE:
<223> OTHER INFORMATION: synthetic construct

<400> SEQUENCE: 16

Gly Leu Phe Glu Ala Ile Ala Gly Phe Ile Glu Asn Gly Trp Glu Gly
1               5                   10                  15

Met Ile Asp Gly
            20

<210> SEQ ID NO 17
<211> LENGTH: 15
<212> TYPE: PRT
<213> ORGANISM: Artificial Sequence
<220> FEATURE:
<223> OTHER INFORMATION: synthetic construct

<400> SEQUENCE: 17

Gly Trp Thr Leu Asn Ser Ala Gly Tyr Leu Leu Gly Lys Ile Asn
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: synthetic construct

<400> SEQUENCE: 18

Arg Ser Gln Ser Arg Ser Arg Tyr Tyr Arg Gln Arg Gln Arg Ser
1               5                   10                  15

<210> SEQ ID NO 19
<211> LENGTH: 8
<212> TYPE: PRT
<213> ORGANISM: Artificial Sequence
<220> FEATURE:
<223> OTHER INFORMATION: synthetic construct

<400> SEQUENCE: 19

Leu Ala Ile Pro Glu Gln Glu Tyr
1               5

<210> SEQ ID NO 20
<211> LENGTH: 8
<212> TYPE: PRT
<213> ORGANISM: Artificial Sequence
<220> FEATURE:
<223> OTHER INFORMATION: synthetic construct

<400> SEQUENCE: 20

Leu Gly Ile Ala Glu Gln Glu Tyr
1               5

<210> SEQ ID NO 21
<211> LENGTH: 8
<212> TYPE: PRT
<213> ORGANISM: Artificial Sequence
<220> FEATURE:
<223> OTHER INFORMATION: synthetic construct

<400> SEQUENCE: 21

Leu Gly Ile Pro Ala Gln Glu Tyr
1               5

<210> SEQ ID NO 22
<211> LENGTH: 8
<212> TYPE: PRT
<213> ORGANISM: Artificial Sequence
<220> FEATURE:
<223> OTHER INFORMATION: synthetic construct

<400> SEQUENCE: 22

Leu Gly Ile Pro Glu Ala Glu Tyr
1               5

<210> SEQ ID NO 23
<211> LENGTH: 8
<212> TYPE: PRT
<213> ORGANISM: Artificial Sequence
<220> FEATURE:
<223> OTHER INFORMATION: synthetic construct

<400> SEQUENCE: 23

Leu Gly Ile Pro Glu Gln Ala Tyr
1               5

<210> SEQ ID NO 24
<211> LENGTH: 8
<212> TYPE: PRT
<213> ORGANISM: Artificial Sequence
<220> FEATURE:
<223> OTHER INFORMATION: synthetic construct

<400> SEQUENCE: 24

Leu Gly Ile Ala Glu Ala Glu Tyr
1               5

<210> SEQ ID NO 25
<211> LENGTH: 8
<212> TYPE: PRT
<213> ORGANISM: Artificial Sequence
<220> FEATURE:
<223> OTHER INFORMATION: synthetic construct

```
<400> SEQUENCE: 25

Leu Gly Ile Pro Glu Ala Ala Tyr
1               5

<210> SEQ ID NO 26
<211> LENGTH: 8
<212> TYPE: PRT
<213> ORGANISM: Artificial Sequence
<220> FEATURE:
<223> OTHER INFORMATION: synthetic construct

<400> SEQUENCE: 26

Leu Gly Ile Ala Glu Gln Ala Tyr
1               5

<210> SEQ ID NO 27
<211> LENGTH: 8
<212> TYPE: PRT
<213> ORGANISM: Artificial Sequence
<220> FEATURE:
<223> OTHER INFORMATION: synthetic construct

<400> SEQUENCE: 27

Leu Gly Ile Ala Glu Ala Ala Tyr
1               5

<210> SEQ ID NO 28
<211> LENGTH: 18
<212> TYPE: PRT
<213> ORGANISM: Artificial Sequence
<220> FEATURE:
<223> OTHER INFORMATION: synthetic construct

<400> SEQUENCE: 28

Leu Leu Ile Ile Leu Arg Arg Arg Ile Arg Lys Gln Ala His Ala His
1               5                   10                  15

Ser Lys

<210> SEQ ID NO 29
<211> LENGTH: 12
<212> TYPE: PRT
<213> ORGANISM: Artificial Sequence
<220> FEATURE:
<223> OTHER INFORMATION: synthetic construct

<400> SEQUENCE: 29

Leu Lys Ala Leu Ala Ala Leu Ala Lys Lys Ile Leu
1               5                   10

<210> SEQ ID NO 30
<211> LENGTH: 18
<212> TYPE: PRT
<213> ORGANISM: Artificial Sequence
<220> FEATURE:
<223> OTHER INFORMATION: synthetic construct

<400> SEQUENCE: 30

Lys Leu Ala Leu Lys Leu Ala Leu Lys Ala Leu Lys Ala Ala Leu Lys
1               5                   10                  15

Leu Ala

<210> SEQ ID NO 31
<211> LENGTH: 21
<212> TYPE: PRT
<213> ORGANISM: Artificial Sequence
```

```
<220> FEATURE:
<223> OTHER INFORMATION: synthetic construct

<400> SEQUENCE: 31

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 32
<211> LENGTH: 8
<212> TYPE: PRT
<213> ORGANISM: Artificial Sequence
<220> FEATURE:
<223> OTHER INFORMATION: synthetic construct

<400> SEQUENCE: 32

Asp His Gln Leu Asn Pro Ala Phe
1               5

<210> SEQ ID NO 33
<211> LENGTH: 8
<212> TYPE: PRT
<213> ORGANISM: Artificial Sequence
<220> FEATURE:
<223> OTHER INFORMATION: synthetic construct

<400> SEQUENCE: 33

Asp Pro Lys Gly Asp Pro Lys Gly
1               5

<210> SEQ ID NO 34
<211> LENGTH: 18
<212> TYPE: PRT
<213> ORGANISM: Artificial Sequence
<220> FEATURE:
<223> OTHER INFORMATION: synthetic construct

<400> SEQUENCE: 34

Val Thr Val Thr Val Thr Val Thr Val Thr Gly Lys Gly Asp Pro Lys
1               5                   10                  15

Pro Asp

<210> SEQ ID NO 35
<211> LENGTH: 16
<212> TYPE: PRT
<213> ORGANISM: Artificial Sequence
<220> FEATURE:
<223> OTHER INFORMATION: synthetic construct

<400> SEQUENCE: 35

Arg Gln Ile Lys Ile Trp Phe Gln Asn Arg Arg Met Lys Trp Lys Lys
1               5                   10                  15

<210> SEQ ID NO 36
<211> LENGTH: 13
<212> TYPE: PRT
<213> ORGANISM: Artificial Sequence
<220> FEATURE:
<223> OTHER INFORMATION: synthetic construct

<400> SEQUENCE: 36

Gly Arg Lys Lys Arg Arg Gln Arg Arg Arg Pro Pro Gln
1               5                   10
```

```
<210> SEQ ID NO 37
<211> LENGTH: 27
<212> TYPE: PRT
<213> ORGANISM: Artificial Sequence
<220> FEATURE:
<223> OTHER INFORMATION: synthetic construct

<400> SEQUENCE: 37

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 38
<211> LENGTH: 10
<212> TYPE: PRT
<213> ORGANISM: Artificial Sequence
<220> FEATURE:
<223> OTHER INFORMATION: synthetic construct

<400> SEQUENCE: 38

Gly Arg Lys Lys Arg Arg Gln Arg Arg Arg
1               5                   10

<210> SEQ ID NO 39
<211> LENGTH: 7
<212> TYPE: PRT
<213> ORGANISM: Artificial Sequence
<220> FEATURE:
<223> OTHER INFORMATION: synthetic construct

<400> SEQUENCE: 39

Arg Arg Arg Arg Arg Arg Arg
1               5

<210> SEQ ID NO 40
<211> LENGTH: 8
<212> TYPE: PRT
<213> ORGANISM: Artificial Sequence
<220> FEATURE:
<223> OTHER INFORMATION: synthetic construct

<400> SEQUENCE: 40

Arg Arg Arg Arg Arg Arg Arg Arg
1               5

<210> SEQ ID NO 41
<211> LENGTH: 9
<212> TYPE: PRT
<213> ORGANISM: Artificial Sequence
<220> FEATURE:
<223> OTHER INFORMATION: synthetic construct

<400> SEQUENCE: 41

Arg Arg Arg Arg Arg Arg Arg Arg Arg
1               5

<210> SEQ ID NO 42
<211> LENGTH: 10
<212> TYPE: PRT
<213> ORGANISM: Artificial Sequence
<220> FEATURE:
<223> OTHER INFORMATION: synthetic construct

<400> SEQUENCE: 42

Arg Arg Arg Arg Arg Arg Arg Arg Arg Arg
1               5                   10
```

```
<210> SEQ ID NO 43
<211> LENGTH: 10
<212> TYPE: PRT
<213> ORGANISM: Artificial Sequence
<220> FEATURE:
<223> OTHER INFORMATION: synthetic construct

<400> SEQUENCE: 43

Arg Arg Arg Arg Arg Arg Arg Arg Arg Arg
1               5                   10

<210> SEQ ID NO 44
<211> LENGTH: 33
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (33)..(33)
<223> OTHER INFORMATION: Xaa can be 2 to 15 Arg independently in the L
      and/or D form

<400> SEQUENCE: 44

Tyr Thr Ile Trp Met Pro Glu Asn Pro Arg Pro Gly Thr Pro Cys Asp
1               5                   10                  15

Ile Phe Thr Asn Ser Arg Gly Lys Arg Ala Ser Asn Gly Gly Gly Gly
            20                  25                  30

Xaa
```

PLATINUM COMPLEXES AND USES THEREOF

This application claims priority to U.S. Appl. No. 62/583,432, filed Nov. 8, 2017, the contents of which are herein incorporated by reference in its entirety.

BACKGROUND

Platinum-based compounds are among the most widely used drug classes in cancer therapy. Almost half of the chemotherapy regimens contain a platinum drug. The widespread use of platinum agents in the treatment of cancer began with the discovery of the antineoplastic activity of cisplatin in the 1960s. Despite the pervasiveness of platinum drugs in cancer treatment regimens, broader application of platinum-based drugs such as cisplatin and oxaliplatin is ultimately limited by their low solubility, short half-life, and the substantial risk of severe toxicities, including neurotoxicity. Improvement of drug targeting and delivery systems are effective approaches to mitigate these disadvantages.

There is, therefore, a great need for developing platinum-based drug targeting and delivery systems that are capable preferentially delivering cytotoxic platinum drug-based payloads that have wider therapeutic indices and more favorable toxicity profiles than currently administered.

The provided compositions preferentially deliver therapeutic agent pay loads, such as platinum-based drugs to hyperproliferative cells including cancer cells and provide significant improvements in efficacy and safety over conventional platinum therapy-based treatment regimens.

BRIEF SUMMARY

The disclosure generally relates to compositions comprising therapeutic agent complexes and to methods of making and using the compositions. In particular embodiments, the disclosure provides compositions comprising platinum-based drug complexes and to methods of making and using these compositions. In some embodiments, the disclosure provides a composition comprising a complex of a therapeutic agent such as a platinum-based drug therapeutic agent and one or more polyglutamate molecules. In some embodiments, the disclosure provides a composition comprising a complex of a therapeutic agent such as a platinum-based drug therapeutic agent and cyclodextrin. In some embodiments, the compositions comprise a complex containing a platinum-based drug complex. In some embodiments, the platinum-based drug complex comprises cisplatin or a salt thereof. In some embodiments, the platinum-based drug complex comprises oxaliplatin, or a salt thereof. In some embodiments, the platinum-based drug complex comprises stratoplatin, paraplatin, platinol, cycloplatin, dexormaplatin, spiroplatin, picoplatin, triplatin, tetraplatin, iproplatin, ormaplatin, zeniplatin, platinum-triamine, traplatin, enloplatin, JM-216, 254-S, NK121, CI-973, DWA 2114R, NDDP, or dedaplatin, or a salt thereof. Compositions comprising delivery vehicles such as liposomes that contain/encapsulate the therapeutic agent complexes are also provided, as are methods of making and using the provided compositions to treat hyperproliferative diseases such as cancer. In some embodiments, the disclosure provides liposome compositions that comprise a liposome encapsulating a complex of a platinum-based chemotherapeutic agent (e.g., cisplatin and oxaliplatin, or a salt thereof) and one or more polyglutamate molecule(s) (e.g., a polyglutamate having the structure ($\alpha$-L-glutamyl)$_n$, ($\gamma$-L-glutamyl)$_n$, ($\alpha$-D-glutamyl)$_n$ and ($\gamma$-D-glutamyl)$_n$, where n=1, 2, 3, 4, 5, 2-8, 2-10, 4-6, or >5; and molecules such as polyglutamated folates or polyglutamated antifolates containing these polyglutamate structures). In some embodiments, the liposome composition comprises a liposome encapsulating a complex of a platinum-based chemotherapeutic agent (e.g., cisplatin, and oxaliplatin, or a salt thereof) and cyclodextrin (e.g., a derivatized beta cyclodextrin). In some embodiments, the liposome is pegylated. In additional embodiments, the liposome composition further comprises one or more pharmaceutically acceptable carriers.

In one embodiment, the disclosure provides a composition comprising a delivery vehicle, such as a liposome composition that comprises a pegylated liposome encapsulating a complex of a therapeutic agent or a salt thereof, and one or more polyglutamate molecule(s). In some embodiments, the therapeutic agent complex comprises a polyglutamate having the structure ($\alpha$-L-glutamyl)$_n$, where n=1, 2, 3, 4, 5, 2-8, 2-10, 4-6, or >5. In some embodiments, the therapeutic agent complex comprises a molecule containing the structure X-($\alpha$-L-glutamyl)$_n$, where n=1, 2, 3, 4, 5, 2-8, 2-10, 4-6, or >5, and X is the structure of the non-therapeutic agent molecule(s) in the complex. In further embodiments, the therapeutic agent of the complex is a platinum-based drug agent. In one embodiment, the platinum-based chemotherapeutic agent is cisplatin. In another embodiment, the platinum-based chemotherapeutic agent is a cisplatin analog. In an additional embodiment, the platinum-based chemotherapeutic agent is oxaliplatin. In an additional embodiment, the platinum-based chemotherapeutic agent is selected from the group: nedaplatin, heptaplatin, and lobaplatin. In another embodiment, the platinum-based chemotherapeutic agent is selected from the group: nedaplatin, heptaplatin, and lobaplatin. In an additional embodiment, the platinum-based chemotherapeutic agent is selected from the group: stratoplatin, paraplatin, platinol, cycloplatin, dexormaplatin, spiroplatin, picoplatin, triplatin, tetraplatin, iproplatin, ormaplatin, zeniplatin, platinum-triamine, traplatin, enloplatin, JM-216, 254-S, NK 121, CI-973, DWA 2114R, NDDP, and dedaplatin In further embodiments, the disclosure provides a composition comprising a delivery vehicle, such as a liposome composition that comprises a pegylated liposome encapsulating a complex of a therapeutic agent or a salt thereof, and the therapeutic agent complex comprises a polyglutamated antifolate having the structure Antifolate-($\alpha$-L-glutamyl)$_n$, where n=2-8, and a second therapeutic agent that is not a polyglutamated antifolate. In further embodiments, the second therapeutic agent is a platinum-based drug agent. In one embodiment, the platinum-based chemotherapeutic agent is cisplatin. In another embodiment, the platinum-based chemotherapeutic agent is a cisplatin analog. In an additional embodiment, the platinum-based chemotherapeutic agent is oxaliplatin. In an additional embodiment, the platinum-based chemotherapeutic agent is selected from the group: nedaplatin, heptaplatin, and lobaplatin. In another embodiment, the platinum-based chemotherapeutic agent is selected from the group: nedaplatin, heptaplatin, and lobaplatin. In an additional embodiment, the platinum-based chemotherapeutic agent is selected from the group: stratoplatin, paraplatin, platinol, cycloplatin, dexormaplatin, spiroplatin, picoplatin, triplatin, tetraplatin, iproplatin, ormaplatin, zeniplatin, platinum-triamine, traplatin, enloplatin, JM-216, 254-S, NK 121, CI-973, DWA 2114R, NDDP, and dedaplatin.

In another embodiment, the disclosure provides a composition comprising a delivery vehicle, such as a liposome composition that comprises a pegylated liposome encapsulating a complex of a therapeutic agent or a salt thereof, and the therapeutic agent complex comprises a polyglutamate having the structure (γ-L-glutamyl)$_n$, (α-D-glutamyl)$_n$, or (γ-D-glutamyl)$_n$, where n=2-8. In some embodiments, the therapeutic agent-polyglutamate complex comprises a molecule containing the structure X-(γ-L-glutamyl)$_n$, X-(α-D-glutamyl)$_n$, or X-(γ-D-glutamyl)$_n$, where n=1, 2, 3, 4, 5, 2-8, 2-10, 4-6, or >5, and X is the structure of the non-therapeutic agent molecule(s) in the complex. In further embodiments, the therapeutic agent of the complex is a platinum-based drug agent. In one embodiment, the platinum-based chemotherapeutic agent is cisplatin. In another embodiment, the platinum-based chemotherapeutic agent is a cisplatin analog. In an additional embodiment, the platinum-based chemotherapeutic agent is oxaliplatin. In an additional embodiment, the platinum-based chemotherapeutic agent is selected from the group: nedaplatin, heptaplatin, and lobaplatin. In another embodiment, the platinum-based chemotherapeutic agent is selected from the group: nedaplatin, heptaplatin, and lobaplatin. In an additional embodiment, the platinum-based chemotherapeutic agent is selected from the group: stratoplatin, paraplatin, platinol, cycloplatin, dexormaplatin, spiroplatin, picoplatin, triplatin, tetraplatin, iproplatin, ormaplatin, zeniplatin, platinum-triamine, traplatin, enloplatin, JM-216, 254-S, NK 121, CI-973, DWA 2114R, NDDP, and dedaplatin.

In further embodiments, the disclosure provides a composition comprising a delivery vehicle, such as a liposome composition that comprises a pegylated liposome encapsulating a complex that comprises a polyglutamated antifolate having the structure Antifolate-(γ-L-glutamyl)$_n$, Antifolate-(α-D-glutamyl)$_n$, or Antifolate-(γ-D-glutamyl)$_n$, where n=1, 2, 3, 4, 5, 2-8, 2-10, 4-6, or >5, and a second therapeutic agent that is not a polyglutamated antifolate. In further embodiments, the second therapeutic agent is a platinum-based drug agent. In one embodiment, the platinum-based chemotherapeutic agent is cisplatin. In another embodiment, the platinum-based chemotherapeutic agent is a cisplatin analog. In an additional embodiment, the platinum-based chemotherapeutic agent is oxaliplatin. In an additional embodiment, the platinum-based chemotherapeutic agent is selected from the group: nedaplatin, heptaplatin, and lobaplatin. In another embodiment, the platinum-based chemotherapeutic agent is selected from the group: nedaplatin, heptaplatin, and lobaplatin. In an additional embodiment, the platinum-based chemotherapeutic agent is selected from the group: stratoplatin, paraplatin, platinol, cycloplatin, dexormaplatin, spiroplatin, picoplatin, triplatin, tetraplatin, iproplatin, ormaplatin, zeniplatin, platinum-triamine, traplatin, enloplatin, JM-216, 254-S, NK 121, CI-973, DWA 2114R, NDDP, and dedaplatin.

In some embodiments, the therapeutic agent-polyglutamate complex comprises a polyglutamated antifolate (e.g., having the structure Antifolate-[glutamyl]$_n$, where n=1, 2, 3, 4, 5, 2-8, 2-10, 4-6, or >5: where [glutamyl]n refers to the glutamyl attached to the antifolate, n is the number of attached glutamyls, and "Antifolate" is a polyglutamatable antifolate), and the therapeutic agent is not a polyglutamated antifolate. In some embodiments, the therapeutic agent is a platinum-based drug agent. In one embodiment, the platinum-based chemotherapeutic agent is cisplatin. In another embodiment, the platinum-based chemotherapeutic agent is a cisplatin analog. In an additional embodiment, the platinum-based chemotherapeutic agent is carboplatin. In an additional embodiment, the platinum-based chemotherapeutic agent is oxaliplatin. In an additional embodiment, the platinum-based chemotherapeutic agent is selected from the group: nedaplatin, heptaplatin, and lobaplatin. In another embodiment, the platinum-based chemotherapeutic agent is selected from the group: nedaplatin, heptaplatin, and lobaplatin. In an additional embodiment, the platinum-based chemotherapeutic agent is selected from the group: stratoplatin, paraplatin, platinol, cycloplatin, dexormaplatin, spiroplatin, picoplatin, triplatin, tetraplatin, iproplatin, ormaplatin, zeniplatin, platinum-triamine, traplatin, enloplatin, JM-216, 254-S, NK 121, CI-973, DWA 2114R, NDDP, and dedaplatin.

In some embodiments, the therapeutic agent-polyglutamate complex comprises a polyglutamated folate (e.g., having the structure Folate-[glutamyl]$_n$, where n=1, 2, 3, 4, 5, 2-8, 2-10, 4-6, or >5; and wherein-[glutamyl]$_n$ refers to the glutamyl attached to the folate and n is the number of attached glutamates, and the therapeutic agent is not polyglutamated folate. In some embodiments, the therapeutic agent is a platinum-based drug agent. In one embodiment, the platinum-based chemotherapeutic agent is cisplatin. In another embodiment, the platinum-based chemotherapeutic agent is a cisplatin analog. In an additional embodiment, the platinum-based chemotherapeutic agent is oxaliplatin. In an additional embodiment, the platinum-based chemotherapeutic agent is selected from the group: nedaplatin, heptaplatin, and lobaplatin. In another embodiment, the platinum-based chemotherapeutic agent is selected from the group: nedaplatin, heptaplatin, and lobaplatin. In an additional embodiment, the platinum-based chemotherapeutic agent is selected from the group: stratoplatin, paraplatin, platinol, cycloplatin, dexormaplatin, spiroplatin, picoplatin, triplatin, tetraplatin, iproplatin, ormaplatin, zeniplatin, platinum-triamine, traplatin, enloplatin, JM-216, 254-S, NK 121, CI-973, DWA 2114R, NDDP, and dedaplatin.

In additional embodiments, the disclosure provides a composition comprising a delivery vehicle, such as a liposome composition that comprises a pegylated liposome encapsulating a complex of a therapeutic agent or a salt thereof, and a cyclodextrin.

In one embodiment, the disclosure provides a liposome composition comprising a pegylated liposome encapsulating a complex of a platinum-based chemotherapeutic agent or a salt thereof and a cyclodextrin. In some embodiments, the platinum-cyclodextrin complex comprises cisplatin. In other embodiments, the platinum-cyclodextrin complex comprises a cisplatin analog. In other embodiments, the platinum-cyclodextrin complex comprises oxaliplatin. In additional embodiments, the platinum-cyclodextrin complex comprises a platinum-based chemotherapeutic agent selected from the group: nedaplatin, heptaplatin, and lobaplatin. In additional embodiments, the platinum-cyclodextrin complex comprises a platinum-based chemotherapeutic agent selected from the group: stratoplatin, paraplatin, platinol, cycloplatin, dexormaplatin, spiroplatin, picoplatin, triplatin, tetraplatin, iproplatin, ormaplatin, zeniplatin, platinum-triamine, traplatin, enloplatin, JM-216, 254-S, NK 121, CI-973, DWA 2114R, NDDP, and dedaplatin.

The cyclodextrin (CD) complexed with the platinum-based chemotherapeutic agent in the provided liposome compositions can be derivatized or underivatized. In some embodiments, the cyclodextrin is derivatized. In further embodiments, the cyclodextrin is a derivatized beta-cyclodextrin (e.g., a hydroxypropyl beta-cyclodextrin (HP-beta-CD), and a sulfobutyl ether beta-CD (SBE)-beta-cyclodextrin). In some embodiments, the cyclodextrin is a derivatized beta-cyclodextrin comprising: 1, 2, 3, 4, 5, 6, 7, 8, 9, 10, or more 2-hydroxylpropyl-3- group substitutions of hydroxy groups: or 1, 2, 3, 4, 5, 6, 7, 8, 9, 10, or more sulfoalkyl ether group substitutions of hydroxy groups. In further embodiments, the cyclodextrin is a derivatized beta-cyclodextrin comprising: 1, 2, 3, 4, 5, 6, 7, 8, 9, 10, or more sulfobutyl ether group substitutions of hydroxy groups.

In some embodiments, the cyclodextrin complexed with the platinum-based chemotherapeutic agent in the provided liposome compositions is a derivatized cyclodextrin of Formula I:

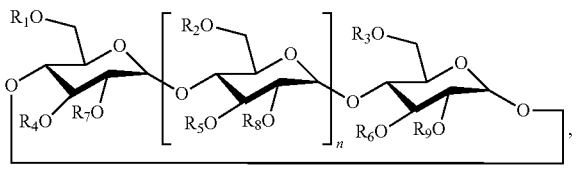

wherein: n is 4, 5, or 6; and wherein $R_1$, $R_2$, $R_3$, $R_4$, $R_5$, $R_6$, $R_7$, $R_8$, and $R_9$ are each, independently, —H, a straight chain or branched $C_1$-$C_8$-alkylene group, a 2-hydroxylpropyl-3- group: or an optionally substituted straight-chain or branched $C_1$-$C_6$ group, wherein at least one of $R_1$, $R_2$, $R_3$, $R_4$, $R_5$, $R_6$, $R_7$, $R_8$ and $R_9$ is a straight-chain or branched $C_1$-$C_8$-alkylene group or a 2-hydroxylpropyl-3- group.

In some embodiments, the cyclodextrin complexed with the platinum-based chemotherapeutic agent is a derivatized cyclodextrin of Formula II:

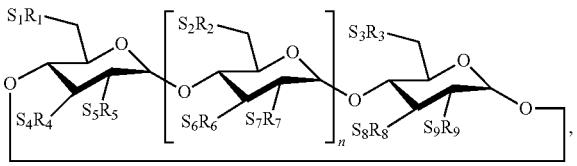

wherein: n is 4, 5, or 6; and wherein $R_1$, $R_2$, $R_3$, $R_4$, $R_5$, $R_6$, $R_7$, $R_8$, and $R_9$ are each, independently, —O— or a —O—($C_2$-$C_6$ alkylene)-$SO_3^-$ group: wherein at least one of $R_1$ and $R_2$ is independently a —O—($C_2$-$C_6$ alkylene)-$SO_3^-$ group; and $S_1$, $S_2$, $S_3$, $S_4$, $S_5$, $S_6$, $S_7$, $S_8$, and $S_9$ are each, independently, a —H or a H or a pharmaceutically acceptable cation. In further embodiments, the pharmaceutically acceptable cation is selected from: an alkali metal such as $Li^+$, $Na^+$, or $K^+$; an alkaline earth metal such as $Ca^{+2}$, or $Mg^{+2}$, and ammonium ions and amine cations such as the cations of (C1-C6)-alkylamines, piperidine, pyrazine, (C1-C6)-alkanolamine and (C4-C8)-cycloalkanolamine.

In some embodiments, liposomes in the provide liposome composition are anionic or neutral. In further embodiments, liposomes in the composition have a zeta potential that is less than or equal to zero. In further embodiments, liposomes in the composition has a zeta potential that is between 0 to −150 mV. In other embodiments, liposomes in the composition are cationic. In further embodiments, liposomes in the composition have a zeta potential that is between 1 and 100 mV.

In some embodiments, liposomes in the provided liposome compositions are pegylated. In some embodiments, the polyethylene glycol of the pegylated liposomes has a number average molecular weight of 200 to 5000 daltons. In some embodiments, the liposome compositions comprise pegylated liposomes containing an internal phase having a pH in the range of 2.8-6.8. In some embodiments, the internal phase of pegylated liposomes in the liposome composition comprise trehalose (e.g., 5% to 20% weight of trehalose).

In additional embodiments, the liposome composition comprises liposomes that contain a targeting moiety. In some embodiments, the targeting moiety is attached to one or both of a PEG and the exterior of the liposome. In additional embodiments, the targeting moiety has a specific affinity for a surface antigen on a target cell of interest. In some embodiments, the targeting moiety is a polypeptide. In additional embodiments, the targeting moiety is an antibody, a humanized antibody, an antigen binding fragment of an antibody, a single chain antibody, a single-domain antibody, a bi-specific antibody, a synthetic antibody, a pegylated antibody, or a multimeric antibody. In some embodiments, the liposome composition comprises liposomes that contain from 30 to 500 targeting moieties. In further embodiments, the liposome composition comprises liposomes that contain from 30 to 200 targeting moieties.

In some embodiments, the liposome composition comprises liposomes that contain one or more of an immunostimulatory agent, a detectable marker and a maleimide disposed on at least one of the PEG and the exterior of the liposome.

In additional embodiments, the provided liposome compositions comprise a pegylated liposome that further comprise a second complex formed by a therapeutic agent or a salt, acid or free base form thereof, and one or more polyglutamate molecules. In some embodiments, the therapeutic agent of the second complex is a chemotherapeutic agent, an antimetabolite, and/or a taxane. In some embodiments, the therapeutic agent of the second complex is gemcitabine, a gemcitabine-based therapeutic agent, doxorubicin, a doxorubicin-based therapeutic agent, an antifolate, an antifolate-based chemotherapeutic, or a salt, acid or free base form thereof.

In some embodiments, the provided liposome compositions comprise a pegylated liposome that further comprises a second complex formed by a therapeutic agent or a salt, acid or free base form thereof, and one or more polyglutamate molecules. In some embodiments, the therapeutic agent of the second complex is a chemotherapeutic agent, an antimetabolite, and/or a taxane. In some embodiments, the therapeutic agent of the second complex is a member selected from the group: gemcitabine, a gemcitabine-based therapeutic agent, doxorubicin, an antifolate, an antifolate-based chemotherapeutic, or a salt, acid or free base form thereof.

In additional embodiments, the provided liposome compositions comprises a pegylated liposome that further comprises a second complex formed by a therapeutic agent or a salt, acid or free base form thereof, and a cyclodextrin. In some embodiments, the therapeutic agent of the second complex is a member selected from the group: gemcitabine, a gemcitabine-based therapeutic agent, doxorubicin, an antifolate, an antifolate-based chemotherapeutic, or a salt, acid or free base form thereof. The cyclodextrin of the second complex can be derivatized or underivatized. In some embodiments, the cyclodextrin is derivatized. In further embodiments, the cyclodextrin is a derivatized beta-cyclodextrin (e.g., a hydroxypropyl beta-cyclodextrin (HP-beta-CD), and a sulfobutyl ether beta-CD (SBE)-beta-cyclodextrin). In some embodiments, the cyclodextrin of the second complex is a derivatized beta-cyclodextrin comprising: 1, 2, 3, 4, 5, 6, 7, 8, 9, 10, or more 2-hydroxylpropyl-3- group substitutions of hydroxy groups: or 1, 2, 3, 4, 5, 6, 7, 8, 9, 10, or more sulfoalkyl ether group substitutions of hydroxy groups. In further embodiments, the cyclodextrin of the second complex is a derivatized beta-cyclodextrin comprising: 1, 2, 3, 4, 5, 6, 7, 8, 9, 10, or more sulfobutyl ether group substitutions of hydroxy groups.

In some embodiments, the cyclodextrin of the second complex contained in the liposomes of the liposome composition (i.e., the complex formed by a therapeutic agent or a salt thereof, and a cyclodextrin) is a derivatized cyclodextrin of Formula I:

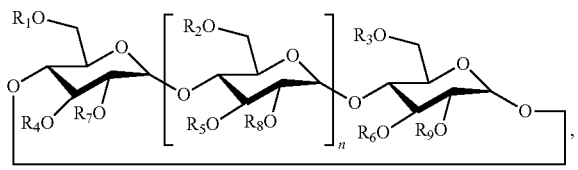

wherein: n is 4, 5, or 6; and wherein $R_1$, $R_2$, $R_3$, $R_4$, $R_5$, $R_6$, $R_7$, $R_8$, and $R_9$ are each, independently, —H, a straight chain or branched $C_1$-$C_8$-alkylene group, a 2-hydroxylpropyl-3- group: or an optionally substituted straight-chain or branched $C_1$-$C_6$ group, wherein at least one of $R_1$, $R_2$, $R_3$, $R_4$, $R_5$, $R_6$, $R_7$, $R_8$ and $R_9$ is a straight-chain or branched $C_1$-$C_8$-alkylene group or a 2-hydroxylpropyl-3- group.

In some embodiments, the cyclodextrin of the second complex contained in the liposomes of the liposome composition is a derivatized cyclodextrin of Formula II:

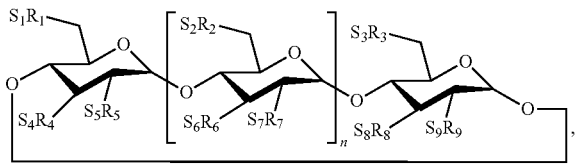

wherein: n is 4, 5, or 6; and wherein $R_1$, $R_2$, $R_3$, $R_4$, $R_5$, $R_6$, $R_7$, $R_8$, and $R_9$ are each, independently, —O— or a —O—($C_2$-$C_6$ alkylene)-$SO_3^-$ group: wherein at least one of $R_1$ and $R_2$ is independently a —O—($C_2$-$C_6$ alkylene)-$SO_3^-$ group; and $S_1$, $S_2$, $S_3$, $S_4$, $S_5$, $S_6$, $S_7$, $S_8$, and $S_9$ are each, independently, a —H or a H or a pharmaceutically acceptable cation. In further embodiments, the wherein the pharmaceutically acceptable cation is selected from: an alkali metal such as $Li^+$, $Na^+$, or $K^+$; an alkaline earth metal such as $Ca^{+2}$, or $Mg^{+2}$, and ammonium ions and amine cations such as the cations of (C1-$C_6$)-alkylamines, piperidine, pyrazine, (C1-$C_6$)-alkanolamine and (C4-C8)-cycloalkanolamine.

In some embodiments, liposomes in the liposome composition comprise between 100 to 100,000 of the second complex formed by the therapeutic agent or a salt thereof, and the cyclodextrin. In some embodiments, the liposome composition comprises liposomes that have a diameter in the range of 20 nm (nanometer) to 200 nm. In some embodiments, the liposome composition comprises liposomes that have a diameter in the range of for example, 10-250 nm. In some embodiments, the liposomes have a diameter in the range of for example, 30-150 nm. In other embodiments, the liposomes have a diameter in the range of 40-70 nm. In some embodiments, liposomes in the composition comprise between 100 to 100,000 platinum-based chemotherapeutic agent/cyclodextrin complexes. In some embodiments, the cyclodextrin of the second complex is different from the cyclodextrin of the platinum-based chemotherapeutic agent complex. In some embodiments, the liposome comprises the same cyclodextrin in the second complex and the platinum-based chemotherapeutic agent complex. In some embodiments, the liposome comprises a cyclodextrin in the second complex that is different from the cyclodextrin of the platinum-based chemotherapeutic agent complex.

According to some embodiments, the provided liposome compositions further comprise one or more of an immunostimulatory agent, a detectable marker and a maleimide, wherein the immunostimulatory agent, the detectable marker or the maleimide is attached to the PEG or the exterior of the liposome. In some embodiments, the immunostimulating agent is at least one member selected from the group: a protein immunostimulating agent: a nucleic acid immunostimulating agent: a chemical immunostimulating agent: a hapten; and an adjuvant. In some embodiments, the immunostimulating agent is at least one selected from the group: a fluorescein: a fluorescein isothiocyanate (FITC): a DNP: a beta glucan: a beta-1,3-glucan; and a beta-1,6-glucan. In some embodiments, the immunostimulatory agent and the detectable marker is the same. In some embodiments, the liposome composition comprises a hapten. In further embodiments, the hapten comprises one or more of fluorescein or Beta 1,6-glucan.

In some embodiments, the liposomes of the provided liposome compositions further comprise at least one cryoprotectant selected from the group consisting of mannitol; trehalose: sorbitol; and sucrose. In additional embodiments, the provided liposomal composition is in unit dosage form. In some embodiments, pharmaceutical compositions comprising the liposome compositions disclosed herein are provided.

In some embodiments, the disclosure is directed to the use of the provided liposome compositions in the treatment of disease. In some embodiments, the disclosure is directed to use of the provided liposome compositions in the manufacture of a medicament for the treatment of disease.

In some embodiments, the disclosure provides a method of killing a hyperproliferative cell that comprises contacting a hyperproliferative cell with a liposome composition provided herein. In further embodiments, the hyperproliferative cell is a cancer cell.

In some embodiments, the disclosure provides a method for treating or preventing disease in a subject needing such treatment or prevention, the method comprising administering an effective amount of a liposome composition provided herein to a subject in need thereof. In some embodiments, the disease is a hyperproliferative disorder such as cancer. In some embodiments, the administration is parenteral. In some embodiments, the administration is intravenous. In some embodiments, the administration is subcutaneous.

In additional embodiments, the disclosure provides a method for treating cancer in a subject, comprising administering an effective amount of a liposome composition disclosed herein to a subject having or at risk of having cancer. In further embodiments, the cancer is a member selected from the group: lung cancer, pancreatic cancer, breast cancer, ovarian cancer, prostate cancer, head and neck cancer, gastric cancer, gastrointestinal cancer, colorectal cancer, esophageal cancer, cervical cancer, liver cancer, kidney cancer, biliary duct cancer, gallbladder cancer, bladder cancer, sarcoma (e.g., osteosarcoma), brain cancer, central nervous system cancer, and melanoma; and a hematologic malignancy such as for example, a leukemia, a lymphoma and other B cell malignancies, myeloma and other plasma cell dyscrasias. In some embodiments, the administration is parenteral. In some embodiments, the administration is intravenous. In some embodiments, the administration is subcutaneous.

In other embodiments, the disclosure provides a method for treating cancer in a subject, comprising administering an effective amount of a liposome composition to a tumor expressing an antigen on its surface, the method comprising: administering a liposome composition disclosed herein to a subject having a tumor expressing the antigen in an amount to deliver an effective dose of the liposome composition to the tumor. In some embodiments, the administration is parenteral. In some embodiments, the administration is intravenous. In some embodiments, the administration is subcutaneous.

In additional embodiments, the disclosure provides a method for treating cancer that comprises administering an effective amount of a liposome composition provided herein to a subject, wherein the liposome comprises a targeting moiety with specific affinity for an antigen expressed on the surface of a cancer cell, and wherein the subject has or is at risk of having a cancer cell that expresses the antigen. In further embodiments, the antigen is a folate receptor. In some embodiments, the administration is parenteral. In some embodiments, the administration is intravenous. In some embodiments, the administration is subcutaneous.

Also provided is maintenance therapy that comprise administering an effective amount of a liposome composition disclosed herein to a subject that is undergoing or has undergone cancer therapy. In some embodiments, the administration is parenteral. In some embodiments, the administration is intravenous. In some embodiments, the administration is subcutaneous.

In another aspect, a kit comprising a liposome composition provided herein, and instructions for use, is provided. In some embodiments, the kit comprises a container comprising a liposome composition disclosed herein. In some embodiments, the kit further comprises a second container comprising a second liposome composition disclosed herein or a pharmaceutically acceptable carrier.

In some embodiments, the disclosure provides:

[1] a liposome composition comprising a liposome encapsulating
  (a) a complex of a platinum-based chemotherapeutic agent or a salt thereof and one or more polyglutamates or
  (b) a complex of a platinum-based chemotherapeutic agent or a salt thereof and a cyclodextrin;
  wherein the liposome comprises one or more pharmaceutically acceptable carriers; and a pegylated liposome:

[2] the liposome composition of [1], wherein the platinum-based chemotherapeutic agent is cisplatin or a cisplatin analog;

[3] the liposome composition according to [1] or [2], wherein the platinum-based chemotherapeutic agent is a member selected from the group: cisplatin, oxaliplatin, stratoplatin, paraplatin, platinol, cycloplatin, dexormaplatin, spiroplatin picoplatin, nedaplatin, triplatin, tetraplatin, lipoplatin, lobaplatin, ormaplatin, zeniplatin, platinum-triamine, traplatin, enloplatin, JM-216, 254-S, NK 121, CI-973, DWA2114R, NDDP, and dedaplatin;

[4] the liposome composition according to any of [1]-[3], wherein the liposome encapsulates a complex of a platinum-based chemotherapeutic agent or a salt thereof and a cyclodextrin, and wherein the cyclodextrin is a derivatized or underivatized beta-cyclodextrin;

[5] the liposome composition of [4], wherein the cyclodextrin is a derivatized beta-cyclodextrin;

[6] the liposome composition of [4], wherein the cyclodextrin (CD) is a hydroxypropyl beta-CD (HP-beta-CD), or a sulfobutyl ether beta-CD ((SBE)-beta-CD);

[7] the liposome composition of [5], wherein the cyclodextrin is a derivatized beta-cyclodextrin comprising:
  (a) 1, 2, 3, 4, 5, 6, 7, 8, 9, 10, or more 2-hydroxylpropyl-3- group substitutions of hydroxy groups; or
  (b) 1, 2, 3, 4, 5, 6, 7, 8, 9, 10, or more sulfoalkyl ether group substitutions of hydroxy groups;

[8] the liposome composition of [7], wherein the cyclodextrin is a derivatized beta-cyclodextrin comprising: 1, 2, 3, 4, 5, 6, 7, 8, 9, 10, or more sulfobutyl ether group substitutions of hydroxy groups;

[9] the liposome composition of [5], wherein the cyclodextrin is a derivatized beta-cyclodextrin of Formula III:

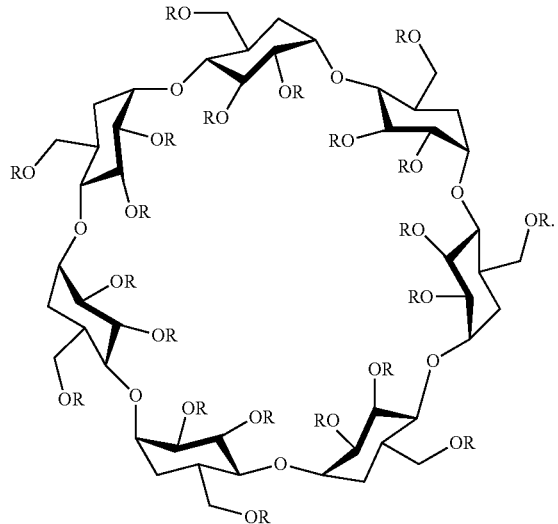

wherein R equals:
  (a) $(H)_{21-X}$ or $(-CH_2)_4-SO_3Na)_x$, and x=1.0-10.0, 1.0-5.0, 6.0-7.0 or 8.0-10.0;
  (b) $(H)_{21-X}$ or $(-CH_2CH(OH)CH_3)_x$, and x=1.0-10.0, 1.0-5.0, 6.0-7.0 or 8.0-10.0;
  (c) $(H)_{21-X}$ or (sulfoalkyl ether)$_x$, and x=1.0-10.0, 1.0-5.0, 6.0-7.0 or 8.0-10.0; or $(H)_{21-X}$ or $(-CH_2)_4-SO_3Na)_x$, and x=1.0-10.0, 1.0-5.0, 6.0-7.0 or 8.0-10.0;

[10] the liposome composition according to any of [1]-[9], wherein the cyclodextrin is a derivatized cyclodextrin of Formula I:

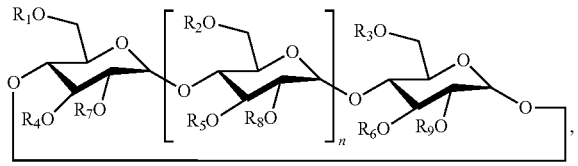

wherein: n is 4, 5, or 6; and
wherein $R_1$, $R_2$, $R_3$, $R_4$, $R_5$, $R_6$, $R_7$, $R_8$, and $R_9$ are each, independently, —H, a straight chain or branched $C_1$-$C_8$-alkylene group, a 2-hydroxypropyl-3- group;

or an optionally substituted straight-chain or branched $C_1$-$C_6$ group, wherein at least one of $R_1$, $R_2$, $R_3$, $R_4$, $R_5$, $R_6$, $R_7$, $R_8$ and $R_9$ is a straight-chain or branched $C_1$-$C_8$-alkylene group or a 2-hydroxyl-propyl-3- group;

[11] the liposome composition of according to any of [1]-[9], wherein the cyclodextrin is a derivatized cyclodextrin of Formula II:

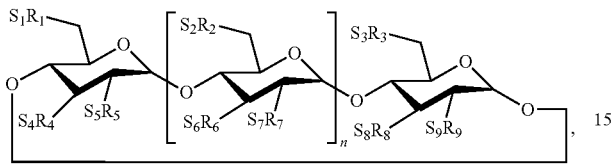

wherein: n is 4, 5, or 6; and
wherein $R_1$, $R_2$, $R_3$, $R_4$, $R_5$, $R_6$, $R_7$, $R_8$, and $R_9$ are each, independently, —O— or a —O—($C_2$-$C_6$ alkylene)-$SO_3^-$ group; wherein at least one of $R_1$ and $R_2$ is independently a —O—($C_2$-$C_6$ alkylene)-$SO_3^-$ group; and $S_1$, $S_2$, $S_3$, $S_4$, $S_5$, $S_6$, $S_7$, $S_8$, and $S_9$ are each, independently, a —H or a H or a pharmaceutically acceptable cation;

[12] the liposome composition of [11], wherein the pharmaceutically acceptable cation is selected from: an alkali metal such as Li$^+$, Na$^+$, or K$^+$; an alkaline earth metal such as Ca$^{+2}$, or Mg+$^2$; and ammonium ions and amine cations such as the cations of ($C_1$-$C_6$)-alkylamines, piperidine, pyrazine, ($C_1$-$C_6$)-alkanolamine, and ($C_4$-$C_8$)-cycloalkanolamin;

[13] the liposome composition according to any of [1]-[12], wherein each liposome comprises between 100 to 100,000 complexes formed by the platinum-based chemotherapeutic agent or salt thereof, and the cyclodextrin;

[14] the liposome composition according to any of [1]-[13], wherein the liposome has a diameter in the range of 20 nm to 200 nm;

[15] the liposome composition according to any of [1]-[13], wherein the liposome has a diameter in the range of 80 nm to 120 nm;

[16] the liposome composition according to any of [1]-[15], wherein the polyethylene glycol of the liposome has a number average molecular weight (Mn) of 200 to 5000 daltons;

[17] the liposome composition according to any of [1]-[16], wherein the liposome comprises a steric stabilizer;

[18] the liposome composition of [17], which comprises a steric stabilizer selected from the group consisting of polyethylene glycol (PEG); poly-L-lysine (PLL); monosialoganglioside (GM1); poly(vinyl pyrrolidone) (PVP); poly(acrylamide) (PAA); poly(2-methyl-2-oxazoline); poly(2-ethyl-2-oxazoline); phosphatidyl polyglycerol; poly[N-(2-hydroxypropyl) methacrylamide]; amphiphilic poly-N-vinylpyrrolidones; L-amino-acid-based polymer; and polyvinyl alcohol;

[19] the liposome composition according to any of [1]-[18], wherein the liposome comprises at least one of an anionic lipid and a neutral lipid;

[20] the liposome composition according to any of [1]-[19], wherein the liposome comprises at least one is a member selected from the group: DSPE; DSPE-PEG-maleimide; DSPE-PEG-FITC; HSPC; HSPC-PEG; cholesterol; cholesterol-PEG; and cholesterol-maleimide;

[21] the liposome composition according to any of [1]-[20], wherein the liposome comprises oxidized phospholipids, optionally wherein the phospholipids are a member selected from the group consisting of phosphatidylserines, phosphatidylinositols, phosphatidylethanolamines, phosphatidylcholines and 1-palmytoyl-2-arachidonoyl-sn-glycero-2-phosphate;

[22] the liposome composition according to any of [1]-[20], wherein the liposome comprises oxidized 1-palmitoyl-2-arachidonoyl-sn-glycero-3-phosphorylchloine (OxPAPC), optionally wherein the oxPAPCs are epoxyisoprostane-containing phospholipids;

[23] the liposome composition of [22], wherein the oxPAPC is 1-palmitoyl-2-(5,6-epoxyisoprostane E2)-sn-glycero-3-phosphocholine (5,6-PEIPC), 1-palmitoyl-2-(epoxy-cyclo-pentenone)-sn-glycero-3-phosphorylcholine (PECPC) and/or 1-palmitoyl-2-(epoxy-isoprostane E2)-sn-glycero-4-phosphocholine (PEIPC);

[24] the liposome composition according to any of [1]-[23], wherein the liposome is anionic or neutral;

[25] the liposome composition according to any of [1-[24], wherein the liposome has a zeta potential that is less than or equal to zero;

[26] the liposome composition of [25], wherein the liposome has a zeta potential that is between 0 to −150 mV or between −30 to −50 mV;

[27] the liposome composition according to any of [1]-[23], wherein the liposome has a zeta potential that is greater than zero;

[28] the liposome composition of [27], wherein the liposome has a zeta potential that is between 1 and 100 mV, between 5 to 60 mV, or between 10 to 50 mV;

[29] the liposome composition according to any of [1]-[23], [27], or [28], wherein the liposome is cationic;

[30] the liposome composition according to any of [1]-[29], wherein the pH of the internal phase of the liposome is between [25] and [75]

[31] the liposome composition of [30], wherein the pharmaceutically acceptable carrier comprises citrate buffer at a concentration of between 5 to 200 mM and a pH of between 2]8 to 6 or a total concentration of sodium acetate and calcium acetate of between 50 mM to 500 mM;

[32] the liposome composition according to any of [1]-[31], wherein the liposome internal phase comprises trehalose;

[33] the liposome composition of [32], wherein the liposome comprises 5% to 20% weight of trehalose;

[34] the liposome composition according to any of [1]-[33], which further comprises a targeting moiety attached to one or both of a PEG and the exterior of the liposome, and wherein the targeting moiety has a specific affinity for a surface antigen on a target cell of interest;

[35] the liposome composition of [34], wherein the targeting moiety is attached to one or both of the PEG and the exterior of the liposome by a covalent bond;

[36] the liposome composition according to [34] or [35], wherein the targeting moiety is a polypeptide;

[37] the liposome composition according to any of [34]-[36], wherein the targeting moiety is an antibody or a fragment of an antibody;

[38] the liposome composition according to any of [34]-[37], wherein the targeting moiety binds the surface antigen with an equilibrium dissociation constant (Kd) in a range of $0.5 \times 10^{-10}$ to $10 \times 10^{-6}$ as determined using BIACORE® analysis;

[39] the liposome composition according to any of [34]-[38], wherein the targeting moiety specifically binds one or more folate receptors selected from the group: folate receptor alpha (FR-α), folate receptor beta (FR-β), and folate receptor delta (FR-δ);

[40] the liposome composition according to any of [34]-[39], wherein the targeting moiety comprises one or more members selected from the group: an antibody, a humanized antibody, an antigen binding fragment of an antibody, a single chain antibody, a single-domain antibody, a bi-specific antibody, a synthetic antibody, a pegylated antibody, and a multimeric antibody;

[41] the liposome composition according to any of [34]-[40], wherein each PEGylated liposome comprises from 30 to 500 targeting moieties;

[42] the liposome composition according to any of [1]-[33], wherein the liposome does not comprise a targeting moiety attached to one or both of a PEG and the exterior of the liposome;

[43] the liposome composition of [41], wherein each PEGylated liposome comprises from 30 to 200 targeting moieties;

[44] the liposome composition according to any of [1]-[43], wherein the liposome further comprises a second complex formed by a therapeutic agent or a salt thereof, and one or more polylglutamate molecules or a cyclodextrin;

[45] the liposome composition of [44], wherein the therapeutic agent of the second complex is gemcitabine or doxorubicin, or a salt thereof,

[46] the liposome composition according to [44] or [45], wherein the second complex comprises cyclodextrin and wherein the cyclodextrin of the second complex is a derivatized or underivatized cyclodextrin;

[47] the liposome composition of [46], wherein the cyclodextrin of the second complex is a derivatized beta-cyclodextrin;

[48] the liposome composition of [47], wherein the derivatized beta-cyclodextrin is a hydroxypropyl beta-cyclodextrin (HP-beta-CD), or a sulfobutyl ether beta-cyclodextrin (SBE)-beta-CD;

[49] the liposome composition according to any of [46]-[48], wherein the cyclodextrin of the second complex is a derivatized beta-cyclodextrin comprising:
(a) 1, 2, 3, 4, 5, 6, or more 2-hydroxylpropyl-3- group substitutions of hydroxy groups; or
(b) 1, 2, 3, 4, 5, 6, or more sulfoalkyl ether group substitutions of hydroxy groups;

[50] the liposome composition of [49], wherein the cyclodextrin of the second complex is a derivatized beta-cyclodextrin comprising 1, 2, 3, 4, 5, 6, or more sulfobutyl ether group substitutions of hydroxy groups;

[51] the liposome composition according to any of [44]-[50], wherein the cyclodextrin of the second complex is a derivatized beta-cyclodextrin of Formula III:

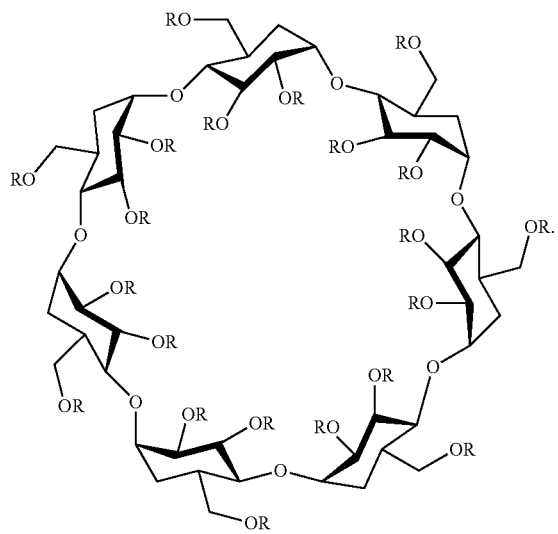

wherein R equals:
(a) $(H)_{21-X}$ or $(-(CH_2)_4-SO_3Na)_x$, and x=1.0-10.0, 1.0-5.0, 6.0-7.0 or 8.0-10.0;
(b) $(H)_{21-X}$ or $(-(CH_2CH(OH)CH_3)_x$, and x=1.0-10.0, 1.0-5.0, 6.0-7.0 or 8.0-10.0;
(c) $(H)_{21-X}$ or $(sulfoalkyl\ ether)_x$, and x=1.0-10.0, 1.0-5.0, 6.0-7.0 or 8.0-10.0; or
(d) $(H)_{21-X}$ or $(-(CH_2)_4-SO_3Na)_x$, and x=1.0-10.0, 1.0-5.0, 6.0-7.0 or 8.0-10.0;

[52] the liposome composition according to any of [44]-[51], wherein the cyclodextrin of the second complex is a derivatized cyclodextrin of Formula I:

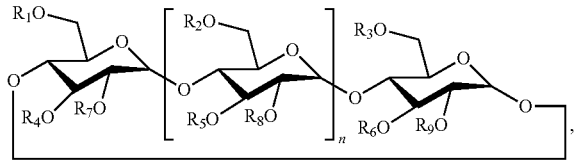

wherein: n is 4, 5, or 6;
wherein $R_1$, $R_2$, $R_3$, $R_4$, $R_5$, $R_6$, $R_7$, $R_8$, and $R_9$ are each, independently, —H, a straight chain or branched $C_1$-$C_8$-alkylene group, a 2-hydroxylpropyl-3- group; or an optionally substituted straight-chain or branched $C_1$-$C_6$ group, wherein at least one of $R_1$, $R_2$, $R_3$, $R_4$, $R_5$, $R_6$, $R_7$, $R_8$ and $R_9$ is a straight-chain or branched $C_1$-$C_8$-alkylene group or a 2-hydroxylpropyl-3- group;

[53] the liposome composition according to any of [44]-[51], wherein the cyclodextrin of the second complex is a derivatized cyclodextrin of formula II:

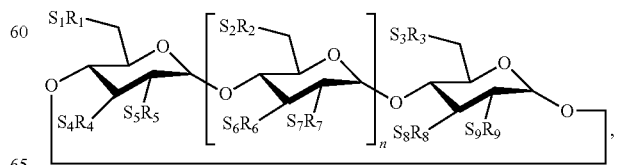

wherein: n is 4, 5, or 6;

wherein $R_1$, $R_2$, $R_3$, $R_4$, $R_5$, $R_6$, $R_7$, $R_8$, and $R_9$ are each, independently, —O— or a —O—$(C_2$-$C_6$ alkylene)-$SO_3^-$ group; wherein at least one of $R_1$ and $R_2$ is independently a —O—$(C_2$-$C_6$ alkylene)-$SO_3^-$ group; and $S_1$, $S_2$, $S_3$, $S_4$, $S_5$, $S_6$, $S_7$, $S_8$, and $S_9$ are each, independently, a —H or a pharmaceutically acceptable cation;

[54] the liposome composition of [53], wherein the pharmaceutically acceptable cation is selected from: an alkali metal such as $Li^+$, $Na^+$, or $K^+$; an alkaline earth metal such as $Ca^{+2}$, or $Mg^{+2}$ and ammonium ions and amine cations such as the cations of $(C_1$-$C_6)$-alkylamines, piperidine, pyrazine, $(C_1$-$C_6)$-alkanolamine, and $(C_4$-$C_8)$-cycloalkanolamine;

[55] the liposome composition according to any of [46]-[54], wherein each liposome comprises between 100 to 100,000 of the second complex formed by the therapeutic agent or a salt thereof, and the cyclodextrin;

[56] the liposome composition according to any of [46]-[55], wherein the cyclodextrin of the second complex is different from the cyclodextrin of the platinum-based chemotherapeutic agent complex;

[57] the liposome composition according to any of [46]-[55], wherein the cyclodextrin of the second complex is the same as the cyclodextrin of the platinum-based chemotherapeutic agent complex;

[58] the liposome composition according to any of [1]-[57], further comprising one or more of an immunostimulatory agent, a detectable marker and a maleimide, wherein the immunostimulatory agent, the detectable marker or the maleimide is attached to the PEG or the exterior of the liposome;

[59] the liposome composition of [58], wherein immunostimulating agent is at least one is a member selected from the group: a protein immunostimulating agent; a nucleic acid immunostimulating agent; a chemical immunostimulating agent; a hapten; and an adjuvant;

[60] the liposome composition according to [58] or [59], wherein the immunostimulating agent is at least one selected from the group: a fluorescein; a fluorescein isothiocyanate (FITC); a DNP; a beta glucan; a beta-1,3-glucan; and a beta-1,6-glucan;

[61] the liposome composition according to [58]-[60], wherein the immunostimulatory agent and the detectable marker is the same;

[62] the liposome composition of [59], which comprises a hapten;

[63] the liposome composition of [62], wherein the hapten comprises one or more of fluorescein or Beta 1,6-glucan;

[64] the liposome composition according to any of [1]-[63], which further comprises at least one cryoprotectant selected from the group consisting of mannitol; trehalose; sorbitol; and sucrose;

[65] the composition according to any of [1]-[64], which is in unit dosage form;

[66] the liposome composition according to any of [1]-[65] for use in the treatment of disease;

[67] Use of the liposome composition according to any of [1]-[65], in the manufacture of a medicament for the treatment of disease;

[68] a method of killing a hyperproliferative cell comprising contacting a hyperproliferative cell with the liposome composition according to any of [1]-[65]

[69] the method of [68], wherein the hyperproliferative cell is a cancer cell;

[70] a method for treating or preventing disease in a subject needing such treatment or prevention, the method comprising administering an effective amount of the liposome composition according to any of [1]-[65] to a subject in need thereof;

[71] a method for treating cancer in a subject, comprising administering an effective amount of a liposome composition according to any of [1]-[65] to a subject having or at risk of having cancer;

[72] the method of [71], wherein the cancer is a member selected from the group: lung cancer, pancreatic cancer, breast cancer, ovarian cancer, prostate cancer, head and neck cancer, gastric cancer, gastrointestinal cancer, colorectal cancer, esophageal cancer, cervical cancer, liver cancer, kidney cancer, biliary duct cancer, gallbladder cancer, bladder cancer, sarcoma (e.g., osteosarcoma), brain cancer, central nervous system cancer, and melanoma; and a hematologic malignancy such as for example, a leukemia, a lymphoma and other B cell malignancies, myeloma and other plasma cell dyscrasias;

[73] a method of delivering a liposome composition to a tumor expressing an antigen on its surface, the method comprising: administering the liposome composition according to any of [34]-[41] or [43]-[65] to a subject having a tumor expressing the antigen bound by the liposome targeting moiety in an amount to deliver a therapeutically effective dose of the liposome composition to the tumor;

[74] a method for treating cancer that comprises administering an effective amount of the liposome composition according to any of [34]-[41] or [43]-[65] to a subject having or at risk of having a cancer cell that expresses on its surface the antigen bound by the liposome targeting moiety;

[75] a maintenance therapy that comprises administering an effective amount of the liposome composition of any of [1]-[65] to a subject that is undergoing or has undergone cancer therapy;

[76] the method according to any of [70]-[75], wherein the administration is parenteral;

[77] the method of [76], wherein the administration is intravenous; and/or

[78] a pharmaceutical composition comprising the liposome composition according to any of [1]-[65].

BRIEF DESCRIPTION OF FIGURES

FIG. 1 provides exemplary L-gamma polyglutamated antifolates.

FIG. 2 provides exemplary alpha and D-gamma polyglutamated antifolates.

FIGS. 3A and 3B depict the formation and dissolution of cisplatin complexes with poly gamma glutamic acid (FIG. 3A) and poly alpha L-glutamic acid (FIG. 3B).

DETAILED DESCRIPTION

Figure 3B:
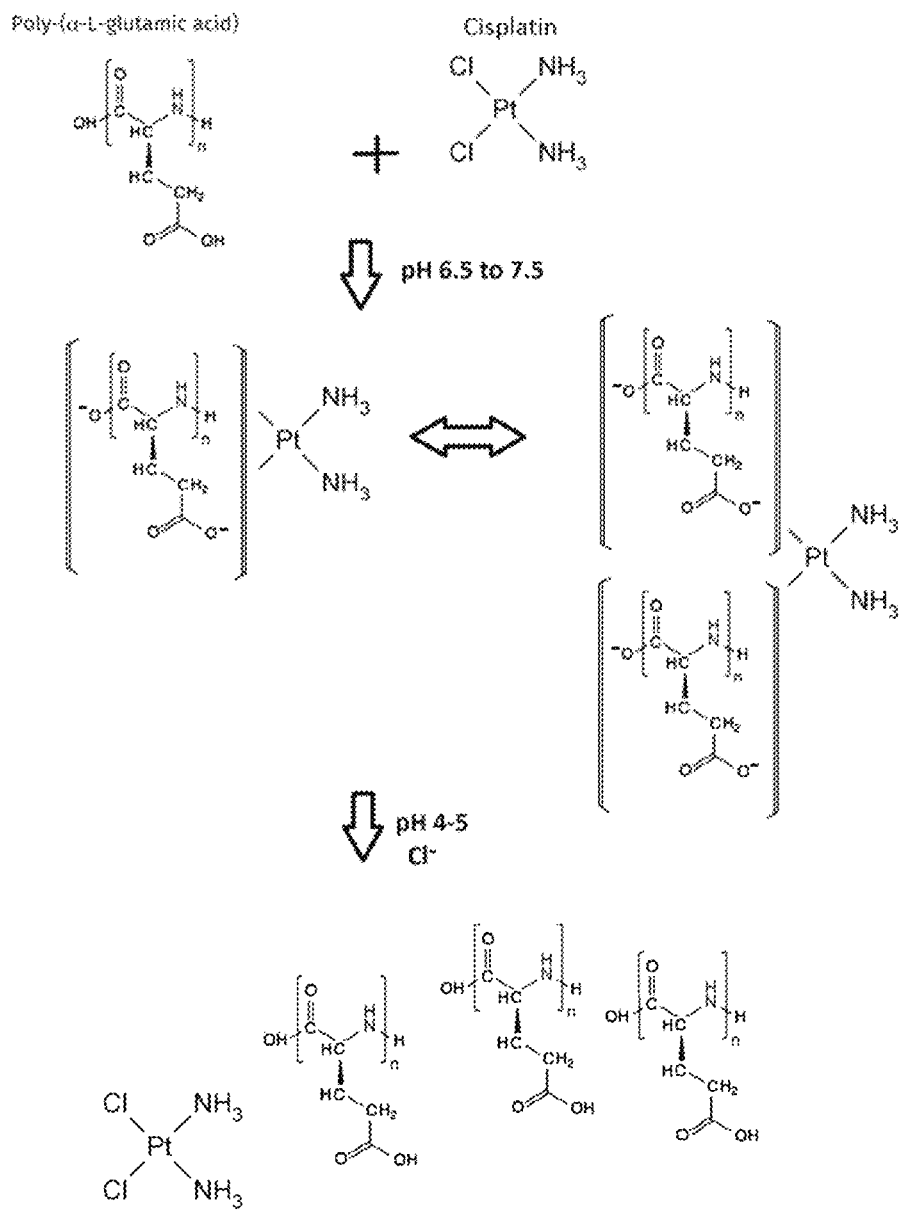

The disclosure generally relates to compositions comprising therapeutic agent complexes and to methods of making and using the compositions. In particular embodiments, the disclosure provides compositions comprising platinum-based drug complexes and to methods of making and using these compositions. In some embodiments, the disclosure provides a composition comprising a complex of a therapeutic agent such as a platinum-based drug therapeutic agent and one or more polyglutamate molecules. In some embodiments, the disclosure provides a composition comprising a complex of a therapeutic agent such as a platinum-based drug therapeutic agent and cyclodextrin. Methods of making and using the disclosed compositions to treat diseases such as cancer are also provided, as are kits containing the compositions.

(a) Definitions

Unless defined otherwise, all technical and scientific terms used herein have the same meaning as commonly understood by one of ordinary skill in the art to which the disclosure pertains.

It is understood that wherever embodiments, are provided herein with the language "comprising" otherwise analogous embodiments, described in terms of "containing" "consisting of" and/or "consisting essentially of" are also provided. However, when used in the claims as transitional phrases, each should be interpreted separately and in the appropriate legal and factual context (e.g., in claims, the transitional phrase "comprising" is considered more of an open-ended phrase while "consisting of" is more exclusive and "consisting essentially of" achieves a middle ground).

As used herein, the singular form "a", "an", and "the", includes plural references unless it is expressly stated or is unambiguously clear from the context that such is not intended.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

The term "non-natural amino acid" refers to an amino acid that is not a proteinogenic amino acid, or a post-translationally modified variant thereof. In particular, the term refers to an amino acid that is not one of the 20 common amino acids or pyrrolysine or selenocysteine, or post-translationally modified variants thereof.

The terms "polyglutamate", polyglutamated", or variations thereof, as used herein, refer to a molecule comprising at least one chain of 2 or more linked glutamyl groups. Polyglutamate chains can be linear or branched. In some embodiments, the polyglutamate comprises 2, 3, 4, 5, 6, 2-10, 4-6, or more than 5 glutamyl groups. Linear polyglutamate chains can contain for example, glutamyl groups containing either an alpha carboxyl group or a gamma carboxyl group linkage. The term gamma linkage as it relates to a polyglutamate, refers to a peptide bond between the amino group of a first glutamyl residue and the carboxyl group at the gamma carbon of the side chain of a second glutamyl residue in the polyglutamate. The term alpha linkage as it relates to a polyglutamate, refers to a peptide bond between the amino group of a first glutamyl residue and the carboxyl group at the alpha carbon of the side chain of a second glutamyl residue in the polyglutamate. The glutamyl groups in a polyglutamate can contain alpha linkages, gamma linkages, or a combination of alpha and gamma linkages. In some embodiments, the glutamyl groups in the polyglutamate contain only alpha linkages. In some embodiments, the glutamyl groups in the polyglutamate contain only gamma linkages. In embodiments, each of the glutamyl groups of a polyglutamate is an L isomer. The polyglutamates can contain L glutamyl isomers, D, glutamyl isomers, or a combination thereof. In particular embodiments, each of the glutamyl groups of the polyglutamate is an L isomer. In some embodiments, each of the glutamyl groups of the polyglutamate is an L isomer.

The term "polyglutamated antifolate" and iterations thereof, refers to an antifolate molecule that comprises at least one glutamyl group in addition to the glutamyl group of the antifolate (i.e., Antifolate-[glutamyl]n, where -[glutamyl]n refers to the glutamates attached to the antifolate, n is the number of attached glutamates, and wherein n is greater than 1). Reference to the number of glutamyl groups in an antifolate herein takes into account the glutamyl group of antifolate or folate. For example, an Antifolate-[glutamyl]n composition where n=5 is referred to herein as hexaglutamated Antifolate or Antifolate hexaglutamate. See, e.g., FIG. 1 and FIG. 2.

The term "polyglutamated folate" and iterations thereof, refers to a folate molecule that comprises at least one glutamyl group in addition to the glutamyl group of the folate (i.e., Folate-(glutamyl)n, where -[glutamyl]n refers to the glutamates attached to the folate, n is the number of attached glutamates, and wherein n is greater than 1).

Unless otherwise explicitly indicated herein, the provided therapeutic agent complexes (e.g., platinum-polyglutamate complexes and platinum-cyclodextrin complexes) are non-covalent complexes wherein the bonds between the components of the complex are non-covalent bonds, i.e., weak bonds such as H-bonds and Van der Waals forces. The term "complex" as used herein includes, but is not limited to, an inclusion complex. The term "inclusion complex" as used herein refers to inclusion complexes wherein the platinum agent is surrounded by and entrapped within a cyclodextrin, and to partial inclusion complexes wherein the platinum agent is surrounded partially by cyclodextrin.

As use herein, the term "isolated" refers to a composition which is in a form not found in nature. For example, isolated polyglutamate (e.g., gamma-L-polyglutamate (L-γPGA) and alpha-L-polyglutamate (L-αPGA) compositions) include those which have been purified to a degree that they are no longer in a form in which they are found in nature. In some embodiments, the polyglutamate (e.g., alpha L-γPGA or L-αPGA) which is isolated is substantially pure. Isolated compositions will be free or substantially free of material with which they are naturally associated such as other cellular components such as proteins and nucleic acids with which they may potentially be found in nature, or the environment in which they are prepared (e.g., cell culture). The alpha polyglutamated compositions may be formulated with diluents or adjuvants and still for practical purposes be isolated—for example, polyglutamate compositions will normally be mixed with pharmaceutically acceptable carriers or diluents when used in diagnosis or therapy. In some embodiments, the polyglutamate compositions (e.g., alpha L-γPGA or L-αPGA) and delivery vehicles such as liposomes containing the polyglutamates contain less than 1% or less than 0.1% undesired DNA or protein content. In some embodiments, the polyglutamate compositions (e.g., alpha L-γPGA or L-αPGA) are "isolated."

The term "targeting moiety" is used herein to refer to a molecule that provides an enhanced affinity for a selected target, e.g., a cell, cell type, tissue, organ, region of the body, or a compartment, e.g., a cellular, tissue or organ compartment. The targeting moiety can comprise a wide variety of entities. Targeting moieties can include naturally occurring molecules, or recombinant or synthetic molecules. In some embodiments, the targeting moiety is an antibody, antigen-binding antibody fragment, bispecific antibody or other antibody-based molecule or compound. In some embodiments, the targeting moiety is an aptamer, avimer, a receptor-binding ligand, a nucleic acid, a biotin-avidin binding pair, a peptide, protein, carbohydrate, lipid, vitamin, toxin, a component of a microorganism, a hormone, a receptor ligand or any derivative thereof. Other targeting moieties are known in the art and are encompassed by the disclosure.

The terms "specific affinity" or "specifically binds" mean that a targeting moiety such as an antibody or antigen binding antibody fragment, reacts or associates more frequently, more rapidly, with greater duration, with greater affinity, or with some combination of the above to the epitope, protein, or target molecule than with alternative substances, including proteins unrelated to the target epitope. Because of the sequence identity between homologous proteins in different species, specific affinity can, in several embodiments, include a binding agent that recognizes a protein or target in more than one species. Likewise, because of homology within certain regions of polypeptide sequences of different proteins, the term "specific affinity" or "specifically binds" can include a binding agent that recognizes more than one protein or target. It is understood that, in certain embodiments, a targeting moiety that specifically binds a first target may or may not specifically bind a second target. As such, "specific affinity" does not necessarily require (although it can include) exclusive binding, e.g., binding to a single target. Thus, a targeting moiety may, in certain embodiments, specifically bind more than one target. In certain embodiments, multiple targets may be bound by the same targeting moiety.

The terms "epitope" and "antigenic determinant" are used interchangeably herein and refer to that portion of an antigen capable of being recognized and specifically bound by a particular antibody or binding moiety. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

Expressions like "binding affinity for a target", "binding to a target" and analogous expressions known in the art refer to a property of a targeting moiety which may be directly measured through the determination of the affinity constants, e.g., the amount of targeting moiety that associates and dissociates at a given antigen concentration. Different methods can be used to characterize the molecular interaction, such as, but not limited to, competition analysis, equilibrium analysis and microcalorimetric analysis, and real-time interaction analysis based on surface plasmon resonance interaction (for example using a BIACORE® instrument). These methods are well-known to the skilled person and are described, for example, in Neri et al., Tibtech 14:465-470 (1996), and Jansson et al., J. Biol. Chem. 272:8189-8197 (1997).

The term "delivery vehicle" refers generally to any compositions that acts to assist, promote or facilitate entry of the provided therapeutic agent complexes (e.g., platinum-polyglutamate complexes and platinum-cyclodextrin complexes) into a cell. Such delivery vehicles are known in the art and include, but are not limited to, liposomes, liposheres, polymers (e.g., polymer-conjugates), peptides, proteins such as antibodies (e.g., immunoconjugates, such as Antibody Drug Conjugates (ADCs)) and antigen binding antibody fragments and derivatives thereof), cellular components, cyclic oligosaccharides (e.g., cyclodextrins), micelles, microparticles (e.g., microspheres), nanoparticles (e.g., lipid nanoparticles, biodegradable nanoparticles, and core-shell nanoparticles), hydrogels, lipoprotein particles, viral sequences, viral material, or lipid or liposome formulations, and combinations thereof. The delivery vehicle can be linked directly or indirectly to a targeting moiety. In some examples, the targeting moiety is selected from among a macromolecule, a protein, a peptide, a monoclonal antibody or a fatty acid lipid.

A "subject" refers to a human or vertebrate mammal including but not limited to a dog, cat, horse, goat and primate, e.g., monkey. Thus, the invention can also be used to treat diseases or conditions in non-human subjects. For instance, cancer is one of the leading causes of death in companion animals (i.e., cats and dogs). In some embodiments, of the invention, the subject is a human. In this disclosure, the term "subject" and "patient" is used interchangeably and has the same meaning. It is preferred generally that a maximum dose be used, that is, the highest safe dose according to sound medical judgment.

As used herein an "effective amount" refers to a dosage of an agent sufficient to provide a medically desirable result. The effective amount will vary with the desired outcome, the particular condition being treated or prevented, the age and physical condition of the subject being treated, the severity of the condition, the duration of the treatment, the nature of the concurrent or combination therapy (if any), the specific route of administration and like factors within the knowledge and expertise of the health practitioner. An "effective amount" can be determined empirically and in a routine manner, in relation to the stated purpose. In the case of cancer, the effective amount of an agent may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can be measured for example, by assessing the duration of survival, duration of progression free survival (PFS), the response rates (RR), duration of response, and/or quality of life.

The terms "hyperproliferative disorder", "hyperproliferative disease", "proliferative disorder", and "proliferative disease", are used interchangeably herein to pertain to an unwanted or uncontrolled cellular proliferation of excessive or abnormal cells which is undesired, such as, neoplastic or hyperplastic growth, whether in vitro or in vivo. In some embodiments, the proliferative disease is cancer or tumor disease (including benign or cancerous) and/or any metastases, wherever the cancer, tumor and/or the metastasis is located. In some embodiments, the proliferative disease is a benign or malignant tumor. In some embodiments, the proliferative disease is a non-cancerous disease. In some embodiments, the proliferative disease is a hyperproliferative condition such as hyperplasias, fibrosis (especially pulmonary, but also other types of fibrosis, such as renal fibrosis), angiogenesis, psoriasis, atherosclerosis and smooth muscle proliferation in the blood vessels, such as stenosis or restenosis following angioplasty.

"Cancer," "tumor," or "malignancy" are used as synonymous terms and refer to any of a number of diseases that are characterized by uncontrolled, abnormal proliferation of cells, the ability of affected cells to spread locally or through the bloodstream and lymphatic system to other parts of the body (metastasize) as well as any of a number of characteristic structural and/or molecular features. "Tumor," as used herein refers to all neoplastic cell growth and proliferation, whether malignant or benign, and all pre-cancerous and cancerous cells and tissues. A "cancerous tumor," or "malignant cell" is understood as a cell having specific structural properties, lacking differentiation and being capable of invasion and metastasis. A cancer that can be treated using a platinum-based chemotherapeutic agent provided herein includes without limitation, a non-hematologic malignancy including such as for example, lung cancer, pancreatic cancer, breast cancer, ovarian cancer, prostate cancer, head and neck cancer, gastric cancer, gastrointestinal cancer, colorectal cancer, esophageal cancer, cervical cancer, liver cancer, kidney cancer, biliary duct cancer, gallbladder cancer, bladder cancer, sarcoma (e.g., osteosarcoma), brain cancer, central nervous system cancer, and melanoma; and a hematologic malignancy such as for example, a leukemia, a lymphoma and other B cell malignancies, myeloma and other plasma cell dyscrasias. Other types of cancer and tumors that may be treated using a platinum-based chemotherapeutic agent provided herein or otherwise known in the art. The terms "cancer," "cancerous," "cell proliferative disorder," "proliferative disorder," and "tumor" are not mutually exclusive as referred to herein.

Terms such as "treating," or "treatment," or "to treat" refer to both (a) therapeutic measures that cure, slow down, lessen symptoms of, and/or halt progression of a diagnosed pathologic condition or disorder and (b) prophylactic or preventative measures that prevent and/or slow the development of a targeted disease or condition. Thus, subjects in need of treatment include those already with the cancer, disorder or disease; those at risk of having the cancer or condition; and those in whom the infection or condition is to be prevented. Subjects are identified as "having or at risk of having" cancer, an infectious disease, a disorder of the immune system, a hyperproliferative disease, or another disease or disorder referred to herein using well-known medical and diagnostic techniques. In certain embodiments, a subject is successfully "treated" according to the methods provided herein if the subject shows, e.g., total, partial, or transient amelioration or elimination of a symptom associated with the disease or condition (e.g., cancer). In specific embodiments, the terms treating," or "treatment," or "to treat" refer to the amelioration of at least one measurable physical parameter of a proliferative disorder, such as growth of a tumor, not necessarily discernible by the patient. In other embodiments, the terms treating," or "treatment," or "to treat" refer to the inhibition of the progression of a proliferative disorder, either physically by, e.g., stabilization of a discernible symptom, physiologically by, e.g., stabilization of a physical parameter, or both. In other embodiments, the terms treating," or "treatment," or "to treat" refer to the reduction or stabilization of tumor size, tumor cell proliferation or survival, or cancerous cell count. Treatment can be with a platinum-based chemotherapeutic agent, alone or in combination with an additional therapeutic agent. As used herein the terms "treat", "treating" and "treatment" include administering the composition prior to the onset of clinical symptoms of a disease state/condition so as to prevent the development of any symptom, as well as administering the composition after the onset of one or more clinical symptoms of a disease state/condition so as to reduce or eliminate any such symptom, aspect or characteristic of the disease state/condition. Such treating need not be absolute to be useful.

"Subject" and "patient," and "animal" are used interchangeably and refer to mammals such as human patients and non-human primates, as well as experimental animals such as rabbits, rats, and mice, and other animals. Animals include all vertebrates, e.g., mammals and non-mammals, such as chickens, amphibians, and reptiles. "Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and other members of the class Mammalia known in the art. In a particular embodiment, the patient is a human.

The terms "treatment of a proliferative disorder", "treatment of a hyperproliferative disorder" and iterations thereof, is used herein to include maintaining or decreasing tumor size, inducing tumor regression (either partial or complete), inhibiting tumor growth, and/or increasing the life span of a subject having the proliferative disorder. In one embodiment, the proliferative disorder is a solid tumor. Such tumors include, for example, lung cancer, pancreatic cancer, breast cancer, ovarian cancer, prostate cancer, head and neck cancer, gastric cancer, gastrointestinal cancer, colorectal cancer, esophageal cancer, cervical cancer, liver cancer, kidney cancer, biliary duct cancer, gallbladder cancer, bladder cancer, sarcoma (e.g., osteosarcoma), brain cancer, central nervous system cancer, and melanoma; and a hematologic malignancy such as for example, a leukemia, a lymphoma and other B cell malignancies, myeloma and other plasma cell dyscrasias.

The term "therapeutic agent" is used herein to refer to an agent or a derivative thereof that can interact with a hyperproliferative cell such as a cancer cell or an immune cell, thereby reducing the proliferative status of the cell and/or killing the cell. Examples of therapeutic agents include, but are not limited to, chemotherapeutic agents, cytotoxic agents, platinum-based chemotherapeutic agents (e.g., cisplatin and oxaliplatin), taxanes (e.g., TAXOL®), etoposide, alkylating agents (e.g., cyclophosphamide, ifosamide), metabolic antagonists (e.g., methotrexate (MTX), 5-fluorouracil gemcitabine, or a derivative thereof), antitumor antibiotics (e.g., mitomycin, doxorubicin), plant-derived antitumor agents (e.g., vincristine, vindesine, TAXOL®). Such agents may further include, but are not limited to, the anticancer agents trimetrexate, temozolomide, raltitrexed, S-(4-Nitrobenzyl)-6-thioinosine (NBMPR), 6-benzyguanidine (6-BG), bis-chloronitrosourea (BCNU) and camptothecin, or a therapeutic derivative of any thereof. Additional examples of therapeutic agents that may be suitable for use in accordance with the disclosed methods include, without limitation, anti-restenosis, pro- or anti-proliferative, anti-inflammatory, anti-neoplastic, antimitotic, anti-platelet, anti-coagulant, antifibrin, antithrombin, cytostatic, antibiotic and other anti-infective agents, anti-enzymatic, anti-metabolic, angiogenic, cytoprotective, angiotensin converting enzyme (ACE) inhibiting, angiotensin II receptor antagonizing and/or cardioprotective agents. "Therapeutic agents" also refer to salts, acids, and free based forms of the above agents.

As used herein, the term "chemotherapeutic agent" when used in relation to cancer therapy, refers to any agent that results in the death of cancer cells or inhibits the growth or spread of cancer cells. Examples of such chemotherapeutic agents include alkylating agents, antibiotics, antimetabolitic agents, plant-derived agents, and hormones. In some embodiments, the chemotherapeutic agent is cisplatin. In some embodiments, the chemotherapeutic agent is oxaliplatin. In other embodiments, the chemotherapeutic agent is gemcitabine. In other embodiments, the chemotherapeutic agent is doxorubicin.

The term "antimetabolite" is used herein to refer to a therapeutic agent that inhibits the utilization of a metabolite or a prodrug thereof. Examples of antimetabolites include methotrexate, pemetrexed, 5-fluorouracil, 5-fluorouracil prodrugs such as capecitabine, 5-fluorodeoxyuridine monophosphate, cytarabine, cytarabine prodrugs such as nelarabine, 5-azacytidine, gemcitabine, mercaptopurine, thioguanine, azathioprine, adenosine, pentostatin, erythrohydroxynonyladenine, and cladribine. Anti-metabolites useful for practicing the disclosed methods include nucleoside analogs, including a purine or pyrimidine analogs. In some embodiments, platinum based chemotherapeutic agents are used in combination with an antimetabolite selection from the group consisting of fluoropyrimidine 5-fluorouracil, 5-fluoro-2'-deoxycytidine, cytarabine, gemcitabine, troxacitabine, decitabine, Azacytidine, pseudoisocytidine, Zebularine, Ancitabine, Fazarabine, 6-azacytidine, capecitabine, $N^4$-octadecyl-cytarabine, elaidic acid cytarabine, fludarabine, cladribine, clofarabine, nelarabine, forodesine, and pentostatin, or a derivative thereof. In one example, the nucleoside analog is a substrate for a nucleoside deaminase that is adenosine deaminase or cytidine deaminase. In some examples, the nucleoside analog is selected from among fludarabine, cytarabine, gemcitabine, decitabine and azacytidine or a derivative thereof. In certain embodiments, the antimetabolite is 5-fluorouracil.

As used herein, a "taxane" or a "taxane-based agent" is an anti-cancer agent that interferes with or disrupts microtubule stability, formation and/or function. Taxane agents include paclitaxel and docetaxel as well as derivatives thereof, wherein the derivatives function against microtubules by the same mode of action as the taxane from which they are derived. In certain embodiments, the taxane is paclitaxel or docetaxel, or a pharmaceutically acceptable salt, acid, or derivative of paclitaxel or docetaxel. In certain embodiments, the taxane is paclitaxel (TAXOL®), docetaxel (TAXOTERE®), albumin-bound paclitaxel (nab-paclitaxel; ABRAXANE®), DHA-paclitaxel, or PG-paclitaxel.

The term "carrier" denotes an organic or inorganic ingredient, natural or synthetic, with which liposome compositions are combined to facilitate administration. The components of the pharmaceutical compositions are comingled in a manner that precludes interaction that would substantially impair their desired pharmaceutical efficiency. Suitable buffering agents include acetic acid and a salt (1-2% W/V); citric acid and a salt (1-3% W/V); boric acid and a salt (0.5-2.5% W/V); and phosphoric acid and a salt (0.8-2% W/V). Suitable preservatives include benzalkonium chloride (0.003-0.03% W/V); chlorobutanol (0.3-0.9% W/V); and parabens (0.01-0.25% W/V).

The term "pharmaceutically-acceptable carrier" and "pharmaceutically acceptable carrier" refers to an ingredient in a pharmaceutical formulation, other than an active ingredient, which is nontoxic to a subject. A pharmaceutically acceptable carrier includes, but is not limited to, a buffer, carrier, excipient, stabilizer, diluent, or preservative. Pharmaceutically-acceptable carriers can include for example, one or more compatible solid or liquid filler, diluents or encapsulating substances which are suitable for administration to a human or other subject.

The terms "platinum-based chemotherapeutic agent", "platinum-based agent", "platinum" and "platin", are used interchangeably herein to refer to an antineoplastic drug that is a coordination complex of platinum. Examples of platinum-based chemotherapeutic agents include without limitation, cisplatin, oxaliplatin, nedaplatin, heptaplatin, lobaplatin, stratoplatin, paraplatin, platinol, cycloplatin, dexormaplatin, spiroplatin picoplatin, triplatin, iproplatin, and oxaliplatin, zeniplatin, platinum-triamine complex; ormaplatin, dedaplatin, JM-216, 254-S, NK 121, CI-973, DWA 2114R, and NDDP.

The term "platinum-based chemotherapy" refers to therapy with one or more platinum-based chemotherapeutic agents, optionally in combination with one or more other therapeutic agents (e.g., chemotherapeutic agents, such as gemcitabine, doxorubicin, an antifolate, and a taxane).

In one embodiment, the disclosure provides a liposome composition comprising a liposome encapsulating a complex of a platinum-based chemotherapeutic agent or a salt thereof, and one or more polyglutamate molecules. In some embodiments, the liposome is pegylated. In some embodiments, the liposome composition comprises on ore more pharmaceutically acceptable carriers.

In some embodiments, the liposome composition comprises a liposome encapsulating a complex of cisplatin or a salt thereof, and one or more polyglutamate molecules; and one or more pharmaceutically acceptable carriers. In further embodiments, the liposome is pegylated.

In some embodiments, the liposome composition comprises a liposome encapsulating a complex of a cisplatin analog or a salt thereof, and one or more polyglutamate molecules.

In some embodiments, the liposome composition comprises a liposome encapsulating a complex of carboplatin or a salt thereof, and one or more polyglutamate molecules. In some embodiments, the liposome composition comprises a liposome encapsulating a complex of a complex of oxaliplatin or a salt thereof, and one or more polyglutamate molecules.

In some embodiments, the liposome composition comprises a liposome encapsulating a complex of a platinum-based chemotherapeutic agent and one or more polyglutamate molecules, wherein the platinum-based chemotherapeutic is selected from the group: nedaplatin, heptaplatin, and lobaplatin, or a salt thereof, and cyclodextrin; and one or more pharmaceutically acceptable carriers. In some embodiments, the platinum-based chemotherapeutic agent is nedaplatin. In some embodiments, the platinum-based chemotherapeutic agent is heptaplatin. In some embodiments, the platinum-based chemotherapeutic agent is lobaplatin.

In some embodiments, the liposome composition comprises a liposome encapsulating a complex of a platinum-based chemotherapeutic agent and one or more polyglutamate molecules, wherein the platinum-based chemotherapeutic is selected from the group: stratoplatin, paraplatin, platinol, cycloplatin, dexormaplatin, spiroplatin, picoplatin, triplatin, tetraplatin, iproplatin, ormaplatin, zeniplatin, platinum-triamine, enloplatin, JM-216, 254-S, NK 121, CI-973, DWA 2114R, NDDP, and dedaplatin. In some embodiments, the platinum-based chemotherapeutic agent is stratoplatin. In some embodiments, the platinum-based chemotherapeutic agent is paraplatin. In some embodiments, the platinum-based chemotherapeutic agent is platinol. In some embodiments, the platinum-based chemotherapeutic agent is cycloplatin. In some embodiments, the platinum-based chemotherapeutic agent is dexormaplatin. In some embodiments, the platinum-based chemotherapeutic agent is spiroplatin. In some embodiments, the platinum-based chemotherapeutic agent is picoplatin. In some embodiments, the platinum-based chemotherapeutic agent is triplatin. In some embodiments, the platinum-based chemotherapeutic agent is tetraplatin. In some embodiments, the platinum-based chemotherapeutic agent is iproplatin. In some embodiments, the platinum-based chemotherapeutic agent is ormaplatin. In some embodiments, the platinum-based chemotherapeutic agent is zeniplatin. In some embodiments, the platinum-based chemotherapeutic agent is picoplatin. In some embodiments, the platinum-based chemotherapeutic agent is triplatin. In some embodiments, the platinum-based chemotherapeutic agent is tetraplatin. In some embodiments, the platinum-based chemotherapeutic agent is iproplatin. In some embodiments, the platinum-based chemotherapeutic agent is ormaplatin. In some embodiments, the platinum-based chemotherapeutic agent is zeniplatin. In some embodiments, the platinum-based chemotherapeutic agent is platinum-triamine. In some embodiments, the platinum-based chemotherapeutic agent is enloplatin. In some embodiments, the platinum-based chemotherapeutic agent is JM-216. In some embodiments, the platinum-based chemotherapeutic agent is 254-S. In some embodiments, the platinum-based chemotherapeutic agent is NK 121. In some embodiments, the platinum-based chemotherapeutic agent is CI-973. In some embodiments, the platinum-based chemotherapeutic agent is DWA 2114R. In some embodiments, the platinum-based chemotherapeutic agent is NDDP. In some embodiments, the platinum-based chemotherapeutic agent is dedaplatin.

In another embodiment, the disclosure provides a liposome composition comprising a liposome encapsulating a complex of a platinum-based chemotherapeutic agent or a salt thereof, and a cyclodextrin. In some embodiments, the liposome is pegylated. In some embodiments, the liposome composition comprises on ore more pharmaceutically acceptable carriers.

In some embodiments, the liposome composition comprises a liposome encapsulating a complex of cisplatin or a salt thereof, and a cyclodextrin.

In some embodiments, the liposome composition comprises a liposome encapsulating a complex of a cisplatin analog or a salt thereof, and a cyclodextrin.

In some embodiments, the liposome composition comprises a liposome encapsulating a complex of carboplatin or a salt thereof, and a cyclodextrin In some embodiments, the liposome composition comprises a liposome encapsulating a complex of a complex of oxaliplatin or a salt thereof, and a cyclodextrin.

In some embodiments, the liposome composition comprises a liposome encapsulating a complex of a platinum-based chemotherapeutic agent and a cyclodextrin, wherein the platinum-based chemotherapeutic agent is selected from the group: nedaplatin, heptaplatin, and lobaplatin, or a salt thereof, and cyclodextrin; and one or more pharmaceutically acceptable carriers. In some embodiments, the platinum-based chemotherapeutic agent is nedaplatin. In some embodiments, the platinum-based chemotherapeutic agent is heptaplatin. In some embodiments, the platinum-based chemotherapeutic agent is lobaplatin.

In some embodiments, the liposome composition comprises a liposome encapsulating a complex of a platinum-based chemotherapeutic agent and a cyclodextrin, wherein the platinum-based chemotherapeutic agent is selected from the group: stratoplatin, paraplatin, platinol, cycloplatin, dexormaplatin, spiroplatin, picoplatin, triplatin, tetraplatin, iproplatin, ormaplatin, zeniplatin, platinum-triamine, enloplatin, JM-216, 254-S, NK 121, CI-973, DWA 2114R, NDDP, and dedaplatin. In some embodiments, the platinum-based chemotherapeutic agent is stratoplatin. In some embodiments, the platinum-based chemotherapeutic agent is paraplatin. In some embodiments, the platinum-based chemotherapeutic agent is platinol. In some embodiments, the platinum-based chemotherapeutic agent is cycloplatin. In some embodiments, the platinum-based chemotherapeutic agent is dexormaplatin. In some embodiments, the platinum-based chemotherapeutic agent is spiroplatin. In some embodiments, the platinum-based chemotherapeutic agent is picoplatin. In some embodiments, the platinum-based chemotherapeutic agent is triplatin. In some embodiments, the platinum-based chemotherapeutic agent is tetraplatin. In some embodiments, the platinum-based chemotherapeutic agent is iproplatin. In some embodiments, the platinum-based chemotherapeutic agent is ormaplatin. In some embodiments, the platinum-based chemotherapeutic agent is zeniplatin. In some embodiments, the platinum-based chemotherapeutic agent is platinum-triamine. In some embodiments, the platinum-based chemotherapeutic agent is enloplatin. In some embodiments, the platinum-based chemotherapeutic agent is JM-216. In some embodiments, the platinum-based chemotherapeutic agent is 254-S. In some embodiments, the platinum-based chemotherapeutic agent is NK 121. In some embodiments, the platinum-based chemotherapeutic agent is CI-973. In some embodiments, the platinum-based chemotherapeutic agent is DWA 2114R. In some embodiments, the platinum-based chemotherapeutic agent is NDDP. In some embodiments, the platinum-based chemotherapeutic agent is dedaplatin. In further embodiments, the liposome is pegylated.

Cisplatin is a potent anti-carcinogen that is widely used for various solid tumors; however, its clinical application is limited by its severe nephrotoxicity. It has been widely used because of its potent cytotoxic effects upon a variety of tumor types including testicular, ovarian, and cervical carcinoma. In some embodiments, the disclosure provides a method for treating cancer in a subject, comprising administering an effective amount of a liposome composition comprising a liposome encapsulating a complex of a platinum-based chemotherapeutic agent or a salt thereof, and (a) one or more polyglutamate molecules, or (b) cyclodextrin; to a subject having or at risk of having cancer. In some embodiments the platinum-based chemotherapeutic agent is cisplatin. In some embodiments the platinum-based chemotherapeutic agent is cisplatin a cispatin analoag. In some embodiments the cancer is a member selected from the group: lung cancer, pancreatic cancer, breast cancer, ovarian cancer, prostate cancer, head and neck cancer, gastric cancer, gastrointestinal cancer, colorectal cancer, esophageal cancer, cervical cancer, liver cancer, kidney cancer, biliary duct cancer, gallbladder cancer, bladder cancer, sarcoma (e.g., osteosarcoma), brain cancer, central nervous system cancer, and melanoma; and a hematologic malignancy such as for example, a leukemia, a lymphoma and other B cell malignancies, myeloma and other plasma cell dyscrasias. In further embodiments, the cancer is testicular cancer, ovarian cancer, or cervical carcinoma.

In some embodiments, the disclosure provides compositions such as liposome compositions, that comprise a complex of a therapeutic agent and a cyclodextrin. Cyclodextrins (CDs) are groups of cyclic oligosaccharides which have been shown to improve physicochemical properties of many drugs through formation of complexes. CDs are cyclic oligosaccharides composed of several D-glucose units linked by a-(1, 4) bonds. This cyclic configuration provides a hydrophobic internal cavity and gives the CDs a truncated cone shape. Many hydroxyl groups are situated on the edges of the ring which make the CDs both lipophilic and soluble in water. As a result, CDs are able to form complexes with a wide variety of hydrophobic agents, and thus change the physical-chemical properties of these complexed agents.

The terms "cyclodextrin" or "CD" unless otherwise specified herein, refer generally to a parent or derivatized cyclic oligosaccharide containing a variable number of ($\alpha$-1,4)-linked D-glucopyranoside units that is able to form a complex with a platinum-based agent, or another chemotherapeutic agent of interest (e.g., an antifolate, gemcitabine, and doxorubicin). Each cyclodextrin glucopyranoside subunit has secondary hydroxyl groups at the 2 and 3 positions and a primary hydroxyl group at the 6-position. The terms "parent," "underivatized," or "inert," cyclodextrin refer to a cyclodextrin containing D-glucopyranoside units having the basic formula $C_6H_{12}O_6$ and a glucose structure without any additional chemical substitutions (e.g., $\alpha$-cyclodextrin consisting of 6 D-glucopyranoside units, a $\beta$-cyclodextrin consisting of 7 D-glucopyranoside units, and a $\gamma$-cyclodextrin consisting of 8 D-glucopyranoside units). The physical and chemical properties of a parent cyclodextrin can be modified by derivatizing the hydroxyl groups with other functional groups. Any substance located within the cyclodextrin internal phase is said to be "complexed" with the cyclodextrin, or to have formed a complex (inclusion complex) with the cyclodextrin.

As used herein, there are no particular limitations on the cyclodextrin contained in the provided liposome compositions so long as the cyclodextrins can encapsulate a desired therapeutic agent, In particular embodiments, the cyclodextrins have been derivatized to bear ionizable (e.g., weakly basic and/or weakly acidic) functional groups to facilitate encapsulation by the liposomes.

Modifications of the hydroxyl groups of cyclodextrins, such as those facing away from the cyclodextrin interior phase, with ionizable chemical groups is known to facilitate the loading of cyclodextrins and therapeutic agents complexed with the cyclodextrins. In some embodiments, the cyclodextrins in the provided liposome compositions have at least 2, 3, 4, 5, 6, 6, 7, 8, 9, or 10 hydroxyl group substituted with an ionizable chemical group. The term "charged cyclodextrin" refers to a cyclodextrin having one or more of its hydroxyl groups substituted with a charged moiety. Such a moiety can itself be a charged group or it can comprise an organic moiety (e.g., a $C_1$-$C_6$ alkyl or $C_1$-$C_6$ alkyl ether moiety) substituted with one or more charged moieties.

In some embodiments, the "ionizable" or "charged" moieties of a CD derivative are weakly ionizable. Weakly ionizable moieties are those that are either weakly basic or weakly acidic. Weakly basic functional groups (W) have a pKa of between about 6.0-9.0, 6.5-8.5, 7.0-8.0, 7.5-8.0, and any range in between inclusive according to CH3-W. Similarly, weakly acidic functional groups (X) have a log dissociation constant (pKa) of between about 3.0-7.0, 4.0-6.5, 4.5-6.5, 5.0-6.0, 5.0-5.5, and any range in between inclusive according to CH3-X. Representative anionic moieties include, without limitation, carboxylate, carboxymethyl, succinyl, sulfonyl, phosphate, sulfoalkyl ether, sulphate carbonate, thiocarbonate, dithiocarbonate, phosphate, phosphonate, sulfonate, nitrate, and borate groups. Representative cationic moieties include, without limitation, amino, guanidine, and quaternary ammonium groups.

In another embodiment, the derivatized cyclodextrin is a "polyanion" or "polycation." A polyanion is a derivatized cyclodextrin having more than one negatively charged group resulting in net a negative ionic charge of more than two units. A polycation is a derivatized cyclodextrin having more than one positively charged group resulting in net positive ionic charger of more than two units.

In another embodiment, the derivatized cyclodextrin is a "chargeable amphiphile." By "chargeable" is meant that the amphiphile has a pK in the range pH 4 to pH 8 or 8.5. A chargeable amphiphile may therefore be a weak acid or base. By "amphoteric" herein is meant a derivatized cyclodextrin having a ionizable groups of both anionic and cationic character wherein: (a) at least one, and optionally both, of the cation and anionic amphiphiles is chargeable, having at least one charged group with a pK between 4 and 8 to 8.5, (b) the cationic charge prevails at pH 4, and (c) the anionic charge prevails at pH 8 to 8.5.

In some embodiments, the "ionizable" or "charged" derivatized cyclodextrin as a whole, whether polyionic, amphiphilic, or otherwise, are weakly ionizable (i.e., have a pKai of between about 4.0-8.5, 4.5-8.0, 5.0-7.5, 5.5-7.0, 6.0-6.5, and any range in between inclusive).

Any one, some, or all hydroxyl groups of any one, some or all $\alpha$-D-glucopyranoside units of a cyclodextrin can be modified to an ionizable chemical group as provided herein. Since each cyclodextrin hydroxyl group differs in chemical reactivity, reaction with a modifying moiety can produce an amorphous mixture of positional and optical isomers. Alternatively, certain chemistry can allow for pre-modified $\alpha$-D-glucopyranoside units to be reacted to form uniform products.

The aggregate substitution that occurs for cyclodextrin derivatives in a mixture is described by a term referred to as the degree of substitution. For example, a 6-ethylenediamino-$\beta$-cyclodextrin with a degree of substitution of seven would be composed of a distribution of isomers of 6-ethylenediamino-$\beta$-cyclodextrin in which the average number of ethylenediamino groups per 6-ethylenediamino-$\beta$-cyclodextrin molecule is seven. The degree of substitution for a cyclodextrin derivative mixture can routinely be determined using mass spectrometry or nuclear magnetic resonance spectroscopy.

In one embodiment, at least one hydroxyl moiety facing away from the cyclodextrin interior is substituted with an ionizable chemical group. For example, the C2, C3, C6, C2 and C3, C2 and C6, C3 and C6, and all three of C2-C3-C6 hydroxyls of at least one $\alpha$-D-glucopyranoside unit are substituted with an ionizable chemical group. Any such combination of hydroxyls can similarly be combined with at least two, three, four, five, six, seven, eight, nine, ten, eleven, up to all of the alpha-D-glucopyranoside units in the modified cyclodextrin as well as in combination with any degree of substitution provided herein. One such derivative is a sulfoalkyl ether cyclodextrin (SAE-CD). Sulfobutyl ether derivatives of beta cyclodextrin (SBE-$\beta$-CD) have been demonstrated to have significantly improved aqueous solubility compared to the parent cyclodextrin.

Additional cyclodextrin derivatives that may be complexed with therapeutic agents in the provided liposome compositions include sugammadex or Org-25969, in which the 6-hydroxy groups on $\gamma$-CD have been replaced by carboxythio acetate ether linkages, and hydroxybutenyl-$\beta$-CD. Alternative forms of cyclodextrin include: 2,6-Di-O-methyl-$\beta$-CD (DIMEB), 2-hydroxypropyl-3-cyclodextrin (HP-β-CD), randomly methylated-β-cyclodextrin (RAMEB), sulfobutyl ether β-cyclodextrin (SBE-β-CD), and sulfobutylether-γ-cyclodextrin (SBEγCD), sulfobutylated beta-cyclodextrin sodium salt, sulfobutylated beta-cyclodextrin sodium salt, (2-Hydroxypropyl)-alpha-cyclodextrin, (2-Hydroxypropyl)-beta-cyclodextrin, (2-Hydroxypropyl)-γ-cyclodextrin, 2,6-di-O-methyl)-beta-cyclodextrin (DIMEB-50 Heptakis), 2,3,6-tri-O-methyl)-beta-cyclodextrin (TRIMEB Heptakis), methyl-beta-cyclodextrin, octakis (6-deoxy-6-iodo)-γ-cyclodexrin, and, octakis (6-deoxy-6-bromo)-gamma-cy clodexrin.

In some embodiments, the cyclodextrin(s) has a high solubility in water in order to facilitate entrapment of a larger amount of the cyclodextrin in the liposome internal phase. In some embodiments, the water solubility of the cyclodextrin is at least 10 mg/mL, 20 mg/mL, 30 mg/mL, 40 mg/mL, 50 mg/mL, 60 mg/mL, 70 mg/mL, 80 mg/mL, 90 mg/mL, 100 mg/mL or higher. In some embodiments, the water solubility of the cyclodextrin(s) is within a range of 10-150 mg/mL, 20-100 mg/mL 20-75 mg/mL, and any range in between inclusive.

In some embodiments, a large association constant between the cyclodextrin and the therapeutic agent is preferable and can be obtained by selecting the number of glucose units in the cyclodextrin based on the size of the therapeutic agent (see, for example, Albers et al., Crit. Rev. Therap. Drug Carrier Syst. 12:311-337 (1995); Stella et al., Toxicol. Pathol. 36:30-42 (2008). When the association constant depends on pH, the cyclodextrin can be selected such that the association constant becomes large at the pH of the liposome internal phase. As a result, the solubility (nominal solubility) of the therapeutic agent in the presence of cyclodextrin can be further improved. In some embodiments, the association constant of the cyclodextrin with the therapeutic agent is 100, 200, 300, 400, 500, 600, 700, 800, 900, 1,000, or higher. In some embodiments, the association constant of the cyclodextrin with the therapeutic agent is in the range 100-1,200, 200-1,000, 300-750, and any range in between inclusive.

In some embodiments, the cyclodextrin of the pharmaceutical composition is underivatized.

In some embodiments, the cyclodextrin derivative of the pharmaceutical composition has the structure of Formula I:

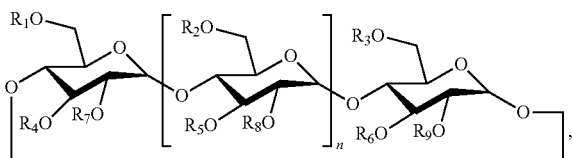

wherein: n is 4, 5, or 6;
wherein $R_1$, $R_2$, $R_3$, $R_4$, $R_5$, $R_6$, $R_7$, $R_8$, and $R_9$ are each, independently, —H, a straight chain or branched $C_1$-$C_8$-alkylene group, or an optionally substituted straight-chain or branched $C_1$-$C_6$ group, wherein at least one of $R_1$, $R_2$, $R_3$, $R_4$, $R_5$, $R_6$, $R_7$, $R_8$ and $R_9$ is a straight-chain or branched $C_1$-$C_8$-alkylene (e.g., $C_1$-$C_8$-(alkylene)-$SO_3^-$ group);

In some embodiments, the cyclodextrin derivative of the liposome composition has the structure of formula II:

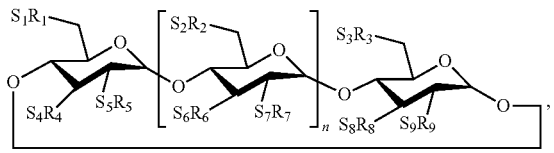

wherein: n is 4, 5, or 6;
wherein $R_1$, $R_2$, $R_3$, $R_4$, $R_5$, $R_6$, $R_7$, $R_8$, and $R_9$ are each, independently, —O— or a —O—($C_2$-$C_6$ alkylene)-$SO_3^-$ group; wherein at least one of $R_1$ and $R_2$ is independently a —O—($C_2$-$C_6$ alkylene)-$SO_3^-$ group; and $S_1$, $S_2$, $S_3$, $S_4$, $S_5$, $S_6$, $S_7$, $S_8$, and $S_9$ are each, independently, a pharmaceutically acceptable cation. In further embodiments, the pharmaceutically acceptable cation is selected from: an alkali metal such as Li+, Na+, or K+; an alkaline earth metal such as Ca+2, or Mg+2, and ammonium ions and amine cations such as the cations of (C1-C6)-alkylamines, piperidine, pyrazine, (C1-C6)-alkanolamine and (C4-C8)-cycloalkanolamine. In some embodiments, at least one of $R_1$ and $R_2$ is independently a —O—(C2-C6 alkylene)-SO3— group that is a —O—$(CH_2)_m$SO3— group, wherein m is 2 to 6, preferably 2 to 4, (e.g., —O—CH2CH2CH2S03— or —O—CH2CH2CH2CH2S03—); and $S_1$, $S_2$, $S_3$, $S_4$, $S_5$, $S_6$, $S_7$, $S_8$, and $S_9$ are each, independently, H or a pharmaceutically cation which includes for example, alkali metals (e.g., $Li^+$, $Na^+$, $K^+$) alkaline earth metals (e.g., $Ca^{+2}$, $Mg^{+2}$), ammonium ions and amine cations such as the cations of (C1-C6)-alkylamines, piperidine, pyrazine, ($C_1$-$C_6$)-alkanolamine and ($C_4$-$C_8$)-cycloalkanolamine.

In some embodiments, a cyclodextrin derivative of the liposome composition is a cyclodextrin disclosed in U.S. Pat. Nos. 6,133,248, 5,874,418, 6,046,177, 5,376,645, 5,134,127, 7,034,013, 6,869,939; and Intl. Appl. Publ. No. WO 02005/117911, the contents each of which is herein incorporated by reference in its priority.

In some embodiments, the cyclodextrin derivative of the liposome composition is a sulfoalkyl ether cyclodextrin. In some embodiments, the cyclodextrin derivative of the liposome composition is a sulfobutyl ether-3-cyclodextrin such as CAPTISOL® (CyDex Pharma Inc., Lenexa, Kansas). Methods for preparing sulfobutyl ether-3-cyclodextrin and other sulfoalkyl ether cyclodextrins are known in the art.

In some embodiments, the cyclodextrin derivative in the liposome composition is a compound of Formula III:

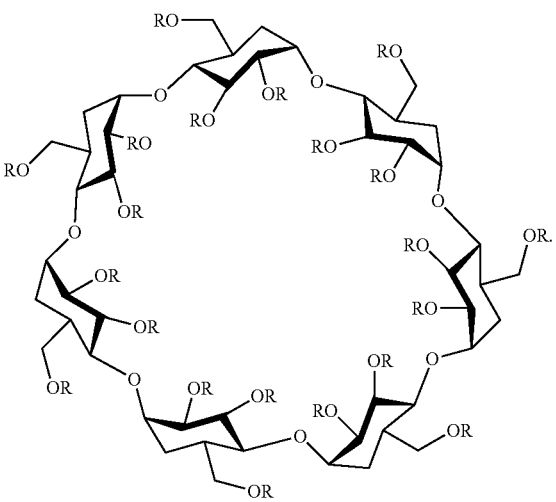

wherein R equals:
(a) $(H)_{21-X}$ or (—$CH_2)_4$—$SO_3Na$)x, and x=1.0-10.0, 1.0-5.0, 6.0-7.0 or 8.0-10.0;
(b) $(H)_{21-X}$ or (—$CH_2CH(OH)CH_3$)x, and x=1.0-10.0, 1.0-5.0, 6.0-7.0 or 8.0-10.0;
(c) $(H)_{21-X}$ or (sulfoalkyl ethers)x, and x=1.0-10.0, 1.0-5.0, 6.0-7.0 or 8.0-10.0; or
(d) $(H)_{21-X}$ or (—$CH_2)_4$—$SO_3Na$)x, and x=1.0-10.0, 1.0-5.0, 6.0-7.0 or 8.0-10.0.

In some embodiments, the provided compositions comprise liposome delivery vehicles. Liposomes are phospholipid vesicles composed of lipid bilayers enclosing one or more aqueous compartments. The term "liposome" refers to a microscopic closed vesicle having an internal phase enclosed by a lipid bilayer. A liposome can be a small single-lipid bilayer liposome such as a small unilamellar vessicle (SUV), large single-membrane liposome such as a large unilamellar vesicle (LUV), a still larger single-membrane liposome such as a giant unilamellar vesicle (GUV), a multilayer liposome having multiple concentric lipid bilayers such as a multilamellar vesicle (MLV), or a liposome having multiple lipid bilayers that are irregular and not concentric such as a multivesicular vesicle (MVV). See, e.g., U.S. Pat. Publ. 2012/0128757; U.S. Pat. Nos. 4,235,871 and 4,737,323; and Intl. Appl. Publ. No. WO 96/14057.

The term "liposome composition" as used herein, refers to a composition comprising liposomes that in turn contain complexes of a therapeutic agent and one or more polyglutamate molecules or cyclodextrin in the internal phase of the liposome. Liposome compositions can include solid and liquid forms. In instances where the liposome composition is in a solid form, the liposome composition can be made into a liquid form by dissolving or suspending it in a pharmaceutically acceptable solvent. In the case where the liposome composition is frozen solid, the composition can be made into a liquid form by melting.

The concentration of liposome and the concentration of the therapeutic agent in the liposome composition can be appropriately set according to the liposome composition objective, formulation, and other considerations known to the skilled artisan.

In some embodiments, the liposomes in the liposome composition are targeted pegylated liposomes. In some embodiments, the pegylated liposomes contain complexes of platinum-based chemotherapeutic agents and cyclodextrin within their aqueous internal phase, a PEG molecule attached to an exterior of the liposome; and a targeting moiety comprising a protein (e.g., an antibody or antibody fragment) with specific affinity for at least one antigen expressed on the surface of the cancer cell (e.g., a folate receptor such as FR-α, FR-β and/or FR-δ)), and wherein the targeting moiety is attached to at least one of the PEG and the exterior of the liposome. In other embodiments, the pegylated liposomes contain complexes of platinum-based chemotherapeutic agents and polyglutamate molecules within their aqueous internal phase, a PEG molecule attached to an exterior of the liposome; and a targeting moiety comprising a protein (e.g., an antibody or antibody fragment) with specific affinity for at least one antigen expressed on the surface of the cancer cell (e.g., a folate receptor such as FR-α, FR-β and/or FR-δ)), and wherein the targeting moiety is attached to at least one of the PEG and the exterior of the liposome.

The lipids and other components of the liposomes contained in the liposome compositions can be any lipid, lipid combination and ratio, or combination of lipids and other liposome components and their respective ratios known in the art. However, it will be understood by one skilled in the art that liposomal encapsulation of any particular drug, such as, and without limitation, therapeutic agents such as platinum-based chemotherapeutic agents discussed herein, may involve substantial routine experimentation to achieve a useful and functional liposomal formulation. However, it will be understood by one skilled in the art that liposomal encapsulation of any particular drug, such as, and without limitation, complexes of platinum-based chemotherapeutic agents and one or more polyglutamate molecules, complexes of platinum-based chemotherapeutic agents and cyclodextrin, complexes of gemcitabine-based chemotherapeutic agents and one or more polyglutamate molecules or cyclodextrin, and complexes of polyglutamated antifolate-based chemotherapeutic agents and cyclodextrin. In general, the provided liposomes may have any liposome structure, e.g., structures having an inner space sequestered from the outer medium by one or more lipid bilayers, or any microcapsule that has a semi-permeable membrane with a lipophilic central part where the membrane sequesters an interior. The lipid bilayer can be any arrangement of amphiphilic molecules characterized by a hydrophilic part (hydrophilic moiety) and a hydrophobic part (hydrophobic moiety). Usually amphiphilic molecules in a bilayer are arranged into two dimensional sheets in which hydrophobic moieties are oriented inward the sheet while hydrophilic moieties are oriented outward. Amphiphilic molecules forming the provided liposomes can be any known or later discovered amphiphilic molecules, e.g., lipids of synthetic or natural origin or biocompatible lipids. The liposomes can also be formed by amphiphilic polymers and surfactants, e.g., polymerosomes and niosomes. For the purpose of this disclosure, without limitation, these liposome-forming materials also are referred to as "lipids".

The formulations provided herein such as liposome composition formulations, can be in liquid or dry form such as a dry powder or dry cake. The dry powder or dry cake may have undergone primary drying under, for example, lyophilization conditions or optionally, the dry cake or dry powder may have undergone both primary drying only or both primary drying and secondary drying. In the dry form, the powder or cake may, for example, have between 1% to 6% moisture, for example, such as between 2% to 5% moisture or between 2% to 4% moisture. One example method of drying is lyophilization (also called freeze-drying, or cyrodessication). Any of the compositions and methods of the disclosure may include liposomes, lyophilized liposomes or liposomes reconstituted from lyophilized liposomes. In some embodiments, the disclosed compositions and methods include one or more lyoprotectants or cryoprotectants. These protectants are typically polyhydroxy compounds such as sugars (mono-, di-, and polysaccharides), polyalcohols, and their derivatives, glycerol, or polyethyleneglycol, trehalose, maltose, sucrose, glucose, lactose, dextran, glycerol, or aminoglycosides. In further embodiments, the lyoprotectants or cryoprotectants comprise up to 10% or up to 20% of a solution outside the liposome, inside the liposome, or both outside and inside the liposome.

In some embodiments, the liposomes include a steric stabilizer that increases their longevity in circulation. One or more steric stabilizers such as a hydrophilic polymer (Polyethylene glycol (PEG)), a glycolipid (monosialoganglioside (GM1)) or others occupies the space immediately adjacent to the liposome surface and excludes other macromolecules from this space. Consequently, access and binding of blood plasma opsonins to the liposome surface are hindered, and thus interactions of macrophages with such liposomes, or any other clearing mechanism, are inhibited and longevity of the liposome in circulation is enhanced. In some embodiments, the steric stabilizer or the population of steric stabilizers is a PEG or a combination comprising PEG. In further embodiments, the steric stabilizer is a PEG or a combination comprising PEG with a number average molecular weight (Mn) of 200 to 5000 daltons. These PEG(s) can be of any structure such as linear, branched, star or comb structure and are commercially available.

The diameter of the liposomes is not particularly limited. Depending on the desired application, the particle size of the liposome can be regulated. For example, when it is intended to transmit liposome to cancerous tissue or inflamed tissue by the Enhanced Permeability and Retention (EPR) effect as an injection product or the like, it is preferable that liposome particle size be 30-400 nm, 50-200 nm, 75-100 nm, and any range in between. In the case where the intention is to transmit liposome to macrophage, it is preferable that liposome particle size be 30 to 1000 nm, and it is more preferable that the particle size be 100 to 400 nm. It should be noted that in normal tissue, vascular walls serve as barriers (because the vascular walls are densely constituted by vascular endothelial cells), and microparticles such as supermolecules and liposome of specified size cannot be distributed within the tissue. However, in diseased tissue, vascular walls are loose (because interstices exist between vascular endothelial cells), increasing vascular permeability, and supermolecules and microparticles can be distributed to extravascular tissue (enhanced permeability). Moreover, the lymphatic system is well developed in normal tissue, but it is known that the lymphatic system is not developed in diseased tissue, and that supermolecules or microparticles, once incorporated, are not recycled through the general system, and are retained in the diseased tissue (enhanced retention), which forms the basis of the EPR effect. Thus, it is possible to control liposome pharmacokinetics by adjusting liposome particle size.

In some embodiments, the liposomes have a diameter in the range of for example, 10-250 nm. In some embodiments, the liposomes have a diameter in the range of for example, 30-150 nm. In other embodiments, the liposomes have a diameter in the range of 40-70 nm.

The properties of liposomes are influenced by the nature of lipids used to make the liposomes. A wide variety of lipids have been used to make liposomes. These include cationic, anionic and neutral lipids. In some embodiments, the liposomes comprising the complexes containing cyclodextrin and the therapeutic agent (e.g., a platinum-based chemotherapeutic agent, a doxorubicin-based chemotherapeutic agent, a gemcitabine-based chemotherapeutic agent, and a taxane-based chemotherapeutic agent) are anionic or neutral. In other embodiments, the provided liposomes are cationic. The determination of the charge (e.g., anionic, neutral or cationic) can routinely be determined by measuring the zeta potential of the liposome. The zeta potential of the liposome can be positive, zero or negative. In some embodiments, the zeta potential of the liposome is less than or equal to zero. In some embodiments, the zeta potential of the liposome is in a range of 0 to −150 mV. In another embodiment, the zeta potential of the liposome is in the range of −30 to −50 mV.

Alternatively, in some embodiments, the zeta potential of the liposome is greater than zero. In some embodiments, the zeta potential of the liposome between 1 and 100 mV. In another embodiment, the zeta potential of the liposome is in the range of 5 to 60 mV. In another embodiment, the zeta potential of the liposome is in the range of 10 to 50 mV.

Techniques and reagents are known in the art for routinely determining the zeta potential of a liposome such as, dynamic light scattering using a Malvern Zetasizer ZS).

In some embodiments, cationic lipids are used to make cationic liposomes which are commonly used as gene transfection agents. The positive charge on cationic liposomes enables interaction with the negative charge on cell surfaces. Following binding of the cationic liposomes to the cell, the liposome is transported inside the cell through endocytosis.

In some preferred embodiments, a neutral to anionic liposome is used. In a preferred embodiment, an anionic liposome is used. Using a mixture of, for example, neutral lipids such as HSPC and anionic lipids such as PEG-DSPE results in the formation of anionic liposomes which are less likely to non-specifically bind to normal cells. Specific binding to tumor cells can be achieved by using a tumor targeting antibody such as, for example, a folate receptor antibody, including, for example, folate receptor alpha antibody, folate receptor beta antibody and/or folate receptor delta antibody.

As an example, at least one (or some) of the lipids is/are amphipathic lipids, defined as having a hydrophilic and a hydrophobic portions (typically a hydrophilic head and a hydrophobic tail). The hydrophobic portion typically orients into a hydrophobic phase (e.g., within the bilayer), while the hydrophilic portion typically orients toward the aqueous phase (e.g., outside the bilayer). The hydrophilic portion can comprise polar or charged groups such as carbohydrates, phosphate, carboxylic, sulfato, amino, sulfhydryl, nitro, hydroxy and other like groups. The hydrophobic portion can comprise apolar groups that include without limitation long chain saturated and unsaturated aliphatic hydrocarbon groups and groups substituted by one or more aromatic, cyclo-aliphatic or heterocyclic group(s). Examples of amphipathic compounds include, but are not limited to, phospholipids, aminolipids and sphingolipids.

Typically, the lipids making up the liposomes in the provided liposome compositions are phospholipids. Phospholipids include without limitation phosphatidylcholine, phosphatidylethanolamine, phosphatidylglycerol, phosphatidylinositol, phosphatidylserine, and the like. It is to be understood that other lipid membrane components, such as cholesterol, sphingomyelin, and cardiolipin, can be used.

The lipid bilayer of the liposome comprises phospholipids and/or phospholipid derivatives. In addition to phospholipids and/or phospholipid derivatives, the liposome can further include sterols, such as cholesterol and cholestanol as membrane stabilizers and fatty acids having saturated or unsaturated acyl groups, such as those having a carbon number of 8, 9, 10, 11, 12, 13, 14, 15, 16, 17, 18, 19, 20, or longer. Representative, non-limiting examples include acyl groups derived from fatty-acid such as lauric acid, myristic acid, palmitic acid, stearic acid, oleic acid, and linoleic acid.

In some embodiments, the lipid bilayer comprises a phospholipid. In some embodiments, the lipid bilayer comprises one or more different phospholipids. In additional embodiments, the lipid bilayer comprises a phospholipid derived from a natural substance. In further embodiments, the lipid bilayer comprises a phospholipid derived from a member selected from the group: egg-yolk lecithin and soy lecithin, partially hydrogenated egg-yolk lecithin, (completely) hydrogenated egg-yolk lecithin, partially hydrogenated soy lecithin, and (completely) hydrogenated soy lecithin whose unsaturated fatty-acid residues are partially or completely hydrogenated.

In some embodiments, the lipid bilayer comprises a phospholipid derivative. In some embodiments, the lipid bilayer comprises one or more different phospholipid derivatives.

In some embodiments, the lipid bilayer comprises both phospholipids and phospholipid derivatives.

In some embodiments, the lipid bilayer comprises one or more different phospholipids and one or more different phospholipid derivatives. In some embodiments, the lipid bilayer comprises a phospholipid or a phospholipid derivative selected from the group: phosphatidyl ethanolamine, phosphatidyl choline, phosphatidyl serine, phosphatidyl inositol, phosphatidyl glycerol, cardiolipin, sphingomyelin, ceramide phosphorylethanolamine, ceramide phosphoryl glycerol, ceramide phosphoryl glycerol phosphate, 1,2-dimyristoyl-1,2-deoxyphosphatidyl choline, plasmalogen, and phosphatidic acid. It is also acceptable to combine one or more of these phospholipids and phospholipid derivatives.

Representative, non-limiting examples of modified lipids that can be included in the provided liposome compositions include PEG lipids, sugar lipids, antibody-modified lipids, peptide-modified lipids, and the like. Liposomes containing such modified lipids can be targeted to desired target cells or target tissue. Also, there are no particular limitations on the mixing amount (mole fraction) of functional lipids and modified lipids used when preparing the liposome. In some embodiments, such lipids make up 0-50%, 0-40%, 0-30%, 0-20%, 0-15%, 0-10%, 0-5%, 0-1% or less of the entirety of liposome lipid bilayer constituent lipids.

The lipids comprising the liposomes in the provided liposome compositions can be anionic and neutral (including zwitterionic and polar) lipids including anionic and neutral phospholipids. Neutral lipids exist in an uncharged or neutral zwitterionic form at a selected pH. At physiological pH, such lipids include, for example, dioleoylphosphatidylglycerol (DOPG), diacylphosphatidylcholine, diacylphosphatidylethanol-amine, ceramide, sphingomyelin, cephalin, cholesterol, cerebrosides and diacylglycerols. Examples of zwitterionic lipids include without limitation dioleoylphosphatidylcholine (DOPC), dimyristoylphosphatidylcholine (DMPC), and dioleoylphosphatidylserine (DOPS). Anionic lipids are negatively charged at physiological pH. These lipids include without limitation phosphatidylglycerol, cardiolipin, diacylphosphatidylserine, diacylphosphatidic acid, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

Collectively, anionic and neutral lipids are referred to herein as non-cationic lipids. Such lipids may contain phosphorus but they are not so limited. Examples of non-cationic lipids include lecithin, lysolecithin, phosphatidylethanolamine, lysophosphatidylethanolamine, dioleoylphosphatidylethanolamine (DOPE), dipalmitoyl phosphatidyl ethanolamine (DPPE), dimyristoylphosphoethanolamine (DMPE), distearoyl-phosphatidylethanolamine (DSPE), palmitoyloleoyl-phosphatidylethanolamine (POPE) palmitoyloleoyl-phosphatidylcholine (POPC), egg phosphatidylcholine (EPC), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), palmitoyloleyolphosphatidylglycerol (POPG), 16-0-monomethyl PE, 16-0-dimethyl PE, 18-1-trans PE, palmitoyloleoyl-phosphatidylethanolamine (POPE), 1-stearoyl-2-oleoylphosphatidyethanolamine (SOPE), phosphatidylserine, phosphatidylinositol, sphingomyelin, cephalin, cardiolipin, phosphatidic acid, cerebrosides, dicetylphosphate, and cholesterol.

The liposomes may be assembled using any liposomal assembly method using liposomal components (also referred to as liposome components) known in the art. Liposomal components include, for example, lipids such as DSPE, HSPC, cholesterol and derivatives of these components. Other suitable lipids are commercially available for example, by Avanti Polar Lipids, Inc. (Alabaster, Alabama, USA). A partial listing of available negatively or neutrally charged lipids suitable for making anionic liposomes, can be, for example, at least one of the following: DLPC, DMPC, DPPC, DSPC, DOPC, DMPE, DPPE, DOPE, DMPA•Na, DPPA•Na, DOPA•Na, DMPG•Na, DPPG•Na, DOPG•Na, DMPS•Na, DPPS•Na, DOPS•Na, DOPE-Glutaryl•(Na)2, Tetramyristoyl Cardiolipin •(Na)2, DSPE-mPEG-2000•Na, DSPE-mPEG-5000•Na, and DSPE-Maleimide PEG-2000•Na.

In some embodiments, the liposome compositions provided herein are formulated in a liposome comprising a cationic lipid. In one embodiment, the cationic lipid is selected from, but not limited to, a cationic lipid described in Intl. Appl. Publ. Nos. WO 2012/040184, WO2011/153120, WO2011/149733, WO2011/090965, WO2011/043913, WO2011/022460, WO2012/061259, WO2012/054365, WO2012/044638, WO 2010/080724, WO2010/21865 and WO2008/103276, U.S. Pat. Nos. 7,893,302, 7,404,969 and 8,283,333 and US Appl. Publ. Nos. US20100036115 and US20120202871; each of which is herein incorporated by reference in their entirety. In another embodiment, the cationic lipid may be selected from, but not limited to, formula A described in Intl. Appl. Publ. Nos. WO2012/040184, WO2011/153120, WO2011/1149733, WO2011/090965, WO2011/043913, WO2011/022460, WO2012/061259, WO2012/054365 and WO2012/044638; each of which is herein incorporated by reference in their entirety. In yet another embodiment, the cationic lipid may be selected from, but not limited to, formula CLI-CLXXIX of International Publication No. WO2008103276, formula CLI-CLXXIX of U.S. Pat. No. 7,893,302, formula CLI-CLXXXXII of U.S. Pat. No. 7,404,969 and formula I-VI of US Publication No. US20100036115; each of which is herein incorporated by reference in their entirety. As a non-limiting example, the cationic lipid may be selected from (20Z,23Z)-N,N-dimethylnonacosa-20,23-dien-10-amine, (17Z,20Z)-N,N-dimemyl-hexacosa-17,20-dien-9-amine, (1Z,19Z)-NSN-dimethylpentacosa-16,19-dien-8-amine, (13Z, 16Z)-N,N-dimethyldocosa-13,16-dien-5-amine, (12Z,15Z)-N,N-dimethyl-henicosa-12,15-dien-4-amine, (14Z,17Z)-N,N-dimethyltricosa-14,17-dien-6-amine, (15Z,18Z)-N,N-dimethyltetracosa-15,18-dien-7-amine, (18Z,21Z)-N,N-dimethylheptacosa-18,21-dien-10-amine, (15Z,18Z)-N,N-dimethyltetracosa-15,18-dien-5-amine, (14Z,17Z)-N,N-dimethyl-tricosa-14,17-dien-4-amine, (19Z,22Z)-N,N-dimeihyloctacosa-19,22-dien-9-amine, (18Z,21 Z)-N,N-dimethylheptacosa-18,21-dien-8-amine, (17Z,20Z)-N,N-dimethylhexa-cosa-17,20-dien-7-amine, (16Z,19Z)-N,N-dimethylpentacosa-16,19-dien-6-amine, (22Z,25Z)-N,N-dimethylhentriaconta-22,25-dien-10-amine, (21Z,24Z)-N,N-dimethyl-triaconta-21,24-dien-9-amine, (18Z)-N,N-dimetylheptacos-18-en-10-amine, (17Z)-N,N-dimethylhexacos-17-en-9-amine, (19Z,22Z)-N,N-dimethyloctacosa-19,22-dien-7-amine, N,N-dimethylheptacosan-10-amine, (20Z,23Z)-N-ethyl-N-methylnonacosa-20,23-dien-10-amine, 1-[(11Z,14Z)-1- nonylicosa-11,14-dien-1-yl] pyrrolidine, (20Z)-N,N-dimethyl-heptacos-20-en-10-amine, (15Z)-N,N-dimethyleptacos-15-en-10-amine, (14Z)-N,N-dimethylnonacos-14-en-10-amine, (17Z)-N,N-dimethylnonacos-17-en-10-amine, (24Z)-N,N-dimethyltritriacont-24-en-10-amine, (20Z)-N,N-dimethylnonacos-20-en-10-amine, (22Z)-N,N-dimethylhentriacont-22-en-10-amine, (16Z)-N,N-dimethylpenta-cos-16-en-8-amine, (12Z,15Z)-N,N-dimethyl-2-nonylheni-cosa-12,15-dien-1-amine, (13Z,16Z)-N,N-dimethyl-3-nonyldocosa-13,16-dien-1-amine, N,N-dimethyl-1-[(1S,2R)-2-octylcyclo-propyl] eptadecan-8-amine, 1-[(1S,2R)-2-hexylcyclopropyl]-N,N-dimethyl nonadecan-10-amine, N,N-dimethyl-1-[(1S,2R)-2-octylcyclopropyl]-nonadecan-10-amine, N,N-dimethyl-21-[(1S,2R)-2-octylcyclopropyl] henicosan-10-amine,N,N-dimethyl-1-[(1S,2S)-2-{[(1R,2R)-2-pentylcyclopropyl]methyl}cyclopropyl] nonadecan-10-amine,N,N-dimethyl-1-[(1S,2R)-2-octylcyclopropyl]hexadecan-8-amine, N,N-dimethyl-[(1R,2S)-2-undecyl-cyclopropyl] tetradecan-5-amine, N,N-dimethyl-3-{7-[(1S, 2R)-2-octylcyclopropyl]heptyl}dodecan-1-amine, 1-[(1R,2S)-2-heptylcyclopropyl]-N,N-dimethyloctadecan-9-amine, 1-[(1S,2R)-2-decylcyclopropyl]-N,N-dimethyl-penta-decan-6-amine, N,N-dimethyl-1-[(1S,2R)-2-octylcyclopropyl]pentadecan-8-amine, R—N,N-dimethyl-1-[(9Z,12Z)-octadeca-9,12-dien-1-yloxy]-3-(octyloxy)propan-2-amine, S—N,N-dimethyl-1-[(9Z,12Z)-octadeca-9,12-dien-1-yloxy]-3-(octyloxy)propan-2-amine, 1-{2-[(9Z,12Z)-octadeca-9,12-dien-1-yloxy]-1-[(octyloxy)methyl]ethyl}pyrrolidine, (2S)—N,N-dimethyl-1-[(9Z,12Z)-octadeca-9,12-dien-1-yloxy]-3-[(5Z-)-oct-5-en-1-yloxy] propan-2-amine, 1-{2-[(9Z,12Z)-octadeca-9,12-dien-1-yloxy]-1-[(octyloxy)methyl]ethyl}azetidine, (2S)-1-(hexyloxy)-N,N-dimethyl-3-[(9Z,12Z)-octadeca-9,12-dien-1-yloxy]propan-2-amine, (2S)-1-(heptyloxy)-N,N-dimethyl-3-[(9Z,12Z)-octadeca-9,12-dien-1-yloxy]propan-2-amine, N,N-dimethyl-1-(nonyloxy)-3-[(9Z,12Z)-octadeca-9,12-dien-1-yloxy]propan-2-amine, N,N-dimethyl-1-[(9Z)-octadec-9-en-1-yloxy]-3-(octyloxy) propan-2-amine; (2S)-N,N-dimethyl-1-[(6Z,9Z,12Z)-octadeca-6,9,12-trien-1-yloxy]-3-(octyloxy)propan-2-amine, (2S)-1-[(11Z,14Z)-icosa-11,14-dien-1-yloxy]-N,N-dimethyl-3-(pentyloxy)propan-2-amine, (2S)-1-(hexyloxy)-3-[(11Z,14Z)-icosa-11,14-dien-1-yloxy]-N,N-dimethylpropan-2-amine, 1-[(11Z,14Z)-icosa-11,14-dien-1-yloxy]-N,N-dimethyl 1-3-(octyloxy)propan-2-amine, 1-[(13Z,16Z)-docosa-13,16-dien-1-yloxy]-N,N-dimethyl-3-(octyloxy)propan-2-amine, (2S)-1-[(13Z,16Z)-docosa-13,16-dien-1-yloxy]-3-(hexyloxy)-N,N-dimethyl-propan-2-amine, (2S)-1-[(13Z)-docos-13-en-1-yloxy]-3-(hexyloxy)-N,N-dimethyl propan-2-amine, 1-[(13Z)-docos-13-en-1-yloxy]-N,N-dimethyl-3-(octyloxy) propan-2-amine, 1-[(9Z)-hexadec-9-en-1-yloxy]-N,N-dimethyl-3-(octyloxy)propan-2-amine, (2R)-N,N-dimethyl-H(1-metoyloctyl)oxy]-3-[(9Z,12Z)-octa-deca-9,12-dien-1-yloxy]propan-2-amine, (2R)-1-[(3,7-dimethyloctyl)oxy]-N,N-dimethyl-3-R9Z,12Z)-octadeca-9,12-dien-1-yloxylpropan-2-amine, N,N-dimethyl-1-(octyloxy)-3-({8-[(1S,2S)-2-{[(1R,2R)-2-pentylcyclopropyl]-methyl}cyclopropyl] octyl}oxy) propan-2-amine, N,N-dimethyl-1-{[-(2-oclylcyclopropyl)octyl]oxy}-3-(octyloxy) propan-2-amine and (11E,20Z,23Z)-N,N-dimethylnonacosa-11,20,2-trien-10-amine or a pharmaceutically acceptable salt or acid or stereoisomer thereof.

In one embodiment, the lipid may be a cleavable lipid such as those described in Intl. Publ. No. WO2012/170889, which is herein incorporated by reference in its entirety The cationic lipid can routinely be synthesized using methods known in the art and/or as described in Intl. Publ. Nos. WO2012/040184, WO2011/153120, WO2011/149733, WO2011/090965, WO2011/1043913, WO2011/022460, WO2012/061259, WO 2012/054365, WO2012/044638, WO2010/080724 and WO2010/21865; each of which is herein incorporated by reference in its entirety.

Lipid derivatives can include, for example, at least, the bonding (preferably covalent bonding) of one or more steric stabilizers and/or functional groups to the liposomal component after which the steric stabilizers and/or functional groups should be considered part of the liposomal components. Functional groups comprises groups that can be used to attach a liposomal component to another moiety such as a protein. Such functional groups include, at least, maleimide. These steric stabilizers include at least one from the group consisting of polyethylene glycol (PEG); poly-L-lysine (PLL); monosialoganglioside (GM1); poly(vinyl pyrrolidone) (PVP); poly(acrylamide) (PAA); poly(2-methyl-2-oxazoline); poly(2-ethyl-2-oxazoline); phosphatidyl polyglycerol; poly[N-(2-hydroxypropyl) methacrylamide]; amphiphilic poly-N-vinylpyrrolidones; L-amino-acid-based polymer; and polyvinyl alcohol.

In some embodiments, the provided liposome compositions are formulated in a lipid-polycation complex. The formation of the lipid-polycation complex may be accomplished using methods known in the art and/or as described in U.S. Pub. No. 20120178702, herein incorporated by reference in its entirety. As a non-limiting example, the polycation may include a cationic peptide or a polypeptide such as, but not limited to, polylysine, polyornithine and/or polyarginine and the cationic peptides described in International Pub. No. WO2012/013326; herein incorporated by reference in its entirety. In another embodiment, the provided liposome compositions are formulated in a lipid-polycation complex which further includes a neutral lipid such as, but not limited to, cholesterol or dioleoyl phosphatidylethanolamine (DOPE).

Since the components of a liposome can include any molecule(s)(i.e., chemical/reagent/protein) that is bound to it, in some embodiments, the components of the provided liposomes include, at least, a member selected from the group DSPE, DSPE-PEG, DSPE-maleimide, HSPC; HSPC-PEG; HSPC-maleimide; cholesterol; cholesterol-PEG; and cholesterol-maleimide. In some embodiments, the components of the provided liposomes include DSPE, DSPE-PEG, DSPE-maleimide, HSPC; HSPC-PEG; HSPC-maleimide; cholesterol; cholesterol-PEG; and cholesterol-maleimide. In a preferred embodiment, the liposomal components that make up the liposome comprises DSPE; DSPE-FITC; DSPE-maleimide; cholesterol; and HSPC.

In additional embodiments, the liposomes of the liposome compositions provided herein comprise oxidized phospholipids. In some embodiments, the liposomes comprise an oxidize phospholipid of a member selected from the group consisting of phosphatidylserines, phosphatidylinositols, phosphatidylethanolamines, phosphatidylcholines and 1-palmytoyl-2-arachidonoyl-sn-glycero-2-phosphate. In some embodiments, the phospholipids have unsaturated bonds. In some embodiments, the phospholipids are arachidonic acid containing phospholipids. In additional embodiments, the phospholipids are sn-2-oxygenated. In additional embodiments, the phospholipids are not fragmented.

In some embodiments, the liposomes of the provided liposome compositions comprise oxidized 1-palmitoyl-2-arachidonoyl-sn-glycero-3-phosphorylcholine (OxPAPC). The term "oxPAPC", as used herein, refers to lipids generated by the oxidation of 1-palmitoyl-2-arachidonyl-sn-glycero-3-phosphorylcholine (PAPC), which results in a mixture of oxidized phospholipids containing either fragmented or full length oxygenated sn-2 residues. Well-characterized oxidatively fragmented species contain a five-carbon sn-2 residue bearing omega-aldehyde or omega-carboxyl groups. Oxidation of arachidonic acid residue also produces phospholipids containing esterified isoprostanes. oxPAPC includes HOdiA-PC, KOdiA-PC, HOOA-PC and KOOA-PC species, among other oxidized products present in oxPAPC. In further embodiments, the oxPAPCs are epoxyisoprostane-containing phospholipids. In further embodiments, the oxPAPC is 1-palmitoyl-2-(5,6-epoxyisoprostane E2)-sn-glycero-3-phosphocholine (5,6-PEIPC), 1-palmitoyl-2-(epoxy-cyclo-pentenone)-sn-glycero-3-phosphorylcholine (PECPC) and/or 1-palmitoyl-2-(epoxy-isoprostane E2)-sn-glycero-4-phosphocholine (PEIPC). In some embodiments, the phospholipids have unsaturated bonds. In some embodiments, the phospholipids are arachidonic acid containing phospholipids. In additional embodiments, the phospholipids are sn-2-oxygenated. In additional embodiments, the phospholipids are not fragmented.

In some embodiments, the liposomes of the provided liposome composition are pegylated. In some embodiments, the liposome composition is water soluble. That is, the liposome composition is in the form of an aqueous solution.

In some embodiments, the liposomes of the provided liposome compositions comprise a lipid selected from: 1-palmitoyl-2-glutaroyl-sn-glycero-3-phosphocholine (PGPC); 1-palmitoyl-2-(9'oxo-nonanoyl)-sn-glycero-3-phosphocholine; 1-palmitoyl-2-arachinodoyl-sn-glycero-3-phosphocholine; 1-palmitoyl-2-myristoyl-sn-glycero-3-phosphocholine; 1-palmitoyl-2-hexadecyl-sn-glycero-3-phosphocholine; 1-palmitoyl-2-azelaoyl-sn-glycero-3-phosphocholine; and 1-palmitoyl-2-acetoyl-sn-glycero-3-phosphocholine. In further embodiments, the liposome comprises PGPC.

In some embodiments, the pH of solutions comprising the liposome composition is from pH 2 to 8, or any range therein between. In some embodiments, the pH of solutions comprising the liposome composition is from pH 5 to 8, or any range therein between. In some embodiments, the pH of solutions comprising the liposome composition is from pH 6 to 7, or any range therein between. In some embodiments, the pH of solutions comprising the liposome composition is from 6 to 7.5, from 6.5 to 7.5, from 6.7 to 7.5, or from 6.3 to 7.0, or any range therein between.

In some embodiments, at least one component of the liposome lipid bilayer is functionalized (or reactive). As used herein, a functionalized component is a component that comprises a reactive group that can be used to crosslink reagents and moieties to the lipid. If the lipid is functionalized, any liposome that it forms is also functionalized. In some embodiments, the reactive group is one that will react with a crosslinker (or other moiety) to form crosslinks. The reactive group in the liposome lipid bilayer can be located anywhere on the lipid that allows it to contact a crosslinker and be crosslinked to another moiety (e.g., a steric stabilizer or targeting moiety). In some embodiments, the reactive group is in the head group of the lipid, including for example a phospholipid. In some embodiments, the reactive group is a maleimide group. Maleimide groups can be crosslinked to each other in the presence of dithiol crosslinkers including but not limited to dithiolthrietol (DTT).

The liposome can also contain functional lipids and modified lipids as membrane constituents. Representative, non-limiting examples of functional lipids include lipid derivatives retained in blood (e.g., glycophorin, ganglioside GM1, ganglioside GM3, glucuronic acid derivatives, glutaminic acid derivatives, polyglycerin phospholipid derivatives, polyethylene glycol derivatives (methoxypolyethylene glycol condensates, etc.) such as N-[carbonyl-methoxy polyethylene glycol-2000]-1, 2-dipalmitoyl-sn-glycero-3-phosphoethanolamine, N-[carbonyl-methoxy polyethylene glycol-5000]-1,2-dipalmitoyl-sn-glycero-3-phosphoethanolamine, N-[carbonyl-methoxypolyethylene glycol-750]-1, 2-distearoyl-sn glycero-3-phosphoethanolamine, N-[carbonyl-methoxy poly-ethyleneglycol-2000]-1,2-distearoyl-sn-glycero-3-phosphoethanolamine (MPEG 2000-distearoyl phosphatidyl ethanolamine), and N-[carbonyl-methoxy polyethylene glycol-5000]-1,2-distearoyl-sn-glycero-3-phosphoethanolamine, which are condensates of phosphoethanolamine and methoxy polyethylene glycol), temperature-sensitive lipid derivatives (e.g., dipalmitoyl phosphatidylcholine), pH-sensitive lipid derivatives (e.g., dioleoyl phosphatidyl ethanolamine), and the like. Liposomes containing lipid derivatives retained in blood are useful for improving the blood retention of the liposome, because the liposome becomes difficult to capture in the liver as a foreign impurity. Similarly, liposomes containing temperature-sensitive lipid derivatives are useful for causing destruction of liposome at specific temperatures and/or causing changes in the surface properties of the liposome. Furthermore, by combining this with an increase in temperature at the target site, it is possible to destroy the liposome at the target site, and release the therapeutic agent at the target site. Liposomes containing pH-sensitive lipid derivatives are useful for enhancing membrane fusion of liposome and endosome when the liposome is incorporated into cells due to the endocytosis to thereby improve transmission of the therapeutic agent to the cytoplasm.

It is to be understood that the use of other functionalized lipids, other reactive groups, and other crosslinkers beyond those described above is further contemplated. In addition to the maleimide groups, other examples of contemplated reactive groups include but are not limited to other thiol reactive groups, amino groups such as primary and secondary amines, carboxyl groups, hydroxyl groups, aldehyde groups, alkyne groups, azide groups, carbonyls, halo acetyl (e.g., iodoacetyl) groups, imidoester groups, N-hydroxysuccinimide esters, sulfhydryl groups, and pyridyl disulfide groups.

Functionalized and non-functionalized lipids are available from a number of commercial sources including Avanti Polar Lipids (Alabaster, AL) and Lipoid LLC (Newark, NJ).

In some embodiments, the liposomes of the disclosed lipid compositions further comprise an immunostimulatory agent, a detectable marker, or both disposed on its exterior surface. The immunostimulatory agent or detectable marker can be ionically bonded or covalently bonded to the exterior of the liposome, including, for example, optionally to a steric stabilizer component of the liposome.

The terms "immunostimulatory agents" "immunostimulants," "immune-stimulators," and the like are used interchangeably herein to refer to substances that stimulate the immune system by inducing activation or increasing activity of any of its components. These immunostimulatory agents can include one or more of a hapten, an adjuvant, a protein immunostimulating agent, a nucleic acid immunostimulating agent, and a chemical immunostimulating agent. Many adjuvants contain a substance designed to stimulate immune responses, such as lipid A, *Bordetella pertussis* or *Mycobacterium tuberculosis* derived proteins. Certain adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophos-phoryl lipid A and quil A. Cytokines, such as GM-CSF, interleukin-2, -7, and -12, and other growth factors, can also be used as adjuvants. In a preferred embodiment, the immunostimulant is selected from the group consisting of fluorescein, DNP, beta glucan, beta-1, 3-glucan, and beta-1,6-glucan.

A detectable marker may for example, include, at least, a radioisotope, a fluorescent compound, a bioluminescent compound, chemiluminescent compound, a metal chelator, an enzyme, a dye, an ink, a magnetic compound, a biocatalyst or a pigment that is detectable by any suitable means known in the art, e.g., magnetic resonance imaging (MRI), optical imaging, fluorescent/luminescent imaging, or nuclear imaging techniques.

In some embodiments, the immunostimulatory agent and/or detectable marker is attached to the exterior of the liposome by co-incubating the agent with the liposome. For example, the immunostimulatory agent and/or detectable marker may be associated with the liposomal membrane by hydrophobic interactions or by an ionic bond such as an avidin/biotin bond or a metal chelation bond (e.g., Ni-NTA). Alternatively, the immunostimulatory agent or detectable marker may be covalently bonded to the exterior of the liposome such as, for example, by being covalently bonded to a liposomal component or to the steric stabilizer which is the PEG.

In some embodiments, liposomes in the provided liposome compositions further comprise an agent that increases the uptake of liposomes into a cellular compartment of interest including the cytosol.

In some embodiments, liposomes in the provided liposome compositions comprise a mitochondrial-targeting agent. In some embodiments, the liposomes comprise triphenylphosphonium (TPP). Methods and mechanisms for surface functionalizing liposomes with TPP are known in the art (e.g., attaching TPP to the lipid anchor via a peg spacer group and modifying TPP with a stearyl group (stearyl triphenylphosphonium (STPP)). In some embodiments, the liposomes comprise high-density octa-arginine. In some embodiments, the liposomes comprise sphingomyelin and/or a sphingomyelin metabolite. Sphingomyelin metabolite used to formulate the liposomes of the present invention can include, for example ceramide, sphingosine or sphingosine 1-phosphate. In some embodiments, the liposomes comprise Rhodamine 123. In some embodiments, the liposomes comprise, a mitochondria penetrating peptide. In some embodiments, the liposomes comprise, a mitochondria penetrating agent selected from the group: a mitofusin peptide, a mitochondrial targeting signal peptide, Antennapedia helix III homeodomain cell-penetrating peptide (ANT) (e.g., comprising RQIKIWFQNRRMKWKKRKKRRQR RR (SEQ ID NO: 1), RKKRRXR RRGC where X is any natural or non-natural amino acid (e.g., comprising RQIKIWFQNRRMKWKKRKKRRQRRR
(SEQ ID NO: 1), RKKRRXR RRGC where X is any natural or non-natural amino acid (SEQ ID NO: 2), CCGCCAAGAAGCG (SEQ ID NO: 3), GCGTGCACA CGCGCGTAGACTTCCCCCGCAAGTCACTCGTTAGCCCGCCAAGAA GCGACCCCTCCGGGGCGAGCTGAGCGG CGTGGCGCGGGGGCGTC AT (SEQ ID NO: 4),ACGTGCATACGCACGTAGACATTCCCC GCTTCCCACTCCAAAGTCCGCCAAGAAGCGTATCCCGCTGAGCGG CGTGGCGCGGGGGCGTCATCCGTCAGCTC (SEQ ID NO: 5), or ACTTCCCCCGCAAGTCACTCGTTAGCCCGCCAAGAAGCGACC CCTCCGGGGCGAGCTG (SEQ ID NO: 6)), or a mitochondrial penetrating fragment thereof.

In some embodiments, liposomes in the provided liposome compositions comprise a mitochondria penetrating agent selected from the group: a guanidine-rich peptoid, tetraguanidinium, triguanidinium, diguanidinium, monoguanidinium, a guanidine-rich polycarbamate, a beta-oligoarginine, a proline-rich dendrimer, and a phosphonium salt (e.g., methyltriphenyl-phosphonium and/or tetraphenylphosphonium).

In some embodiments, liposomes in the provided liposome compositions comprise sphingomyelin and/or stearyl-octa-arginine. In some embodiments, the liposomes comprise sphingomyelin and/or stearyl-octa-arginine. In some embodiments, the liposomes comprise DOPE, sphingomyelin, stearyl-octa-arginine sphingomyelin and stearyl-octa-arginine. In some embodiments, the liposomes comprise DOPE, sphingomyelin, stearyl-octa-arginine sphingomyelin and stearyl-octa-arginine at a molar ratio of 9:2:1. In some embodiments, the liposomes comprise the MITO-porter system or a variant thereof.

In some embodiments, liposomes in the provided liposome compositions comprise an agent such as a cell penetrating agent that that facilitates delivery of the liposome across a cell membrane and provides the liposome with the ability to bypass the endocytic pathway and the harsh environment of lysosomes. Cell penetrating agents are known in the art and can routinely be used and adapted for manufacture and use of the provided liposome compositions. In some embodiments, the cell penetrating/lysosome bypassing agent is chloroquine. In some embodiments, the cell penetrating agent is a cell penetrating peptide. In some embodiments, liposomes in the provided liposome compositions comprise a cell penetrating agent selected from the group:

RKKRRQRRR, (SEQ ID NO: 7)

GRKKRRQRRRTPQ, (SEQ ID NO: 8)

YGRKKRRQRRR, (SEQ ID NO: 9)

AAVALLPAVLLALLA, (SEQ ID NO: 10)

MGLGLHLLVLAAALQ, (SEQ ID NO: 11)

GALFLGFLGAAGSTM, (SEQ ID NO: 12)

AGYLLGKINLKALAALAKKIL, (SEQ ID NO: 13)

RVIRVWFQNKRCKDKK, (SEQ ID NO: 14)

RQIKIWFQNRRMKWKK, (SEQ ID NO: 15)

GLFEAIAGFIENGWEGMIDG, (SEQ ID NO: 16)

GWTLNSAGYLLGKIN, (SEQ ID NO: 17)

RSQSRSRYYRQRQRS, (SEQ ID NO: 18)

LAIPEQEY, (SEQ ID NO: 19)

LGIAEQEY, (SEQ ID NO: 20)

LGIPAQEY, (SEQ ID NO: 21)

LGIPEAEY, (SEQ ID NO: 22)

LGIPEQAY, (SEQ ID NO: 23)

LGIAEAEY, (SEQ ID NO: 24)

LGIPEAAY, (SEQ ID NO: 25)

LGIAEQAY, (SEQ ID NO: 26)

LGIAEAAY, (SEQ ID NO: 27)

LLIILRRRIR KQAHAHSK, (SEQ ID NO: 28)

LKALAALAKKIL, (SEQ ID NO: 29)

KLALKLALKALKAALKLA, (SEQ ID NO: 30)

KETWWETWWTEWSQPKKKRKV, (SEQ ID NO: 31)

DHQLNPAF, (SEQ ID NO: 32)

DPKGDPKG, (SEQ ID NO: 33)

VTVTVTVTVTGKGDPKPD, (SEQ ID NO: 34)

RQIKIWFQNRRMKWKK, (SEQ ID NO: 35)

GRKKRRQRRRPPQ, (SEQ ID NO: 36)

GWTLNSAGYLLGKINLKALAALAKKIL, (SEQ ID NO: 37)

GRKKRRQRRR, (SEQ ID NO: 38)

RRRRRRR, (SEQ ID NO: 39)

RRRRRRRR, (SEQ ID NO: 40)

RRRRRRRRR, (SEQ ID NO: 41)

RRRRRRRRRR, (SEQ ID NO: 42)

RRRRRRRRRRR, and (SEQ ID NO: 43)

YTIWMPENPRPGTPCDIFTNSRGKRASNGGG (SEQ ID NO: 44)
G(R)n wherein n = 2-15 R in the
L- and/or D- form, or a cell permeating fragment thereof.

In some embodiments, the internal phase of liposomes in the provided liposome compositions comprise platinum-cyclodextrin complexes and further comprise a pharmaceutically acceptable carrier such as trehalose. In an additional embodiment, the trehalose is present at about 5% to 20% weight percent of trehalose or any combination of one or more lyoprotectants or cryoprotectants at a total concentration of 5% to 20%.

In some embodiments, the internal phase of liposomes in the provided liposome compositions comprise platinum-polyglutamate complexes and further comprise a pharmaceutically acceptable carrier such as trehalose. In an additional embodiment, the trehalose is present at about 5% to 20% weight percent of trehalose or any combination of one or more lyoprotectants or cryoprotectants at a total concentration of 5% to 20%. In further non-limiting embodiments, liposomes in the provided liposome compositions enclose an interior space (internal phase). In some embodiments, the interior space comprises, but is not limited to, an aqueous solution. In some embodiments, the interior space comprises a therapeutic agent-polyglutamate or therapeutic agent-cyclodextrin complex as provided herein. In additional embodiments, the interior space of the liposome comprises a tonicity agent. In some embodiments. In some embodiments, the concentration (weight percent) of the tonicity agent is 0.1-20%, 1-20%, 0.5-15%, 1-15%, or 1-50%, or any range therein between. In some embodiments, the interior space of the liposome includes a sugar (e.g., trehalose, maltose, sucrose, lactose, mannose, mannitol, glycerol, dextrose, fructose, etc.). In further embodiments, the concentration (weight percent) of the sugar is 0.1-20%, 1-20%, 0.5-15%, 1%-15%, or 1-50%, or any range therein between. In some embodiments, the pH of the interior space of the liposome is from pH 2 to 8, or any range therein between. In some embodiments, the pH of solutions comprising the liposome composition is from pH 5 to 8, or any range therein between. In some embodiments, the pH of solutions comprising the liposome composition is from pH 6 to 7, or any range therein between. In some embodiments, the pH of solutions comprising the liposome composition is from 6 to 7.5, from 6.5 to 7.5, from 6.7 to 7.5, or from 6.3 to 7.0, or any range therein between. In some embodiments, the interior space comprises buffer. In further embodiments, the buffer a buffer selected from HEPES, citrate, or sodium phosphate (e.g., monobasic and/or dibasic sodium phosphate). In some embodiments, the buffer is HEPES. In some embodiments, the buffer is citrate. In some embodiments, the buffer is sodium phosphate (e.g., monobasic and/or dibasic sodium phosphate). In some embodiments, the buffer is at a concentration of 15 to 200 mM, or any range therein between. In yet further embodiments, the buffer is at a concentration of between 5 to 200 mM, 15-200, between 5 to 100 mM, between 15 to 100 mM, between 5 to 50 mM, between 15 to 50 mM, between to 25 mM, between 5 to 20 mM, between 5 to 15 mM, or any range therein between. In some embodiments, the buffer is HEPES at a concentration of 15 to 200 mM, or any range therein between. In some embodiments, the buffer is citrate at a concentration of 15 to 200 mM, or any range therein between. In some embodiments, the buffer is sodium phosphate at a concentration of 15 to 200 mM, or any range therein between. In some embodiments, the interior space of the liposome comprises a total concentration of sodium acetate and calcium acetate of between 5 mM to 500 mM, or 50 mM to 500 mM, or any range therein between.

In some embodiments, the interior phase of liposomes in the provided liposome compositions comprise liposome includes trehalose. In further embodiments, the concentration weight percent of trehalose is 0.1-20%, 1-20%, 0.5-15%, 1%-15%, 5-20%, or 1-50%, or any range therein between. In yet further embodiments, the concentration (weight percent) of trehalose is 1-15%, or any range therein between. In an additional embodiment, the trehalose is present at about 5% to 20% weight percent of trehalose or any combination of one or more lyoprotectants or cryoprotectants at a total concentration of 5% to 20%.

In some embodiments, the internal phase of liposomes in the provided liposome compositions comprises a buffer. In further embodiments, the buffer is HEPES buffer or citrate buffer. In some embodiments, the citrate buffer is at a concentration of between 5 to 200 mM. In some embodiments, the internal phase of the liposome has a pH of between 2.5 to 7.5. In some embodiments, the internal phase of the liposome has a pH of between 2.8 to 6. In additional embodiments, the internal phase of the liposome comprises sodium acetate and/or calcium acetate. In some embodiments, the internal phase of the liposome comprises a total concentration of sodium acetate and calcium acetate of between 5 mM to 500 mM, or 50 mM to 500 mM, or any range therein between.

As discussed above, liposomes of the provided liposome composition may comprise a steric stabilizer. For those embodiments, which incorporate a steric stabilizer, the steric stabilizer may be at least one member selected from the group consisting of polyethylene glycol (PEG), poly-L-lysine (PLL), monosialoganglioside (GM1), poly(vinyl pyrrolidone) (PVP), poly-(acrylamide) (PAA), poly(2-methyl-2-oxazoline), poly(2-ethyl-2-oxazoline), phosphatidyl polyglycerol, poly[N-(2-hydroxypropyl) methacrylamide], amphiphilic poly-N-vinylpyrrolidones, L-amino-acid-based polymer, and polyvinyl alcohol. In some embodiments, the steric stabilizer or the population of steric stabilizer is PEG. In one embodiment, the steric stabilizer is a PEG. In a further embodiment, the PEG has a number average molecular weight (Mn) of 200 to 5000 daltons. These PEG(s) can be of any structure such as linear, branched, star or comb structure and are commercially available.

In some embodiments, the liposome composition comprises liposomes that further contain one or more of an immunostimulatory agent, a detectable marker and a maleimide disposed on at least one of the PEG and the exterior of the liposome.

In some embodiments, liposomes in the provided liposome compositions are targeted pegylated liposomes that including an interior space; a (a) therapeutic agent-polyglutamate complex, or (b) therapeutic agent-cyclodextrin complex, disposed within the interior phase (space); and a targeting moiety comprising a protein with specific affinity for at least one folate receptor, and wherein the targeting moiety disposed at the exterior of the liposome. In some embodiments, the medium is an aqueous solution. In some embodiments, the interior space, the exterior space (e.g., the medium), or both the interior space and the medium contains one or more lyoprotectants or cryoprotectants which are listed above. In some embodiments, the cryoprotectant is mannitol, trehalose, sorbitol, or sucrose.

In some embodiments, internal phase (interior space) of liposomes in the provided liposome compositions contains less than 200,000 complexes of platinum-based chemotherapeutic agents and one or more polyglutamate molecules and/or other polyglutamate molecule complexes provided herein. In some embodiments, the internal phase of the liposome contains between 10,000 to 100,000 complexes of platinum-based chemotherapeutic agents and one or more polyglutamate molecule and/or other polyglutamate molecule complexes provided herein. In further embodiments, the internal phase of the liposome contains between 10,000 to 100,000 complexes of platinum-based chemotherapeutic agents and one or more polyglutamate molecules and/or other polyglutamate molecule complexes provided herein.

In some embodiments, internal phase (interior space) of liposomes in the provided liposome compositions contains less than 200,000 complexes of platinum-based chemotherapeutic agents and cyclodextrin and/or other cyclodextrin complexes provided herein. In some embodiments, the internal phase of the liposome contains between 10,000 to 100,000 complexes of platinum-based chemotherapeutic agents and cyclodextrin and/or other cyclodextrin complexes provided herein. In further embodiments, the internal phase of the liposome contains between 10,000 to 100,000 complexes of platinum-based chemotherapeutic agents and cyclodextrin and/or other cyclodextrin complexes provided herein.

In some embodiments, liposomes in the liposome composition comprise a complex formed by one or more polyglutamate molecules and a therapeutic agent. In some embodiments, the therapeutic agent is a cytotoxic compound or a salt or acid thereof. In a further embodiment, the therapeutic agent is a chemotherapeutic agent or a salt or acid thereof. In another embodiment, the therapeutic agent is a platinum-based chemotherapeutic agent. In another embodiment, the therapeutic agent is a taxane-based drug. In further embodiments, the complex is formed by one or more polyglutamate molecules and a therapeutic agent selected from: gemcitabine, a gemcitabine-based therapeutic agent, doxorubicin, an antifolate, an antifolate-based chemotherapeutic, or a salt or acid, acid or free base form thereof. In additional embodiments, the molar ratio of the polyglutamate molecule-therapeutic agent in the complex is in the range 1-10:1. In some embodiments, the molar ratio of the polyglutamate molecule-therapeutic agent in the complex is: 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, (21-50): 1, or >50:1. In some embodiments, the molar ratio of the polyglutamate molecule-therapeutic agent in the complex is: 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:(21-50), or 1:>50.

In some embodiments, liposomes in the liposome composition comprise a complex formed by a cyclodextrin and a therapeutic agent. In some embodiments, the therapeutic agent is a cytotoxic compound or a salt or acid thereof. In a further embodiment, the therapeutic agent is a chemotherapeutic agent or a salt or acid thereof. In another embodiment, the therapeutic agent is a platinum-based chemotherapeutic agent. In another embodiment, the therapeutic agent is a taxane-based drug. In further embodiments, the therapeutic agent of the cyclodextrin/therapeutic agent complex is a member selected from the group: gemcitabine, a gemcitabine-based therapeutic agent, doxorubicin, an antifolate, an antifolate-based chemotherapeutic, or a salt or acid, acid or free base form thereof. In additional embodiments, the molar ratio of cyclodextrin/therapeutic agent in the complex is in the range 1-10:1. In some embodiments, the molar ratio of αPPMX/therapeutic agent in the complex is 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:(21-50), or 1:>50. In some embodiments, the molar ratio of cyclodextrin/therapeutic agent in the complex is: 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, (21-50):1, or >50:1.

In one embodiment the provided liposome compositions comprise liposomes that are untargeted. That is, the liposome compositions do not have specific affinity towards a specific epitope expressed on the surface of a target cell of interest.

In other embodiments, the provided liposome compositions comprise liposomes that are targeted and that comprise a targeting moiety having an affinity for an epitope (antigen) expressed on the surface of a target cell of interest. The targeted liposome compositions provide further improvements to the efficacy and safety of delivering platinum-based drugs to hyperproliferative cells such as cancer cells, by specifically delivering platinum payloads to the target cell.

In some embodiments, the internal phase of liposomes in the provided liposome compositions comprise platinum-polyglutamate complexes or platinum-cyclodextrin complexes, and the external surface of the liposome comprise a targeting moiety comprising a protein with specific affinity for a surface antigen that is expressed on a target cell of interest (e.g., a folate receptor). Such liposomes may generally be referred to herein as "targeted liposomes," e.g., liposomes including one or more targeting moieties or biodistribution modifiers on the surface of, or otherwise attached to, the liposomes. The targeting moiety of the targeted liposomes can be any moiety or agent that is capable of specifically binding a desired target (e.g., an antigen target expressed on the surface of a cancer cell). In one embodiment, the targeted liposome specifically and preferentially binds to a target on the surface of a target cell, and whereupon the targeted liposome is internalized and the cytotoxic payload of the liposome exerts its cytotoxic effect. In further embodiments, the target cell is a cancer cell, a tumor cell or a metastatic cell. In some embodiments, the targeting liposomes are immunoliposomes.

In some embodiments, the disclosure provides a liposome composition comprising liposomes encapsulating a complex of a (a) platinum-based chemotherapeutic agent or a salt thereof and polyglutamate(s) or (b) platinum-based chemotherapeutic agent or a salt thereof and a cyclodextrin; and a targeting moiety attached to one or both of a PEG and the exterior of the liposome, and wherein the targeting moiety has a specific affinity for a surface antigen on a target cell of interest (e.g., a cancer cell). Such liposomes may generally be referred to herein as "targeted liposomes," e.g., liposomes including one or more targeting moieties or biodistribution modifiers on the surface of, or otherwise attached to, the liposomes. The targeting moiety of the targeted liposomes can be any moiety or agent that is capable of specifically binding a desired epitope or target (e.g., an antigen target expressed on the surface of a target cell of interest). In one embodiment, the targeted liposome specifically and preferentially binds to a target on the surface of a target cell of interest that internalizes the targeted liposome into the cell. In particular embodiments, the target cell is a cancer cell, a tumor cell or a metastatic cell. In some embodiments, the targeted liposome is pegylated.

The term "attach" or "attached" refers, for example, to any type of bonding such as covalent bonding, ionic bonding (e.g., avidin-biotin) bonding by hydrophobic interactions, and bonding via functional groups such as maleimide, or linkers such as PEG. For example, a detectable marker, a steric stabilizer, a liposome, a liposomal component, an immunostimulating agent may be attached to each other directly, by a maleimide functional group, or by a PEG-malemide group The composition and origination of the targeting moiety is non-limiting to the scope of this disclosure. In some embodiments, the targeting moiety attached to the liposome is a polypeptide or peptidomimetic ligand. Peptide and peptidomimetic targeting moieties include those having naturally occurring or modified peptides, e.g., D or L peptides; alpha, beta, or gamma peptides; N-methyl peptides; azapeptides; peptides having one or more amide, i.e., peptide, linkages replaced with one or more urea, thiourea, carbamate, or sulfonyl urea linkages; or cyclic peptides. A peptidomimetic is a molecule capable of folding into a defined three-dimensional structure similar to a natural peptide. In some embodiments, the peptide or peptidomimetic targeting moiety is 2-50 amino acids long, e.g., about 5, 10, 15, 20, 25, 30, 35, 40, 45, or 50 amino acids long In some embodiments, the targeting moiety polypeptide is at least 40 amino acid residues in length. In other embodiments, the targeting moiety polypeptide is at least 50, 60, 75, 100, 125, 150, 175, 200, 250, or 300 amino acid residues in length.

In additional embodiments, the targeting moiety polypeptide such as an antibody or an antigen-binding antibody fragment that binds a target antigen with an equilibrium dissociation constant (Kd) in a range of $0.5 \times 10^{-10}$ to $10 \times 10^{-6}$ as determined using BIACORE® analysis.

In additional embodiments, the targeting moiety is an antibody or a derivative of the antigen binding domain of an antibody that has specific affinity for an epitope on a tumor cell surface antigen of interest expressed on the surface of a target cell.

In further embodiments, the targeting moiety is an antibody or a fragment of an antibody. In additional embodiments, the targeting moiety comprises one or more of an antibody, a humanized antibody, an antigen binding fragment of an antibody, a single chain antibody, a single-domain antibody, a bi-specific antibody, a synthetic antibody, a pegylated antibody, and a multimeric antibody. In additional embodiments, the targeting moiety has the specific affinity for an epitope on a tumor cell surface antigen that is present on a tumor cell but absent or inaccessible on a non-tumor cell. In some embodiments, the targeting moiety further comprises one or more of an immunostimulatory agent, a detectable marker and a maleimide disposed on at least one of the PEG and the exterior of the liposome. In some embodiments, the targeting moiety of the liposome is anionic or neutral. In other embodiments, the targeting moiety of the liposome is cationic. In some embodiments, the target moiety liposome compositions have a diameter in the range of 20 nm to 200 nm. In further embodiments, the liposomes have a diameter in the range of 80 nm to 120 nm.

In some embodiments, the targeting moiety is an antibody or an antibody derivative. In other embodiments, the binding domain of the targeting moiety polypeptide is not derived from the antigen binding domain of an antibody. In some embodiments, the targeting moiety is a polypeptide derived from a binding scaffold selected from the group consisting of a DARPin, affilin, and armadillo repeat, D domain (see, e.g., WO 2016/164308), Z-domain (Affibody), adnectin, lipocalin, affilin, anticalin, knottin, fynomer, atrimer, kunitz domain (see, e.g., WO 2004/063337), CTLA4, or avimer (see, e.g., U.S. Pub. Nos. 2004/0175756, 2005/0053973, 2005/0048512, and 2006/0008844).

In some embodiments, the liposomes comprise a polypeptide targeting moiety such as an antibody or an antibody fragment and the targeting moiety binds a target antigen with an equilibrium dissociation constant (Kd) in a range of $0.5 \times 10^{-10}$ to $10 \times 10^{-6}$ as determined using BIACORE® analysis.

In some embodiments, the disclosure provides a liposome composition wherein the liposome is pegylated and comprises a targeting moiety attached to one or both of a PEG and/or the exterior of the liposome, and wherein the targeting moiety has a specific affinity for a surface antigen on a target cell of interest. In some embodiments, the targeting moiety is a polypeptide. In further embodiments, the targeting moiety is an antibody or a fragment of an antibody. In additional embodiments, the targeting moiety comprises one or more of an antibody, a humanized antibody, an antigen binding fragment of an antibody, a single chain antibody, a single-domain antibody, a bi-specific antibody, a synthetic antibody, a pegylated antibody, and a multimeric antibody. In additional embodiments, the targeting moiety has the specific affinity for an epitope on a tumor cell surface antigen that is present on a tumor cell but absent or inaccessible on a non-tumor cell. In some embodiments, the targeting moiety-liposome further comprises one or more of an immunostimulatory agent, a detectable marker and a maleimide disposed on at least one of the PEG and the exterior of the liposome. In some embodiments, the targeting moiety-liposome is anionic or neutral. In other embodiments, the targeting moiety-liposome is cationic. In additional embodiments, the targeting moiety—liposomes have a diameter in the range of 20 nm to 200 nm. In further embodiments, the liposomes have a diameter in the range of 80 nm to 120 nm.

In some embodiments, the targeting moiety is an antibody or antigen binding portion of an antibody that specifically binds a target expressed on the surface of a target cell of interest. In some embodiments, the targeting moiety is a full-length antibody. In some embodiments, the targeting moiety is an antigen binding portion of an antibody. In some embodiments, the targeting moiety is an scFv. In other embodiments, the targeting moiety is a Fab. In some embodiments, the targeting moiety comprises a binding domain derived from the antigen binding domain of an antibody (e.g., an scFv, Fab, Fab', F(ab')2, an Fv fragment, a disulfide-linked Fv (sdFv), a Fd fragment consisting of VH and CH1 domains, an scFv, a minibody, a BiTE, a Tandab, a diabody ((VL-VH)$_2$ or (VH-VL)$_2$), a single domain antibody (e.g., an sdAb such as a nanobody (either VL or VH)), and a camelid VHH domain) In some embodiments, the targeting moiety comprises one or more complementarity determining regions (CDRs) of antibody origin. Examples of suitable antibody-based targeting moieties for the disclosed targeted liposomes include a full-length human antibody, a humanized antibody, a chimeric antibody, an antigen binding fragment of an antibody, a single chain antibody, a single-domain antibody, a bi-specific antibody, a synthetic antibody, a pegylated antibody and a multimeric antibody. The antibody of the provided targeted liposomes can have a combination of the above characteristics. For example, a humanized antibody can be an antigen binding fragment and can be pegylated and multimerized as well.

The term "humanized antibody" refers to forms of non-human (e.g., murine) antibodies that are specific immunoglobulin chains, chimeric immunoglobulins, or fragments thereof that contain minimal non-human (e.g., murine) sequences. Typically, humanized antibodies are human immunoglobulins in which residues from the complementary determining region (CDR) are replaced by residues from the CDR of a non-human species (e.g. mouse, rat, rabbit, and hamster) that have the desired specificity, affinity, and capability (Jones et al., Nature 321:522-525 (1986); Riechmann et al., Nature 332:323-327 (1988); Verhoeyen et al., Science 239:1534-1536 (1988)). In some instances, the Fv framework region (FR) residues of a human immunoglobulin are replaced with the corresponding residues in an antibody from a non-human species that has the desired specificity, affinity, and capability. The humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. Nos. 5,225,539 and 5,639,641.

In further embodiments, the targeting moiety has specific affinity for an epitope on a surface antigen of a target cell of interest. In some embodiments, the target cell is a cancer cell. In some embodiments, the target cell is a tumor cell. In other embodiments, the target cell is an immune cell.

In some embodiments, the targeting moiety-liposome comprises a polypeptide targeting moiety such as an antibody, an antigen binding portion of an antibody (e.g., a Fab, scFv and a single domain antibody), an aptamer, an affibody and the targeting moiety has a specific affinity for a target antigen selected from the group consisting of GONMB, CD56, TACSTD2 (TROP2), CEACAM5, Folate receptor-α, Folate receptor-β, Folate receptor-δ, Mucin 1, STEAP1, Mesothelin, Nectin 4, ENPP3, Guanylyl cyclase C (GCC), SLC44A4, NaPi2b, CD70 (TNFSF7), CA9 (Carbonic anhydrase), 5T4 (TPBG), SLTRK6, SC-16, Tissue factor, LIV-1 (ZIP6), CGEN-15027, P-Cadherin, Fibronectin Extra-domain B (ED-B), VEGFR2 (CD309), Tenascin, Collagen IV, Periostin, endothelin receptor, HER 2, EGFR, CD30, CD79b, CD19, CD138, CD74, CD37, CD19, CD22, CD33, and CD98.

In some embodiments, the targeting moiety-liposome comprises a polypeptide targeting moiety such as an antibody or antigen binding portion of an antibody (e.g., a Fab, scFv and a single domain antibody), an aptamer, or an affibody, and the targeting moiety binds a target antigen with an equilibrium dissociation constant (Kd) in a range of $0.5 \times 10^{-10}$ to $10 \times 10^{-6}$ as determined using BIACORE® analysis. In further embodiments, the targeting moiety comprises a polypeptide that specifically binds a folate receptor. In some embodiments, the folate receptor bound by the targeting moiety is one or more folate receptors selected from the group: folate receptor alpha (FR-α), folate receptor beta (FR-β), and folate receptor delta (FR-δ).

In some embodiments, the targeting moiety has specific affinity for an epitope expressed on a tumor cell surface antigen. The term "tumor cell surface antigen" refers to an antigen that is common to a specific hyperproliferative disorder such as cancer. In some embodiments, the targeting moiety has specific affinity for an epitope of a tumor cell surface antigen that is a tumor associated antigen (TAA). A TAA is an antigen that is found on both tumor and some normal cells. A TAA may be expressed on normal cells during fetal development when the immune system is immature and unable to respond or may be normally present at extremely low levels on normal cells but which are expressed at much higher levels on tumor cells. Because of the dynamic nature of tumors, in some instances, tumor cells may express unique antigens at certain stages, and at others also express antigens that are also expressed on non-tumor cells. Thus, inclusion of a certain marker as a TAA does not preclude it being considered a tumor specific antigen. In some embodiments, the targeting moiety has specific affinity for an epitope of a tumor cell surface antigen that is a tumor specific antigen (TSA). A TSA is an antigen that is unique to tumor cells and does not occur on other cells in the body. In some embodiments, the targeting moiety has specific affinity for an epitope of a tumor cell surface antigen expressed on the surface of a cancer including but not limited to primary or metastatic melanoma, thymoma, lymphoma, sarcoma, lung cancer (e.g., NSCLC or SCLC), liver cancer, non-Hodgkin's lymphoma, Hodgkin's lymphoma, leukemias, multiple myeloma, glioblastoma, neuroblastoma, uterine cancer, cervical cancer, renal cancer, thyroid cancer, bladder cancer, kidney cancer, mesothelioma, and adenocarcinomas such as breast cancer, prostate cancer, ovarian cancer, pancreatic cancer, colon cancer and other cancers known in the art. In some embodiments, the targeting moiety has specific affinity for an epitope of a cell surface antigen expressed on the surface of a cell in the tumor microenvironment (e.g., and antigen such as VEGFR and TIE1, or TIE2 expressed on endothelial cells and macrophage, respectively, or an antigen expressed on tumor stromal cells such as cancer-associated fibroblasts (CAFs) tumor infiltrating T cells and other leukocytes, and myeloid cells including mast cells, eosinophils, and tumor-associated macrophages (TAM).

In some embodiments, the targeted liposome comprises a targeting moiety that has specific affinity for an epitope of a cancer or tumor cell surface antigen that is preferentially/differentially expressed on a target cell such as a cancer cell or tumor cell, compared to normal or non-tumor cells, that is present on a tumor cell but absent or inaccessible on a non-tumor cell. For example, in some situations, the tumor antigen is on the surface of both normal cells and malignant cancer cells but the tumor epitope is only exposed in a cancer cell. As a further example, a tumor cell surface antigen may experience a confirmation change in a cancerous state that causes a cancer cell specific epitope to be present. A targeting moiety with specific affinity to an epitope on a targetable tumor cell surface antigen provided herein or otherwise known in the art is useful and is encompassed by the disclosed compositions and methods. In some embodiments, the tumor cell with the tumor cell surface antigen is a cancer cell. Examples of such tumor cell surface antigens include, without limitation folate receptor alpha, folate receptor beta and folate receptor delta.

In further embodiments, the targeting moiety comprises a polypeptide targeting moiety such as an antibody or an antigen-binding antibody fragment and the targeting moiety has binding specificity for a folate receptor. In some embodiments, the targeting moiety binds a folate receptor with an equilibrium dissociation constant (Kd) in a range of $0.5 \times 10^{-10}$ to $10 \times 10^{-6}$ as determined using BIACORE® analysis. In some embodiments, the folate receptor bound by the targeting moiety is one or more folate receptors selected from the group: folate receptor alpha (FR-α), folate receptor beta (FR-β), and folate receptor delta (FR-δ). In a further embodiment, the targeting moiety has specific affinity for at least two antigens selected from the group consisting of folate receptor alpha, folate receptor beta, and folate receptor delta. In another embodiment, the targeting moiety has specific affinity for folate receptor alpha; folate receptor beta; and folate receptor delta.

In some embodiments, the targeting moiety has a specific affinity for an epitope of a cell surface antigen that internalizes the targeting moiety upon binding. Numerous cell surface antigens that internalize binding partners such as antibodies upon binding are known in the art and are envisioned to be binding targets for the targeting moieties expressed on targeted liposomes of the liposome compositions provided herein.

In some embodiments, the targeting moiety has a specific affinity for an epitope of a cell surface antigen selected from the group: GONMB, TACSTD2 (TROP2), CEACAM5, EPCAM, a folate receptor (e.g., folate receptor-α, folate receptor-β or folate receptor-8), Mucin 1 (MUC-1), MUC-6, STEAPI, mesothelin, Nectin 4, ENPP3, Guanylyl cyclase C (GCC), SLC44A4, NaPi2b, CD70 (TNFSF7), CA9 (Carbonic anhydrase), 5T4 (TPBG), SLTRK6, SC-16, Tissue factor, LIV-1 (ZIP6), CGEN-15027, P Cadherin, Fibronectin Extra-domain B (ED-B), VEGFR2 (CD309), Tenascin, Collagen IV, Periostin, endothelin receptor, HER2, HER3, ErbB4, EGFR, EGFRvIII, FGFR1, FGFR2, FGFR3, FGFR4, FGFR6, IGFR-1, FZD1, FZD2, FZD3, FZD4, FZD5, FZD6, FZD7, FZD8, FZD9, FZD10, SMO, CD2, CD3, CD4, CDS, CD6, CD8, CD 11, CD 11a, CD 15, CD 18, CD 19, CD20, CD22, CD26, CD27L, CD28, CD30, CD33, CD34, CD37, CD38, CD40, CD44, CD56, CD70, CD74, CD79, CD79b, CD98, CD105, CD133, CD138, cripto, IGF-1R, IGF-2R, EphA1 an EphA receptor, an EphB receptor, EphA2, EphA3, EphA4, EphA5, EphA6, EphA7, EphA8, EphA1, EphB1, EphB2, EphB3, EphB4, EphB6, an integrin (e.g., integrin αvβ3, αvβ5, or αvβ6), a C242 antigen, Apo2, PSGR, NGEP, PSCA, TMEFF2, endoglin, PSMA, CanAg, CALLA, c-Met, VEGFR-1, VEGFR-2, DDR1, PDGFR alpha., PDGFR beta, TrkA, TrkB, TrkC, UFO, LTK, ALK, Tie1, Tie2, PTK7, Ryk, TCR, NMDAR, LNGFR, and MuSK.

In some embodiments, the targeting moiety has a specific affinity for a cell surface antigen(s) derived, from or determined to be expressed on, a specific subject's cancer (e.g., tumor) such as a neoantigen.

In some embodiments, the targeting moiety has a specific affinity for an epitope of a cell surface antigen selected from the group consisting of mannose-6-phosphate receptor, transferrin receptor, and a cell adhesion molecule (CAM). In further embodiments, the targeting moiety has a specific affinity for an epitope of a CAM is selected from the group consist of: intercellular adhesion molecule (ICAM), platelet-endothelial cell adhesion molecule (PECAM), activated leukocyte cell adhesion molecule (ALCAM), B-lymphocyte cell adhesion molecule (BL-CAM), vascular cell adhesion molecule (VCAM), mucosal vascular addressin cell adhesion molecule (MAdCAM), CD44, LFA-2, LFA-3, and basigin.

A discussed herein, folate receptors (FRs) are distinct from reduced folate carriers (RFCs) and exploit different pathways for bringing folates and antifolates into cells. In some embodiments, the targeting moiety specifically binds a folate receptor. In further embodiments, the targeting moiety specifically binds a folate receptor selected from folate receptor alpha, folate receptor beta and folate receptor delta. Antibodies to folate receptor alpha can routinely be generated using techniques known in the art. Moreover, the sequences of numerous anti-folate receptor antibodies are in the public domain and/or commercially available and are readily obtainable.

Murine antibodies against folate receptor are examples of antibodies that can be used as targeting moieties of the disclosed targeted liposome is a murine antibody against folate receptor. The sequence of these antibodies are known and are described, for example, in U.S. Pat. Nos. 5,646,253; 8,388,972; 8,871,206; and 9,133,275 and in Intl. Appl. Nos. PCT/US2011/056966 and PCT/US2012/046672. For example, based on the sequences disclosed already in the public domain, the gene for the antibodies can be synthesized and placed into a transient expression vector and the antibody was produced in HEK-293 transient expression system. The antibody can be a complete antibody, a Fab, or any of the various antibody variations discussed herein or otherwise known in the art.

In some embodiments, the targeted liposome contains from 1 to 1,000, or more than 1,000, targeting moieties on its surface. In some embodiments, the targeted liposome contains from 30 to 1,000, 30 to 500, 30 to 250 or 30-200, targeting moieties, or any range therein between. In some embodiments, the targeted liposome contains less than 220 targeting moieties, less than 200 targeting moieties, or less than 175 targeting moieties. In some embodiments, the targeting moiety is non-covalently bonded to the outside of the liposome (e.g., via ionic interaction or a GPI anchor).

In some embodiments, the molecules on the outside of the targeted liposome include a lipid, a targeting moiety, a steric stabilizer (e.g., a PEG), a maleimide, and a cholesterol. In some embodiments, the targeting moiety is covalently bound via a maleimide functional group. In some embodiments, the targeting moiety is covalently bound to a liposomal component or a steric stabilizer such as a PEG molecule. In some embodiments, all the targeting moieties of the liposome are bound to one component of the liposome such as a PEG. In other embodiments, the targeting moieties of the targeted liposome are bound to different components of the liposome. For example, some targeting moieties may be bound to the lipid components or cholesterol, some targeting moieties may be bound to the steric stabilizer (e.g., PEG) and still other targeting moieties may be bound to a detectable marker or to another targeting moiety.

In some embodiments, targeted liposomes of the liposome compositions provided herein comprise a targeting moiety that has affinity and specificity (i.e., specifically binds) for an antigen expressed on the surface of a cancer cell. In further some embodiments, the targeting moiety of the targeted liposome has affinity and specificity for one or more antigens selected from the group consisting of folate receptor alpha, folate receptor beta, and folate receptor delta. In one embodiment, the targeting moiety has specific affinity (i.e., specifically binds) an antigen selected from the group consisting of folate receptor alpha, folate receptor beta, and folate receptor delta. In a further embodiment, the targeting moiety has specific affinity for at least two antigens selected from the group consisting of folate receptor alpha, folate receptor beta, and folate receptor delta. In another embodiment, the targeting moiety has specific affinity for three antigens which are, for example, folate receptor alpha; folate receptor beta; and folate receptor delta. The targeting moiety may have affinity and specificity to an epitope of the antigen because sometimes a targeting moiety does not bind the complete antigen but just an epitope of many epitopes in an antigen.

In some embodiments, targeted liposomes of the liposome compositions provided herein comprise a targeting moiety that is an antibody or a derivative of the antigen binding domain of an antibody that has specific affinity for an epitope on a tumor cell surface antigen that is present on a tumor cell but absent or inaccessible on a non-tumor cell. For example, in some situations, the tumor antigen is on the surface of both normal cells and malignant cancer cells but the tumor epitope is only exposed in a cancer cell. As a further example, a tumor antigen may experience a confirmation change in cancer causing cancer cell specific epitopes to be present. A targeting moiety with specific affinity to epitopes provided herein are useful and are encompassed by the disclosed compositions and methods. In some embodiments, the tumor cell with the cancer cell specific epitope(s) is a cancer cell. Examples of such tumor cell surface antigens include, folate receptor alpha, folate receptor beta and folate receptor delta.

There are no particular limitations on the mixing amount (mole fraction) of the phospholipids and/or phospholipid derivatives that are used when preparing the liposome. In one embodiment, 10 to 80% relative to the entire liposome membrane composition can be used. In another embodiment, a range of between 30 to 60% can be used.

In addition, there are no particular limitations on the solvent of the liposome internal phase. Exemplary buffer solutions include, without limitation, as phosphate buffer solution, citrate buffer solution, and phosphate-buffered physiological saline solution, and physiological saline water. In the case where buffer solution is used as solvent, it is preferable that the concentration of buffer agent be 5 to 300 mM, 10 to 100 mM, or any range in between. There are also no particular limitations on the pH of the liposome internal phase. In some embodiments, the liposome internal phase has a pH between 2 and 11, 3 and 9, 4 and 7, 4 and 5, 2.5 and 7.5, 2.8 and 6.0 and any range in between inclusive.

There are no particular limitations on the solvent of the liposome composition in the instances where the liposome composition is a liquid formulation. Representative examples include, without limitation, buffer solutions such as phosphate buffer solution, citrate buffer solution, and phosphate-buffered physiological saline solution, and physiological saline water. There are also no particular limitations on the pH of the liposome external phase of the liposome composition. In some embodiments, such as H is between 2 and 11, 3 and 10, 4 and 9, 7.4, 7.0, or any pH higher than that of the liposome internal phase.

In some embodiments, the liposome composition comprises an excipient. In additional embodiments, the excipient comprises more than one different excipient. In further embodiments, the excipient comprises a sugar or an alcohol. In some embodiments, the pharmaceutically excipient is a sugar selected from the group: a monosaccharide such as, glucose, galactose, mannose, fructose, inositol, ribose, or xylose; a disaccharides such as, lactose, sucrose, cellobiose, trehalose, and maltose; a trisaccharides such as, raffinose and melezitose; and a polysaccharide. In some embodiments, the pharmaceutically excipient is a sugar alcohol selected from the group: erythritol, xylitol, sortibol, mannitol and maltitol; polyvalent alcohols such as glycerin, diglycerin, polyglycerin, propylene glycol, polypropylene glycol, ethylene glycol, diethylene glycol, triethylene glycol, polyethylene glycol, ethylene glycol monoalkylether, diethylene glycol monoalkylether, and 1,3-butylene glycol. In further embodiments, the solvent of the liposome composition comprises a combination of sugar and alcohol excipients.

For purposes of stable long-term storage of liposomes dispersed in solvent, it is preferable to eliminate the electrolyte in the solvent as much as possible. Moreover, from the standpoint of chemical stability of the lipids, it is preferable to set the pH of the solvent from acidic to the vicinity of neutral (pH 3.0 to 8.0), and to remove dissolved oxygen through nitrogen bubbling. Representative examples of liquid stabilizers include, without limitation, normal saline, isotonic dextrose, isotonic sucrose, Ringer's solution, and Hanks' solution. A buffer substance can be added to provide pH optimal for storage stability. For example, pH between about 6.0 and about 7.5, more preferably pH about 6.5, is optimal for the stability of liposome lipid bilayer lipids, and provides for excellent retention of the entrapped entities. Histidine, hydroxyethylpiperazine-ethylsulfonate (HEPES), morpholipoethylsulfonate (MES), succinate, tartrate, and citrate, typically at 2-20 mM concentration, are exemplary buffer substances. Other suitable carriers include, e.g., water, buffered aqueous solution, 0.4% NaCl, 0.3% glycine, and the like.

The tonicity of the liposome composition can be adjusted to the physiological level of 0.25-0.35 mol/kg with glucose or a more inert compound such as lactose, sucrose, mannitol, or dextrin. These compositions can routinely be sterilized using conventional, known sterilization techniques, e.g., by filtration. The resulting aqueous solutions can be packaged for use or filtered under aseptic conditions and lyophilized, the lyophilized preparation being combined with a sterile aqueous medium prior to administration. There are no particular limitations on the concentration of the sugar contained in the liposome composition, but in a state where the liposome is dispersed in a solvent (liquid), for example, it is preferable that the concentration of sugar be 2 to 20% (W/V), and 5 to 10% (W/V) is more preferable. With respect to the concentration of polyvalent alcohol, 1 to 5% (W/V) is preferable, and 2 to 2.5% (W/V) is more preferable.

Solid formulations of the provided liposome compositions can also include pharmaceutical excipients. Such components can include, for example, sugar, such as monosaccharides such as glucose, galactose, mannose, fructose, inositole, ribose, and xylose; disaccharides such as lactose, sucrose, cellobiose, trehalose, and maltose; trisaccharides such as raffmose and melezitose; polysaccharides such as cyclodextrin; and sugar alcohols such as erythritol, xylitol, sorbitol, mannitol, and maltitol. More preferable are blends of glucose, lactose, sucrose, trehalose, and sorbitol. Even more preferable are blends of lactose, sucrose, and trehalose. By this refers to, solid formulations can be stably stored over long periods. When frozen, it is preferable that solid formulations contain polyvalent alcohols (aqueous solutions) such as glycerin, diglycerin, polyglycerin, propylene glycol, polypropylene glycol, ethylene glycol, diethylene glycol, triethylene glycol, polyethylene glycol, ethylene glycol monoalkylether, diethylene glycol monoalkylether and 1,3-butylene glycol. With respect to polyvalent alcohols (aqueous solutions), glycerin, propylene glycol, and polyethylene glycol are preferable, and glycerin and propylene glycol are more preferable.

Therapeutic Agents

In some embodiments, the disclosure provides a composition comprising a delivery vehicle, such as a liposome composition that comprises a pegylated liposome encapsulating a complex of a therapeutic agent and (a) one or more polyglutamate molecule(s), or (b) a cyclodextrin.

There are no particular limitations on the therapeutic agent that is complexed with the polyglutamate molecules or cyclodextrin in the liposome compositions disclosed herein as long as the therapeutic agent is capable of being complexed with the polyglutamate molecules or cyclodextrin and encapsulated in a liposome in a manner sufficient to deliver an effective amount of the complexed therapeutic agent to a target cell of interest. For example, it is known that α-cyclodextrin has an internal phase pore diameter size of 0.45-0.6, β-cyclodextrin has an internal phase pore diameter size of 0.6 to 0.8 nm, and γ-cyclodextrin has an internal phase pore diameter size of 0.8 to 0.95 nm. The cyclodextrin can be chosen to match the size of the therapeutic agent to allow for encapsulation. With respect to the molecular weight of the therapeutic agent, a range of 100 to 2,000 daltons is preferable.

As described above, modifications to the non-carbon cyclodextrin groups (e.g., hydroxyl groups) can be selected to modulate intermolecular interactions between the cyclodextrin and the therapeutic agent to thereby modulate the stability, bioavailability, toxicity, and efficacy of the complexed therapeutic agent.

In some embodiments, the therapeutic agent is an antiproliferative/antineoplastic drug. In some embodiments, the therapeutic agent is a member selected from the group: an alkylating agent, an antimetabolite, an antibiotic, an antitimitotic agent, a proteasome inhibitor, and a topoisomerase inhibitor. In further embodiments, the therapeutic agent is a member selected from the group consisting of cyclophosphamide, bendamustin, melphalan, chlorambucil, nitrogen mustard, temozolamide, busulphan, a nitrosourea, gemcitabine, an antifolate, a fluoropyrimidine, 5-fluorouracil, tegafur, raltitrexed, methotrexate, pemetrexed, cytosine arabinoside, hydroxyurea, an anthracycline (e.g., adriamycin, bleomycin, doxorubicin, daunomycin, epirubicin, idarubicin, mitomycin-C, dactinomycin and mithramycin), a vinca alkaloid (e.g., vincristine, vinblastine, vindesine and vinorelbine), a taxoid (e.g., taxol, taxotere, and a polokinase inhibitor); carfilzomib, bortezomib, and a epipodophyllotoxin (e.g., etoposide, teniposide, amsacrine, topotecan, mitoxantrone and camptothecin.

Gemcitabine

In particular embodiments, the therapeutic agent is gemcitabine (dFdC) or a gemcitabine-based therapeutic agent. Gemcitabine is a marketed anti-metabolic nucleoside analog prodrug used first line to treat various solid tumors including non-small-cell lung cancer and pancreatic cancer. Gemcitabine is hydrophilic and relies on nucleoside transporters to cross cell membranes. After entering the cell, gemcitabine (dFdC) is converted into gemcitabine monophosphate (dFdCMP) by deoxycytidine kinase (DCK) during a crucial and rate-limiting step. Subsequently, two more phosphates are added by other enzymes to form pharmacologically active gemcitabine triphosphate (dFdCTP), which competes with the natural substrates for incorporation into DNA and inhibits nucleotide metabolism.

The development of resistance and systemic toxicity often occur when the intracellular conversion of gemcitabine to its active phosphorylated form is not efficient. Unfortunately, phosphorylated gemcitabine-based agents are generally known to be unstable and unable to permeate cell membranes. Moreover, as reflected by the gemcitabine label, the systemic toxicities associated with gemcitabine treatment include the suppression of bone marrow function, the loss of white blood cells, red blood cells, and platelets, and loss of red blood cells, and severe lung conditions like pulmonary edema, pneumonia, and adult respiratory distress syndrome, among others.

As used herein, the term "gemcitabine" refers to the stable salts, acids and free base forms of gemcitabine (2'-Deoxy-2',2'-difluoro-D-cytidine-5'-O-[phenyl (benzoxy-L-alaninyl)] phosphate (dFdC)) and metabolites of gemcitabine as represented in formula IV.

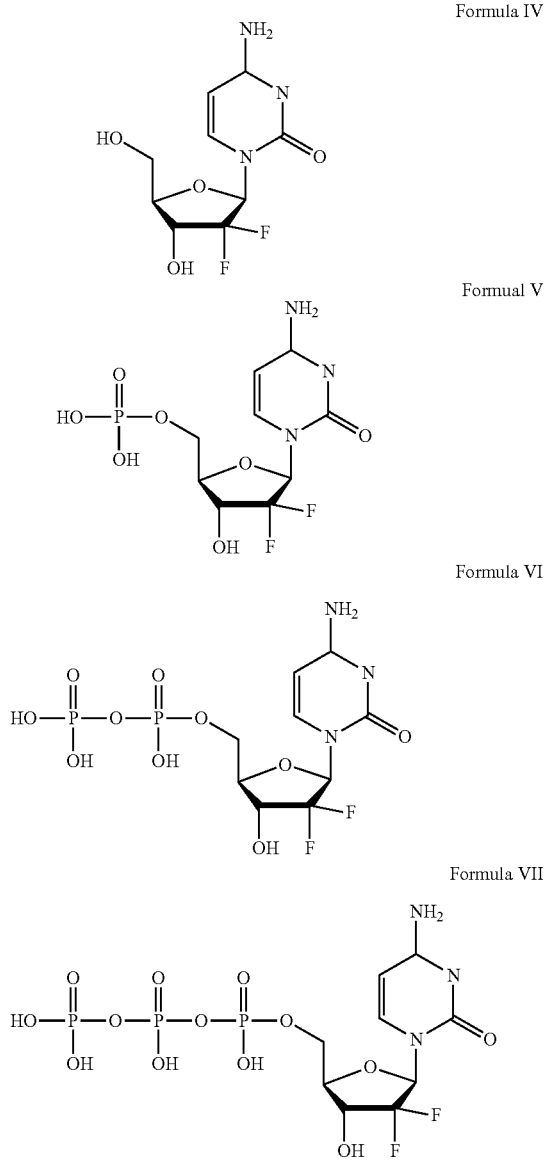

Formula IV

Formual V

Formula VI

Formula VII

In one aspect, the disclosure provides compositions comprising a complex containing a gemcitabine and (a) cyclodextrin or (b) a cationic therapeutic agent. In some embodiments, the cationic therapeutic agent is a platinum-based drug. In some embodiments, the gemcitabine-platinum-based drug complex comprises cisplatin or a salt thereof. In some embodiments, the platinum-based drug complex comprises oxaliplatin, or a salt thereof.

As used herein, the term "gemcitabine-based liposome composition" refers a liposome compositions that contains a complex of an gemcitabine-based chemotherapeutic agent (e.g., dFdC and dFdCTP) and a cyclodextrin, and/or a liposome compositions that contains a complex of an gemcitabine-based chemotherapeutic agent and a cyclodextrin and that also contains a complex of a platinum-based chemotherapeutic agent and a cyclodextrin, unless otherwise indicated. In some embodiments, the platinum-based drug complex comprises stratoplatin, paraplatin, platinol, cycloplatin, dexormaplatin, spiroplatin, picoplatin, triplatin, tetraplatin, iproplatin, ormaplatin, zeniplatin, platinum-triamine, traplatin, enloplatin, JM-216, 254-S, NK121, CI-973, DWA 2114R, NDDP, or dedaplatin, or a salt thereof. Compositions comprising delivery vehicles such as liposomes that contain/encapsulate the therapeutic agent complexes are also provided, as are methods of making and using the provided compositions to treat hyperproliferative diseases such as cancer. In some embodiments, the disclosure provides liposome compositions that comprise a liposome encapsulating a complex of a platinum-based chemotherapeutic agent (e.g., cisplatin and oxaliplatin, or a salt thereof) and one or more gemcitabine molecules (e.g., dFdC and dFdCTP).

In some embodiments, the gemcitabine-based therapeutic agent is gemcitabine (dFdC)(including stable salt and free base forms of gemcitabine). In some embodiments, the gemcitabine-based therapeutic agent is a phosphorylated gemcitabine (including stable salt and free base forms of phosphorylated gemcitabine). In some embodiments, the gemcitabine-based therapeutic agent is gemcitabine monophosphate (dFdCMP)(including stable salt and free base forms thereof). In some embodiments, the gemcitabine-based therapeutic agent is gemcitabine diphosphate (dFdCDP)(including stable salt and free base forms thereof). In some embodiments, the gemcitabine-based therapeutic agent is gemcitabine triphosphate (dFdCTP)(including stable salt and free base forms thereof). These liposome compositions provide improvements to the efficacy and safety of delivering gemcitabine-based agents to cancer cells by providing the preferential delivery of a more cytotoxic payload (e.g., phosphorylated gemcitabine such as dFdCMP, dFdCDP, and dFdCTP) compared to the cytotoxicity of the corresponding gemcitabine-based agent delivered in its uncomplexed and non-liposome encapsulated state.

In a distinct aspect, the disclosure provides liposome compositions that contain liposomes encapsulating a complex of a gemcitabine-based chemotherapeutic agent and a cyclodextrin such as a derivatized beta cyclodextrin. In some embodiments, the gemcitabine-based therapeutic agent is gemcitabine (dFdC)(including stable salt and free base forms of gemcitabine). In some embodiments, the gemcitabine-based therapeutic agent is a phosphorylated gemcitabine (including stable salt and free base forms of phosphorylated gemcitabine). In some embodiments, the gemcitabine-based therapeutic agent is gemcitabine monophosphate (dFdCMP)(including stable salt and free base forms thereof). In some embodiments, the gemcitabine-based therapeutic agent is gemcitabine diphosphate (dFdCDP)(including stable salt and free base forms thereof). In some embodiments, the gemcitabine-based therapeutic agent is gemcitabine triphosphate (dFdCTP)(including stable salt and free base forms thereof). These liposome compositions provide improvements to the efficacy and safety of delivering gemcitabine-based agents to cancer cells by providing the preferential delivery of a more cytotoxic payload (e.g., phosphorylated gemcitabine such as dFdCMP, dFdCDP, and dFdCTP) compared to the cytotoxicity of the corresponding gemcitabine-based agent delivered in its uncomplexed and non-liposome encapsulated state.

Accordingly, in one embodiment, the disclosure provides a liposome composition comprising liposomes encapsulating a complex of a gemcitabine-based agent and a cyclodextrin. In some embodiments, the liposomes are pegylated. In some embodiments, the gemcitabine-based agent is gemcitabine (dFdC) (including stable salt and free base forms of gemcitabine). In some embodiments, the gemcitabine-based agent is a phosphorylated gemcitabine (including stable salt and free base forms of phosphorylated gemcitabine). In some embodiments, the gemcitabine-based therapeutic agent is gemcitabine monophosphate (dFdCMP) (including stable salt and free base forms thereof). In some embodiments, the gemcitabine-based therapeutic agent is gemcitabine diphosphate (dFdCDP) (including stable salt and free base forms thereof). In some embodiments, the gemcitabine-based therapeutic agent is gemcitabine triphosphate (dFdCTP) (including stable salt and free base forms thereof).

The cyclodextrin complexed with the gemcitabine-based therapeutic agent in the provided liposome compositions can be derivatized or underivatized. In some embodiments, the cyclodextrin is derivatized. In further embodiments, the cyclodextrin is a derivatized beta-cyclodextrin (e.g., a hydroxypropyl beta-cyclodextrin (HP-beta-CD), and a sulfobutyl ether beta-CD (SBE)-beta-cyclodextrin). In some embodiments, the cyclodextrin is a derivatized beta-cyclodextrin comprising: 1, 2, 3, 4, 5, 6, 7, 8, 9, 10, or more 2-hydroxylpropyl-3- group substitutions of hydroxy groups; or 1, 2, 3, 4, 5, 6, 7, 8, 9, 10, or more sulfoalkyl ether group substitutions of hydroxy groups. In further embodiments, the cyclodextrin is a derivatized beta-cyclodextrin comprising: 1, 2, 3, 4, 5, 6, 7, 8, 9, 10, or more sulfobutyl ether group substitutions of hydroxy groups.

In some embodiments, the cyclodextrin complexed with the gemcitabine-based therapeutic agent is a derivatized cyclodextrin of Formula I:

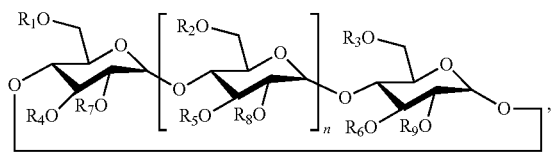

wherein: n is 4, 5, or 6; and wherein $R_1$, $R_2$, $R_3$, $R_4$, $R_5$, $R_6$, $R_7$, $R_8$, and $R_9$ are each, independently, —H, a straight chain or branched $C_1$-$C_8$-alkylene group, a 2-hydroxylpropyl-3- group; or an optionally substituted straight-chain or branched $C_1$-$C_6$ group, wherein at least one of $R_1$, $R_2$, $R_3$, $R_4$, $R_5$, $R_6$, $R_7$, $R_8$ and $R_9$ is a straight-chain or branched $C_1$-$C_8$-alkylene group or a 2-hydroxylpropyl-3- group.

In some embodiments, the cyclodextrin complexed with the gemcitabine-based therapeutic agent is a derivatized cyclodextrin of Formula II:

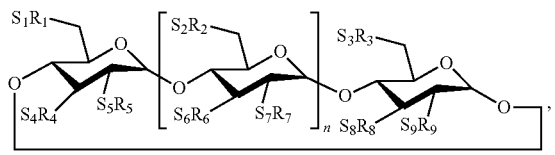

wherein: n is 4, 5, or 6; and wherein $R_1$, $R_2$, $R_3$, $R_4$, $R_5$, $R_6$, $R_7$, $R_8$, and $R_9$ are each, independently, —O— or a —O—($C_2$-$C_6$ alkylene)-$SO_3^-$ group; wherein at least one of $R_1$ and $R_2$ is independently a —O—($C_2$-$C_6$ alkylene)-$SO_3^-$ group; and $S_1$, $S_2$, $S_3$, $S_4$, $S_5$, $S_6$, $S_7$, $S_8$, and $S_9$ are each, independently, a —H or a H or a pharmaceutically acceptable cation. In further embodiments, the wherein the pharmaceutically acceptable cation is selected from: an alkali metal such as $Li^+$, $Na^+$, or $K^+$; an alkaline earth metal such as $Ca^{+2}$, or $Mg^{+2}$, and ammonium ions and amine cations such as the cations of ($C_1$-$C_6$)-alkylamines, piperidine, pyrazine, ($C_1$-$C_6$)-alkanolamine and ($C_4$-$C_8$)-cycloalkanolamine.

In some embodiments, the liposomes in the liposome composition comprise between 100 to 100,000 gemcitabine-based therapeutic agent/cyclodextrin complexes. In additional embodiments, the liposome composition comprises liposomes that have a diameter in the range of 20 nm to 200 nm. In additional embodiments, the liposome composition comprises liposomes that have a diameter in the range of 20 nm to 200 nm. In some embodiments, liposomes in the composition comprise between 100 to 100,000 gemcitabine molecules. In some embodiments, liposomes in the composition are anionic or neutral. In further embodiments, liposomes in the composition have a zeta potential that is less than or equal to zero. In further embodiments, liposomes in the composition has a zeta potential that is between 0 to −150 mV. In other embodiments, liposomes in the composition are cationic. In further embodiments, liposomes in the composition have a zeta potential that is between 1 and 100 mV.

The liposomes in the provided gemcitabine-based liposome compositions are preferably pegylated. In some embodiments, the polyethylene glycol of the liposomes has a number average molecular weight (Mn) of 200 to 5000 daltons. The internal phase of the liposome has a pH in the range of 2.8-6.8. In some embodiments, the internal phase of the liposome comprises trehalose (e.g., 5% to 20% weight of trehalose).

In additional embodiments, the gemcitabine-based liposome composition comprises liposomes that contain a targeting moiety. In some embodiments, the targeting moiety is attached to one or both of a PEG and the exterior of the liposome. In additional embodiments, the targeting moiety has a specific affinity for a surface antigen on a target cell of interest. In some embodiments, the targeting moiety is a polypeptide. In additional embodiments, the targeting moiety is an antibody, a humanized antibody, an antigen binding fragment of an antibody, a single chain antibody, a single-domain antibody, a bi-specific antibody, a synthetic antibody, a pegylated antibody, or a multimeric antibody. In some embodiments, the liposome composition comprises liposomes that contain from 30 to 500 targeting moieties. In further embodiments, the liposome composition comprises liposomes that contain from 30 to 200 targeting moieties.

In some embodiments, the gemcitabine-based liposome composition comprises liposomes that further contain one or more of an immunostimulatory agent, a detectable marker and a maleimide disposed on at least one of the PEG and the exterior of the liposome.

In some embodiments, the disclosed gemcitabine-based liposome compositions further comprise a second complex formed by a therapeutic agent or a salt thereof, and a cyclodextrin. In some embodiments, the therapeutic agent of the second complex is a member selected from the group: gemcitabine, and doxorubicin (including salts and free forms thereof). The cyclodextrin of the second complex in the gemcitabine-based liposome compositions can be derivatized or underivatized. In some embodiments, the cyclodextrin is derivatized. In further embodiments, the cyclodextrin is a derivatized beta-cyclodextrin (e.g., a hydroxypropyl beta-cyclodextrin (HP-beta-CD), and a sulfobutyl ether beta-CD (SBE)-beta-cyclodextrin). In some embodiments, the cyclodextrin of the second complex in the gemcitabine-based liposome composition is a derivatized beta-cyclodextrin comprising: 1, 2, 3, 4, 5, 6, 7, 8, 9, 10, or more 2-hydroxylpropyl-3- group substitutions of hydroxy groups; or 1, 2, 3, 4, 5, 6, 7, 8, 9, 10, or more sulfoalkyl ether group substitutions of hydroxy groups. In further embodiments, the cyclodextrin of the second complex is a derivatized beta-cyclodextrin comprising: 1, 2, 3, 4, 5, 6, 7, 8, 9, 10, or more sulfobutyl ether group substitutions of hydroxy groups.

In some embodiments, the cyclodextrin of the second complex contained in the liposomes of the gemcitabine-based liposome composition (i.e., the complex formed by a therapeutic agent (including a salt and free form thereof), and a cyclodextrin) is a derivatized cyclodextrin of Formula I:

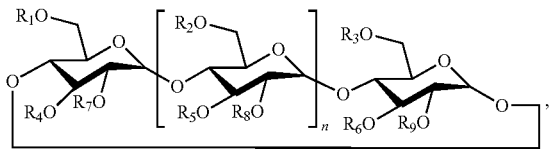

wherein: n is 4, 5, or 6; and wherein $R_1$, $R_2$, $R_3$, $R_4$, $R_5$, $R_6$, $R_7$, $R_8$, and $R_9$ are each, independently, —H, a straight chain or branched $C_1$-$C_8$-alkylene group, a 2-hydroxylpropyl-3- group; or an optionally substituted straight-chain or branched $C_1$-$C_6$ group, wherein at least one of $R_1$, $R_2$, $R_3$, $R_4$, $R_5$, $R_6$, $R_7$, $R_8$ and $R_9$ is a straight-chain or branched $C_1$-$C_8$-alkylene group or a 2-hydroxylpropyl-3- group.

In some embodiments, the cyclodextrin of the second complex contained in the liposomes of the gemcitabine-based liposome composition is a derivatized cyclodextrin of Formula II:

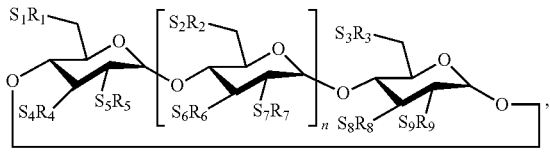

wherein: n is 4, 5, or 6; and wherein $R_1$, $R_2$, $R_3$, $R_4$, $R_5$, $R_6$, $R_7$, $R_8$, and $R_9$ are each, independently, —O— or a —O—($C_2$-$C_6$ alkylene)-$SO_3^-$ group; wherein at least one of $R_1$ and $R_2$ is independently a —O—($C_2$-$C_6$ alkylene)-$SO_3^-$ group; and $S_1$, $S_2$, $S_3$, $S_4$, $S_5$, $S_6$, $S_7$, $S_8$, and $S_9$ are each, independently, a —H or a H or a pharmaceutically acceptable cation. In further embodiments, the wherein the pharmaceutically acceptable cation is selected from: an alkali metal such as $Li^+$, $Na^+$, or $K^+$; an alkaline earth metal such as $Ca^{+2}$, or $Mg^{+2}$, and ammonium ions and amine cations such as the cations of ($C_1$-$C_6$)-alkylamines, piperidine, pyrazine, ($C_1$-$C_6$)-alkanolamine and ($C_4$-$C_8$)-cycloalkanolamine.

In some embodiments, the liposomes in the gemcitabine-based liposome composition comprise between 100 to 100,000 of the second complex formed by the therapeutic agent, and the cyclodextrin. In additional embodiments, the liposome composition comprises liposomes that have a diameter in the range of 20 nm to 200 nm. In some embodiments, liposomes in the composition comprise between 100 to 100,000 gemcitabine-based agent/cyclodextrin complexes. In some embodiments, the cyclodextrin of the second complex is different from the cyclodextrin of the gemcitabine-based agent complex. In some embodiments, the liposome comprises the same cyclodextrin in the second complex and the gemcitabine agent-based complex. In some embodiments, the liposome comprises a cyclodextrin in the second complex that is different from the cyclodextrin of the gemcitabine-based agent complex.

According to some embodiments, the liposomes of the gemcitabine-based liposome compositions comprise oxidized phospholipids. In further embodiments, the phospholipids that are oxidized are a member selected from the group consisting of phosphatidylserines, phosphatidylinositols, phosphatidylethanolamines, phosphatidylcholines and 1-palmytoyl-2-arachidonoyl-sn-gly cero-2-phosphate.

In additional embodiments, the gemcitabine-based liposome compositions comprise oxidized 1-palmitoyl-2-arachidonoyl-sn-glycero-3-phosphorylchloine (OxPAPC). In further embodiments, the oxPAPCs are epoxyisoprostane-containing phospholipids. In further embodiments, the oxPAPC is 1-palmitoyl-2-(5,6-epoxyisoprostane E2)-sn-glycero-3-phosphocholine (5,6-PEIPC), 1-palmitoyl-2-(epoxy-cyclo-pentenone)-sn-glycero-3-phosphorylchloine (PECPC) and/or 1-palmitoyl-2-(epoxy-isoprostane E2)-sn-glycero-4-phosphocholine (PEIPC).

According to some embodiments, the provided gemcitabine-based liposome compositions further comprise one or more of an immunostimulatory agent, a detectable marker and a maleimide, wherein the immunostimulatory agent, the detectable marker or the maleimide is attached to the PEG or the exterior of the liposome. In some embodiments, the immunostimulating agent is at least one a member selected from the group: a protein immunostimulating agent; a nucleic acid immunostimulating agent; a chemical immunostimulating agent; a hapten; and an adjuvant. In some embodiments, the immunostimulating agent is at least one selected from the group: a fluorescein; a fluorescein isothiocyanate (FITC); a DNP; a beta glucan; a beta-1,3-glucan; and a beta-1,6-glucan. In some embodiments, the immunostimulatory agent and the detectable marker is the same. In some embodiments, the liposome composition comprises a hapten. In further embodiments, the hapten comprises one or more of fluorescein or Beta 1,6-glucan.

In some embodiments, the liposomes of the disclosed gemcitabine-based liposome compositions further comprises at least one cryoprotectant selected from the group consisting of mannitol; trehalose; sorbitol; and sucrose. In additional embodiments, the provided liposomal composition is in unit dosage form. In some embodiments, pharmaceutical compositions comprising the liposome compositions disclosed herein are provided.

In some embodiments, the disclosure is directed to the use of the disclosed gemcitabine-based liposome compositions in the treatment of disease. In some embodiments, the disclosure is directed to use of the liposome compositions in the manufacture of a medicament for the treatment of disease.

In some embodiments, the disclosure provides a method of killing a hyperproliferative cell comprising contacting a hyperproliferative cell with a disclosed gemcitabine-based liposome composition. In further embodiments, the hyperproliferative cell is a cancer cell.

In some embodiments, the disclosure provides a method for treating or preventing disease in a subject needing such treatment or prevention, the method comprising administering an effective amount of a gemcitabine-based liposome composition provided herein to a subject in need thereof. In some embodiments, the administration is parenteral. In some embodiments, the administration is intravenous. In some embodiments, the administration is subcutaneous In additional embodiments, the disclosure provides a method for treating cancer in a subject, comprising administering an effective amount of a gemcitabine-based liposome composition disclosed herein to a subject having or at risk of having cancer. In further embodiments, the cancer is a member selected from the group: lung cancer, pancreatic cancer, breast cancer, ovarian cancer, prostate cancer, head and neck cancer, gastric cancer, gastrointestinal cancer, colorectal cancer, esophageal cancer, cervical cancer, liver cancer, kidney cancer, biliary duct cancer, gallbladder cancer, bladder cancer, sarcoma (e.g., osteosarcoma), brain cancer, central nervous system cancer, and melanoma; and a hematologic malignancy such as for example, a leukemia, a lymphoma and other B cell malignancies, myeloma and other plasma cell dyscrasias. In some embodiments, the administration is parenteral. In some embodiments, the administration is intravenous. In some embodiments, the administration is subcutaneous.

In other embodiments, the disclosure provides a method for treating cancer in a subject, comprising administering an effective amount of a gemcitabine-based liposome composition to a tumor expressing an antigen on its surface, the method comprising: administering a gemcitabine-based liposome composition disclosed herein to a subject having a tumor expressing the antigen in an amount to deliver a therapeutically effective dose of the liposome composition to the tumor. In some embodiments, the administration is parenteral. In some embodiments, the administration is intravenous. In some embodiments, the administration is subcutaneous.

A method for treating cancer that comprises administering an effective amount of a gemcitabine-based liposome composition disclosed herein to a subject, wherein the liposome comprises a targeting moiety with specific affinity for an antigen expressed on the surface of a cancer cell, and wherein the subject has or is at risk of having a cancer cell that expresses the antigen. In further embodiments, the antigen is a folate receptor. In some embodiments, the administration is parenteral. In some embodiments, the administration is intravenous. In some embodiments, the administration is subcutaneous.

Also provided is maintenance therapy that comprises administering an effective amount of a gemcitabine-based liposome composition disclosed herein to a subject that is undergoing or has undergone cancer therapy. In some embodiments, the administration is parenteral. In some embodiments, the administration is intravenous. In some embodiments, the administration is subcutaneous.

Doxorubicin

In additional particular embodiments, the therapeutic agent is doxorubicin (DOX). Doxorubicin is an anthracyline drug routinely used in the treatment of several cancers including breast, lung, gastric, bladder, ovarian, thyroid, non-Hodgkin's and Hodgkin's lymphoma, acute lymphocytic leukemia, multiple myeloma, sarcoma (e.g., Kaposi's sarcoma), and pediatric cancers. However, its clinical application is limited due to severe side effects and the accompanying drug resistance. In particular, a major limitation for the use of doxorubicin is cardiotoxicity, with the total cumulative dose being the only criteria currently used to predict the toxicity. Doxorubicin is often used together with other chemotherapy agents. Commonly used doxorubicin-containing regimens include AC (adriamycin, cyclophosphamide), TAC (taxotere, AC), ABVD (Adriamycin, bleomycin, vinblastine, dacarbazine), BEACOPP, CHOP (cyclophosphamide, hydroxydaunorubicin, vincristine, prednisone) and FAC (5-fluorouracil, adriamycin, cyclophosphamide).

A pegylated (polyethylene glycol coated) liposome-encapsulated form of doxorubicin, is sold as DOXIL®. This product was developed to treat Kaposi's sarcoma, an AIDS-related cancer that causes the growth of lesions under the skin, and in the lining of the mouth, nose and throat. However, leakage of the doxorubicin in Doxil has been reported to be associated with uncomfortable and painful adverse events that include redness, tenderness, and peeling of the skin.

As used herein, the term "doxorubicin" refers to the stable salts, acids and free base forms of doxorubicin (e.g., doxorubicin HCl). In some embodiments, the disclosure the disclosure provides compositions comprising a complex containing a doxorubicin and (a) one or more polyglutamate molecules, or (b) cyclodextrin.

As used herein, the term "doxorubicin-based liposome composition" refers a liposome compositions that contains a complex of an antifolate-based chemotherapeutic agent and a cyclodextrin, and/or a liposome compositions that contains a complex of an antifolate-based chemotherapeutic agent and a cyclodextrin and that also contains a complex of a platinum-based chemotherapeutic agent and a cyclodextrin, unless otherwise indicated.

In one embodiment, the disclosure provides a liposome composition comprising liposomes encapsulating a complex of doxorubicin (including stable salt and free base forms of doxorubicin, such as doxorubicin HCl) and (a) one or more polyglutamates or (b) a cyclodextrin. In some embodiments, the liposome is pegylated.

In some embodiment, the disclosure provides a liposome composition comprising liposomes encapsulating a complex of doxorubicin and one or more polyglutamates (e.g., as described herein).

In another embodiment, the disclosure provides a liposome composition comprising liposomes encapsulating a complex of doxorubicin and a cyclodextrin. The cyclodextrin complexed with doxorubicin in the provided liposome compositions can be derivatized or underivatized. In some embodiments, the cyclodextrin is derivatized. In further embodiments, the cyclodextrin is a derivatized beta-cyclodextrin (e.g., a hydroxypropyl beta-cyclodextrin (HP-beta-CD), and a sulfobutyl ether beta-CD (SBE)-beta-cyclodextrin). In some embodiments, the cyclodextrin is a derivatized beta-cyclodextrin comprising: 1, 2, 3, 4, 5, 6, 7, 8, 9, 10, or more 2-hydroxylpropyl-3- group substitutions of hydroxy groups; or 1, 2, 3, 4, 5, 6, 7, 8, 9, 10, or more sulfoalkyl ether group substitutions of hydroxy groups. In further embodiments, the cyclodextrin is a derivatized beta-cyclodextrin comprising: 1, 2, 3, 4, 5, 6, 7, 8, 9, 10, or more sulfobutyl ether group substitutions of hydroxy groups.

In some embodiments, the cyclodextrin complexed with doxorubicin is a derivatized cyclodextrin of Formula I:

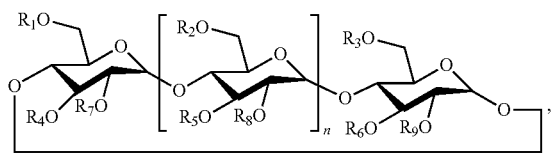

wherein: n is 4, 5, or 6; and wherein $R_1$, $R_2$, $R_3$, $R_4$, $R_5$, $R_6$, $R_7$, $R_8$, and $R_9$ are each, independently, —H, a straight chain or branched $C_1$-$C_8$-alkylene group, a 2-hydroxylpropyl-3- group; or an optionally substituted straight-chain or branched $C_1$-$C_6$ group, wherein at least one of $R_1$, $R_2$, $R_3$, $R_4$, $R_5$, $R_6$, $R_7$, $R_8$ and $R_9$ is a straight-chain or branched $C_1$-$C_8$-alkylene group or a 2-hydroxylpropyl-3- group.

In some embodiments, the cyclodextrin complexed with doxorubicin is a derivatized cyclodextrin of Formula II:

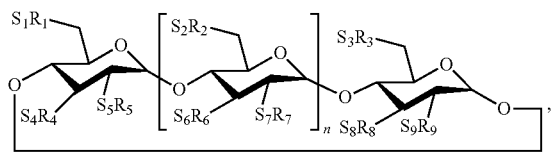

wherein: n is 4, 5, or 6; and wherein $R_1$, $R_2$, $R_3$, $R_4$, $R_5$, $R_6$, $R_7$, $R_8$, and $R_9$ are each, independently, —O— or a —O—($C_2$-$C_6$ alkylene)-$SO_3^-$ group; wherein at least one of $R_1$ and $R_2$ is independently a —O—($C_2$-$C_6$ alkylene)-$SO_3^-$ group; and $S_1$, $S_2$, $S_3$, $S_4$, $S_5$, $S_6$, $S_7$, $S_8$, and $S_9$ are each, independently, a —H or a H or a pharmaceutically acceptable cation. In further embodiments, the wherein the pharmaceutically acceptable cation is selected from: an alkali metal such as $Li^+$, $Na^+$, or $K^+$; an alkaline earth metal such as $Ca^{+2}$, or $Mg^{+2}$, and ammonium ions and amine cations such as the cations of (C1-C6)-alkylamines, piperidine, pyrazine, (C1-C6)-alkanolamine and (C4-C8)-cycloalkanolamine.

In some embodiments, the liposomes in the liposome composition comprise between 100 to 100,000 doxorubicin/cyclodextrin complexes. In additional embodiments, the liposome composition comprises liposomes that have a diameter in the range of 20 nm to 200 nm. In some embodiments, liposomes in the composition comprise between 100 to 100,000 doxorubicin molecules. In some embodiments, liposomes in the composition are anionic or neutral. In further embodiments, liposomes in the composition have a zeta potential that is less than or equal to zero. In further embodiments, liposomes in the composition has a zeta potential that is between 0 to −150 mV. In other embodiments, liposomes in the composition are cationic. In further embodiments, liposomes in the composition have a zeta potential that is between 1 and 100 mV.

The liposomes in the provided doxorubicin-based liposome compositions are preferably pegylated. In some embodiments, the polyethylene glycol of the liposomes has a number average molecular weight (Mn) of 200 to 5000 daltons. The internal phase of the liposome has a pH in the range of 2.8-6.8. In some embodiments, the internal phase of the liposome comprises trehalose (e.g., 5% to 20% weight of trehalose).

In additional embodiments, the doxorubicin-based liposome composition comprises liposomes that contain a targeting moiety. In some embodiments, the targeting moiety is attached to one or both of a PEG and the exterior of the liposome. In additional embodiments, the targeting moiety has a specific affinity for a surface antigen on a target cell of interest. In some embodiments, the targeting moiety is a polypeptide. In additional embodiments, the targeting moiety is an antibody, a humanized antibody, an antigen binding fragment of an antibody, a single chain antibody, a single-domain antibody, a bi-specific antibody, a synthetic antibody, a pegylated antibody, or a multimeric antibody. In some embodiments, the liposome composition comprises liposomes that contain from 30 to 500 targeting moieties. In further embodiments, the liposome composition comprises liposomes that contain from 30 to 200 targeting moieties.

In some embodiments, the doxorubicin-based liposome composition comprises liposomes that further contain one or more of an immunostimulatory agent, a detectable marker and a maleimide disposed on at least one of the PEG and the exterior of the liposome.

In some embodiments, the disclosed doxorubicin-based liposome compositions further comprise a second complex formed by a therapeutic agent or a salt thereof, and a cyclodextrin. In some embodiments, the therapeutic agent of the second complex is a member selected from the group: gemcitabine, and an antifolate (including salts and free forms thereof). The cyclodextrin of the second complex in the doxorubicin-based liposome compositions can be derivatized or underivatized. In some embodiments, the cyclodextrin is derivatized. In further embodiments, the cyclodextrin is a derivatized beta-cyclodextrin (e.g., a hydroxypropyl beta-cyclodextrin (HP-beta-CD), and a sulfobutyl ether beta-CD (SBE)-beta-cyclodextrin). In some embodiments, the cyclodextrin of the second complex in the doxorubicin-based liposome composition is a derivatized beta-cyclodextrin comprising: 1, 2, 3, 4, 5, 6, 7, 8, 9, 10, or more 2-hydroxylpropyl-3- group substitutions of hydroxy groups; or 1, 2, 3, 4, 5, 6, 7, 8, 9, 10, or more sulfoalkyl ether group substitutions of hydroxy groups. In further embodiments, the cyclodextrin of the second complex is a derivatized beta-cyclodextrin comprising: 1, 2, 3, 4, 5, 6, 7, 8, 9, 10, or more sulfobutyl ether group substitutions of hydroxy groups.

In some embodiments, the cyclodextrin of the second complex contained in the liposomes of the doxorubicin-based liposome composition (i.e., the complex formed by a therapeutic agent (including a salt and free form thereof), and a cyclodextrin) is a derivatized cyclodextrin of Formula I:

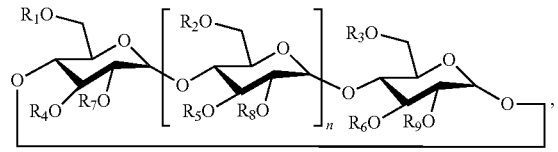

wherein: n is 4, 5, or 6; and wherein $R_1$, $R_2$, $R_3$, $R_4$, $R_5$, $R_6$, $R_7$, $R_8$, and $R_9$ are each, independently, —H, a straight chain or branched $C_1$-$C_8$-alkylene group, a 2-hydroxylpropyl-3- group; or an optionally substituted straight-chain or branched $C_1$-$C_6$ group, wherein at least one of $R_1$, $R_2$, $R_3$, $R_4$, $R_5$, $R_6$, $R_7$, $R_8$ and $R_9$ is a straight-chain or branched $C_1$-$C_8$-alkylene group or a 2-hydroxylpropyl-3- group.

In some embodiments, the cyclodextrin of the second complex contained in the liposomes of the doxorubicin-based liposome composition is a derivatized cyclodextrin of Formula II:

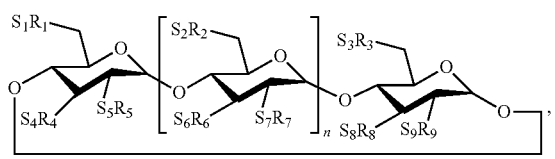

wherein; n is 4, 5, or 6; and wherein $R_1$, $R_2$, $R_3$, $R_4$, $R_5$, $R_6$, $R_7$, $R_8$, and $R_9$ are each, independently, —O— or a —O—($C_2$-$C_6$ alkylene)-$SO_3^-$ group; wherein at least one of $R_1$ and $R_2$ is independently a —O—($C_2$-$C_6$ alkylene)-$SO_3^-$ group; and $S_1$, $S_2$, $S_3$, $S_4$, $S_5$, $S_6$, $S_7$, $S_8$, and $S_9$ are each, independently, a —H or a H or a pharmaceutically acceptable cation. In further embodiments, the wherein the pharmaceutically acceptable cation is selected from: an alkali metal such as $Li^+$, $Na^+$, or $K^+$; an alkaline earth metal such as $Ca^{+2}$, or $Mg^{+2}$, and ammonium ions and amine cations such as the cations of (C1-C6)-alkylamines, piperidine, pyrazine, (C1-C6)-alkanolamine and (C4-C8)-cycloalkanolamine.

In some embodiments, the liposomes in the doxorubicin-based liposome composition comprise between 100 to 100,000 of the second complex formed by the therapeutic agent, and the cyclodextrin. In additional embodiments, the liposome composition comprises liposomes that have a diameter in the range of 20 nm to 200 nm. In some embodiments, liposomes in the composition comprise between 100 to 100,000 doxorubicin/cyclodextrin complexes. In some embodiments, the cyclodextrin of the second complex is different from the cyclodextrin of the doxorubicin/cyclodextrin complex. In some embodiments, the liposome comprises the same cyclodextrin in the second complex and doxorubicin complex. In some embodiments, the liposome comprises a cyclodextrin in the second complex that is different from the cyclodextrin of the doxorubicin complex.

According to some embodiments, the liposomes of the doxorubicin-based liposome compositions comprise oxidized phospholipids. In further embodiments, the phospholipids that are oxidized are a member selected from the group consisting of phosphatidylserines, phosphatidylinositols, phosphatidylethanolamines, phosphatidylcholines and 1-palmytoyl-2-arachidonoyl-sn-gly cero-2-phosphate.

In additional embodiments, the doxorubicin-based liposome compositions comprise oxidized 1-palmitoyl-2-arachidonoyl-sn-glycero-3-phosphorylchloine (OxPAPC). In further embodiments, the oxPAPCs are epoxyisoprostane-containing phospholipids. In further embodiments, the oxPAPC is 1-palmitoyl-2-(5,6-epoxyisoprostane E2)-sn-glycero-3-phosphocholine (5,6-PEIPC), 1-palmitoyl-2-(epoxy-cyclo-pentenone)-sn-glycero-3-phosphorylcholine (PECPC) and/or 1-palmitoyl-2-(epoxy-isoprostane E2)-sn-glycero-4-phosphocholine (PEIPC).

According to some embodiments, the provided doxorubicin-based liposome compositions further comprise one or more of an immunostimulatory agent, a detectable marker and a maleimide, wherein the immunostimulatory agent, the detectable marker or the maleimide is attached to the PEG or the exterior of the liposome. In some embodiments, the immunostimulating agent is at least one is a member selected from the group: a protein immunostimulating agent; a nucleic acid immunostimulating agent; a chemical immunostimulating agent; a hapten; and an adjuvant. In some embodiments, the immunostimulating agent is at least one selected from the group: a fluorescein; a fluorescein isothiocyanate (FITC); a DNP; a beta glucan; a beta-1,3-glucan; and a beta-1,6-glucan. In some embodiments, the immunostimulatory agent and the detectable marker is the same. In some embodiments, the liposome composition comprises a hapten. In further embodiments, the hapten comprises one or more of fluorescein or Beta 1,6-glucan.

In some embodiments, the liposomes of the disclosed doxorubicin-based liposome compositions further comprises at least one cryoprotectant selected from the group consisting of mannitol; trehalose; sorbitol; and sucrose. In additional embodiments, the provided liposomal composition is in unit dosage form. In some embodiments, pharmaceutical compositions comprising the liposome compositions disclosed herein are provided.

In some embodiments, the disclosure is directed to the use of the disclosed doxorubicin-based liposome compositions in the treatment of disease. In some embodiments, the disclosure is directed to use of the liposome compositions in the manufacture of a medicament for the treatment of disease.

In some embodiments, the disclosure provides a method of killing a hyperproliferative cell comprising contacting a hyperproliferative cell with a disclosed doxorubicin-based liposome composition. In further embodiments, the hyperproliferative cell is a cancer cell.

In some embodiments, the disclosure provides a method for treating or preventing disease in a subject needing such treatment or prevention, the method comprising administering an effective amount of a doxorubicin-based liposome composition provided herein to a subject in need thereof. In some embodiments, the administration is parenteral. In some embodiments, the administration is intravenous. In some embodiments, the administration is subcutaneous In additional embodiments, the disclosure provides a method for treating cancer in a subject, comprising administering an effective amount of a doxorubicin-based liposome composition disclosed herein to a subject having or at risk of having cancer. In further embodiments, the cancer is a member selected from the group: lung cancer, pancreatic cancer, breast cancer, ovarian cancer, prostate cancer, head and neck cancer, gastric cancer, gastrointestinal cancer, colorectal cancer, esophageal cancer, cervical cancer, liver cancer, kidney cancer, biliary duct cancer, gallbladder cancer, bladder cancer, sarcoma (e.g., osteosarcoma), brain cancer, central nervous system cancer, and melanoma; and a hematologic malignancy such as for example, a leukemia, a lymphoma and other B cell malignancies, myeloma and other plasma cell dyscrasias. In some embodiments, the administration is parenteral. In some embodiments, the administration is intravenous. In some embodiments, the administration is subcutaneous.

In other embodiments, the disclosure provides a method for treating cancer in a subject, comprising administering an effective amount of a doxorubicin-based liposome composition to a tumor expressing an antigen on its surface, the method comprising: administering a doxorubicin-based liposome composition disclosed herein to a subject having a tumor expressing the antigen in an amount to deliver a therapeutically effective dose of the liposome composition to the tumor. In some embodiments, the administration is parenteral. In some embodiments, the administration is intravenous. In some embodiments, the administration is subcutaneous.

A method for treating cancer that comprises administering an effective amount of a doxorubicin-based liposome composition disclosed herein to a subject, wherein the liposome comprises a targeting moiety with specific affinity for an antigen expressed on the surface of a cancer cell, and wherein the subject has or is at risk of having a cancer cell that expresses the antigen. In further embodiments, the antigen is a folate receptor. In some embodiments, the administration is parenteral. In some embodiments, the administration is intravenous. In some embodiments, the administration is subcutaneous Also provided is maintenance therapy that comprises administering an effective amount of a doxorubicin-based liposome composition disclosed herein to a subject that is undergoing or has undergone cancer therapy. In some embodiments, the administration is parenteral. In some embodiments, the administration is intravenous. In some embodiments, the administration is subcutaneous.

In one aspect, the disclosure provides compositions comprising a complex containing an antifolate and (a) cyclodextrin or (b) a cationic therapeutic agent. In some embodiments, the cationic therapeutic agent is a platinum-based drug.

Antifolates

Antifolates are a class of antiproliferative drugs that were designed to mimic folic acid in its systemic transport, physiologic cell uptake and intracellular processing. Monoglutamates are the only circulating forms of folates in the blood and the only form of folate that is transported across the cell membrane. Like monoglutamated folates, antifolates such as MTX, PMX, LTX, AG2034, RTX, piritrexim, pralatrexate, AG2034, GW1843, aminopterin, and LY309887 are monoglutamated and are transported into cells by reduced folate carriers (RFCs) and membrane folate-binding proteins, where they are polyglutamated, by the addition of ~2-5 L-gamma glutamyl moieties. The L-gamma-polyglutamated forms of the antifolate are biologically active and inhibit enzymes involved in folate metabolism. This inhibition of folate metabolism suppresses de novo nucleotide biosynthesis, renders the cell incapable of undergoing accurate DNA replication, and ultimately results in cell death.

In particular embodiments, the therapeutic agent is an antifolate or an antifolate-based chemotherapeutic agent.

As used herein, the term "antifolate" or "antifolate-based chemotherapeutic agent" refers to a polyglutamated or non-polyglutamated polyglutamatable antifolate. In some embodiments, the polyglutamatable antifolate is a member selected from methotrexate (MTX), PMX, lometrexol (LTX), AG2034, raltitrexed (RTX), piritrexim, pralatrexate, AG2034, GW1843, aminopterin, and LY309887. In some embodiments, the antifolate is polyglutamated and is a member selected from the group: polyglutamated methotrexate (MTX), polyglutamated pemetrexed (PMX), polyglutamated lometrexol (LTX), polyglutamated AG2034, polyglutamated raltitrexed (RTX), polyglutamated piritrexim, polyglutamated pralatrexate, polyglutamated AG2034, polyglutamated GW 1843, polyglutamated aminopterin, and polyglutamated LY309887.

Many antifolates contain one glutamyl group in their administered form. For example, pemetrexed (N-[4-2-(2-Amino-4,7-dihydro-4-oxo-1H-pyrrolo[2,3-d]pyrimidin-5-yl)ethyl]benzoyl]-1-glutamic acid) contains one glutamyl group (monoglutamated). The addition of glutamic acid residue(s) to pemetrexed results in polyglutamated pemetrexed. For example, the addition of 5 more glutamic acid residues to pemetrexed would lead to a total of 6 glutamyl groups (one from pemetrexed and 5 additional glutamyl groups added) and is referred to in this document as hexaglutamated pemetrexed or pemetrexed hexaglutamate. In the literature this may also be referred to as pentaglutamated pemetrexed or pemetrexed pentaglutamated.

As used herein, the term "antifolate-based liposome composition" refers a liposome composition that contains a complex of an antifolate-based therapeutic agent and a cyclodextrin, and/or a liposome compositions that contains a complex of an antifolate-based chemotherapeutic agent and a cyclodextrin and that also contains a complex of a platinum-based chemotherapeutic agent and a cyclodextrin. These liposome compositions provide improvements to the efficacy and safety of delivering antifolate -based agents to cancer cells by providing the preferential delivery of a more cytotoxic payload (e.g., polyglutamated antifolates) compared to the cytotoxicity of the corresponding antifolatae-based agent delivered in its uncomplexed and non-liposome encapsulated state.

In one aspect, the disclosure provides compositions comprising a complex containing an antifolate and (a) cyclodextrin or (b) a cationic therapeutic agent. In some embodiments, the cationic therapeutic agent is a platinum-based drug. In some embodiments, the antifolate-platinum-based drug complex comprises cisplatin or a salt thereof. In some embodiments, the platinum-based drug complex comprises oxaliplatin, or a salt thereof.

In one embodiment, the disclosure provides a liposome composition comprising a complex of an antifolate-based therapeutic agent and a cyclodextrin; one or more pharmaceutically acceptable carriers; and a pegylated liposome. In some embodiments, the antifolate-based therapeutic agent is a member selected from MTX, PMX, LTX, AG2034, RTX, piritrexim, pralatrexate, AG2034, GW1843, aminopterin, and LY309887. In some embodiments, the antifolate-based therapeutic agent is polyglutamated and is a member selected from the group: polyglutamated methotrexate (MTX), polyglutamated pemetrexed (PMX), polyglutamated lometrexol (LTX), polyglutamated AG2034, polyglutamated raltitrexed (RTX), polyglutamated piritrexim, polyglutamated pralatrexate, polyglutamated AG2034, polyglutamated GW1843, polyglutamated aminopterin, and polyglutamated LY309887.

In some embodiments, the antifolate-based therapeutic agent is pemetrexed. In further embodiments, the antifolate-based therapeutic agent is polyglutamated pemetrexed. In further embodiments, the antifolate-based therapeutic agent is polyglutamated pemetrexed containing a total of 2, 3, 4, 5, 6, 7, 8, 9, 10, 2-6 or 2-10 glutamyl groups. In some embodiments, the polyglutamated pemetrexed contains a total of 2, 3, 4, 5, 6, 7, 8, 9, 10, 2-6 or 2-10 L-gamma peptide linkages. In other embodiments, the polyglutamated pemetrexed contains a total of 2, 3, 4, 5, 6, 7, 8, 9, 10, 2-6 or 2-10 D-gamma peptide linkages. In additional embodiments, the polyglutamated pemetrexed contains a total of 2, 3, 4, 5, 6, 7, 8, 9, 10, 2-6 or 2-10 alpha peptide linkages.

In some embodiments, the antifolate-based therapeutic agent is methotrexate. In further embodiments, the antifolate-based therapeutic agent is polyglutamated methotrexate In further embodiments, the antifolate-based therapeutic agent is polyglutamated methotrexate containing a total of 2, 3, 4, 5, 6, 7, 8, 9, 10, 2-6 or 2-10 glutamyl groups. In some embodiments, the polyglutamated methotrexate contains a total of 2, 3, 4, 5, 6, 7, 8, 9, 10, 2-6 or 2-10 L-gamma peptide linkages. In other embodiments, the polyglutamated methotrexate contains a total of 2, 3, 4, 5, 6, 7, 8, 9, 10, 2-6 or 2-10 D-gamma peptide linkages. In additional embodiments, the polyglutamated methotrexate contains a total of 2, 3, 4, 5, 6, 7, 8, 9, 10, 2-6 or 2-10 alpha peptide linkages.

In some embodiments, the antifolate-based therapeutic agent is lometrexol. In further embodiments, the antifolate-based therapeutic agent is polyglutamated lometrexol. In some embodiments, the antifolate-based therapeutic agent is polyglutamated lometrexol containing a total of 2, 3, 4, 5, 6, 7, 8, 9, 10, 2-6 or 2-10 glutamyl groups. In some embodiments, the polyglutamated lometrexol contains a total of 2, 3, 4, 5, 6, 7, 8, 9, 10, 2-6 or 2-10 L-gamma peptide linkages. In other embodiments, the polyglutamated lometrexol contains a total of 2, 3, 4, 5, 6, 7, 8, 9, 10, 2-6 or 2-10 D-gamma peptide linkages. In additional embodiments, the polyglutamated lometrexol contains a total of 2, 3, 4, 5, 6, 7, 8, 9, 10, 2-6 or 2-10 alpha peptide linkages.

In some embodiments, the antifolate-based therapeutic agent is pralatrexate. In some embodiments, the antifolate-based therapeutic agent is polyglutamated pralatrexate. In some embodiments, the antifolate-based therapeutic agent is polyglutamated pralatrexate containing a total of 2, 3, 4, 5, 6, 7, 8, 9, 10, 2-6 or 2-10 glutamyl groups. In some embodiments, the polyglutamated pralatrexate contains a total of 2, 3, 4, 5, 6, 7, 8, 9, 10, 2-6 or 2-10 L-gamma peptide linkages. In other embodiments, the polyglutamated pralatrexate contains a total of 2, 3, 4, 5, 6, 7, 8, 9, 10, 2-6 or 2-10 D-gamma peptide linkages. In additional embodiments, the polyglutamated pralatrexate contains a total of 2, 3, 4, 5, 6, 7, 8, 9, 10, 2-6 or 2-10 alpha peptide linkages.

In some embodiments, the antifolate-based therapeutic agent is a polyglutamated antifolate selected from the group: polyglutamated AG2034, polyglutamated raltitrexed (RTX), polyglutamated piritrexim, polyglutamated AG2034, polyglutamated GW1843, polyglutamated aminopterin, and polyglutamated LY309887. In some embodiments, the polyglutamated antifolate contains a total of 2, 3, 4, 5, 6, 7, 8, 9, 10, 2-6 or 2-10 glutamyl groups. In some embodiments, the polyglutamated antifolate contains a total of 2, 3, 4, 5, 6, 7, 8, 9, 10, 2-6 or 2-10 L-gamma peptide linkages. In other embodiments, the polyglutamated antifolate contains a total of 2, 3, 4, 5, 6, 7, 8, 9, 10, 2-6 or 2-10 D-gamma peptide linkages. In additional embodiments, polyglutamated antifolate contains a total of 2, 3, 4, 5, 6, 7, 8, 9, 10, 2-6 or 2-10 alpha peptide linkages.

In some embodiments, the antifolate contained in an antifolate-based liposome composition disclosed herein is an antifolate as depicted in FIG. 1. In some embodiments, that antifolate is an antifolate as depicted in FIG. 1. Additional gamma L polyglutamated antifolates that can be included within the anti-folate-based liposome compositions provided herein are disclosed in International Application No. PCT/US2017/046667, the contents of which is herein incorporated by reference in its entirety.

In some embodiments, the antifolate contained in an antifolate-based liposome composition disclosed herein is an antifolate as depicted in FIG. 2. Additional alpha- and gamma D polyglutamated antifolates that can be included within the anti-folate-based liposome compositions provided herein are disclosed in International Application No. PCT/US2017/046666, the contents of which is herein incorporated by reference in its entirety.

In a distinct aspect, the disclosure provides liposome compositions that contain liposomes encapsulating a complex of a anti-folate and a cyclodextrin such as a derivatized beta cyclodextrin. In some embodiments, antifolate is polyglutamated (e.g., a polyglutamated antifolate having the structure Antifolate-(α-L-glutamyl)n, where n=2, 3, 4, 5, 6, 7, 8, 9, 10, 2-6 or 2-10). In some embodiments, the polyglutamate is selected from the group: MTX, PMX, LTX, AG2034, RTX, piritrexim, pralatrexate, AG2034, GW 1843, aminopterin, and LY309887.

Accordingly, in one embodiment, the disclosure provides a liposome composition comprising liposomes encapsulating a complex of an antifolate and a cyclodextrin. In some embodiments, the liposomes are pegylated. In some embodiments, the antifolate is polyglutamated (e.g., a polyglutamate having the structure Antifolate-(α-L-glutamyl)n, where n=2, 3, 4, 5, 6, 7, 8, 9, 10, 2-6 or 2-10). In some embodiments, the polyglutamate is selected from the group: MTX, PMX, LTX, AG2034, RTX, piritrexim, pralatrexate, AG2034, GW1843, aminopterin, and LY309887.

In some embodiments, the cyclodextrin complexed with the antifolate-based therapeutic agent in the provided liposome compositions is derivatized or underivatized. In some embodiments, the cyclodextrin is derivatized. In further embodiments, the cyclodextrin is a derivatized beta-cyclodextrin (e.g., a hydroxypropyl beta-cyclodextrin (HP-beta-CD), and a sulfobutyl ether beta-CD (SBE)-beta-cyclodextrin). In some embodiments, the cyclodextrin is a derivatized beta-cyclodextrin comprising: 1, 2, 3, 4, 5, 6, 7, 8, 9, 10, or more 2-hydroxylpropyl-3- group substitutions of hydroxy groups; or 1, 2, 3, 4, 5, 6, 7, 8, 9, 10, or more sulfoalkyl ether group substitutions of hydroxy groups. In further embodiments, the cyclodextrin is a derivatized beta-cyclodextrin comprising: 1, 2, 3, 4, 5, 6, 7, 8, 9, 10, or more sulfobutyl ether group substitutions of hydroxy groups.

In some embodiments, the cyclodextrin complexed with the antifolate-based therapeutic agent is a derivatized cyclodextrin of Formula I:

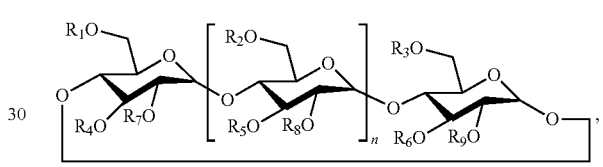

wherein: n is 4, 5, or 6; and wherein $R_1$, $R_2$, $R_3$, $R_4$, $R_5$, $R_6$, $R_7$, $R_8$, and $R_9$ are each, independently, —H, a straight chain or branched $C_1$-$C_8$-alkylene group, a 2-hydroxylpropyl-3- group; or an optionally substituted straight-chain or branched $C_1$-$C_6$ group, wherein at least one of $R_1$, $R_2$, $R_3$, $R_4$, $R_5$, $R_6$, $R_7$, $R_8$ and $R_9$ is a straight-chain or branched $C_1$-$C_8$-alkylene group or a 2-hydroxylpropyl-3- group.

In some embodiments, the cyclodextrin complexed with the antifolate-based therapeutic agent is a derivatized cyclodextrin of Formula II:

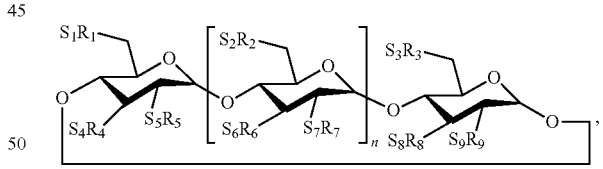

wherein: n is 4, 5, or 6; and wherein $R_1$, $R_2$, $R_3$, $R_4$, $R_5$, $R_6$, $R_7$, $R_8$, and $R_9$ are each, independently, —O— or a —O—($C_2$-$C_6$ alkylene)-$SO_3^-$ group; wherein at least one of $R_1$ and $R_2$ is independently a —O—($C_2$-$C_6$ alkylene)-$SO_3^-$ group; and $S_1$, $S_2$, $S_3$, $S_4$, $S_5$, $S_6$, $S_7$, $S_8$, and $S_9$ are each, independently, a —H or a H or a pharmaceutically acceptable cation. In further embodiments, the wherein the pharmaceutically acceptable cation is selected from: an alkali metal such as $Li^+$, $Na^+$, or $K^+$; an alkaline earth metal such as $Ca^{+2}$, or $Mg^{+2}$, and ammonium ions and amine cations such as the cations of (C1-C6)-alkylamines, piperidine, pyrazine, (C1-C6)-alkanolamine and (C4-C8)-cycloalkanolamine.

In some embodiments, the liposomes in the liposome composition comprise between 100 to 100,000 antifolate-based therapeutic agent/cyclodextrin complexes. In additional embodiments, the liposome composition comprises liposomes that have a diameter in the range of 20 nm to 200 nm. In some embodiments, liposomes in the composition comprise between 100 to 100,000 platinum. In some embodiments, liposomes in the composition are anionic or neutral. In further embodiments, liposomes in the composition have a zeta potential that is less than or equal to zero. In further embodiments, liposomes in the composition has a zeta potential that is between 0 to −150 mV. In other embodiments, liposomes in the composition are cationic. In further embodiments, liposomes in the composition have a zeta potential that is between 1 and 100 mV.

The liposomes in the provided antifolate-based liposome compositions are preferably pegylated. In some embodiments, the polyethylene glycol of the liposomes has a number average molecular weight (Mn) of 200 to 5000 daltons. The internal phase of the liposome has a pH in the range of 2.8-6.8. In some embodiments, the internal phase of the liposome comprises trehalose (e.g., 5% to 20% weight of trehalose).

In additional embodiments, the antifolate-based liposome composition comprises liposomes that contain a targeting moiety. In some embodiments, the targeting moiety is attached to one or both of a PEG and the exterior of the liposome. In additional embodiments, the targeting moiety has a specific affinity for a surface antigen on a target cell of interest. In some embodiments, the targeting moiety is a polypeptide. In additional embodiments, the targeting moiety is an antibody, a humanized antibody, an antigen binding fragment of an antibody, a single chain antibody, a single-domain antibody, a bi-specific antibody, a synthetic antibody, a pegylated antibody, or a multimeric antibody. In some embodiments, the liposome composition comprises liposomes that contain from 30 to 500 targeting moieties. In further embodiments, the liposome composition comprises liposomes that contain from 30 to 200 targeting moieties.

In some embodiments, the antifolate-based liposome composition comprises liposomes that further contain one or more of an immunostimulatory agent, a detectable marker and a maleimide disposed on at least one of the PEG and the exterior of the liposome.

In some embodiments, the disclosed antifolate-based liposome compositions further comprise a second complex formed by a therapeutic agent or a salt thereof, and a cyclodextrin. In some embodiments, the therapeutic agent of the second complex is a member selected from the group: gemcitabine, and doxorubicin (including salts and free forms thereof). The cyclodextrin of the second complex in the gemcitabine-based liposome compositions can be derivatized or underivatized. In some embodiments, the cyclodextrin is derivatized. In further embodiments, the cyclodextrin is a derivatized beta-cyclodextrin (e.g., a hydroxypropyl beta-cyclodextrin (HP-beta-CD), and a sulfobutyl ether beta-CD (SBE)-beta-cyclodextrin). In some embodiments, the cyclodextrin of the second complex in the gemcitabine-based liposome composition is a derivatized beta-cyclodextrin comprising: 1, 2, 3, 4, 5, 6, 7, 8, 9, 10, or more 2-hydroxylpropyl-3- group substitutions of hydroxy groups; or 1, 2, 3, 4, 5, 6, 7, 8, 9, 10, or more sulfoalkyl ether group substitutions of hydroxy groups. In further embodiments, the cyclodextrin of the second complex is a derivatized beta-cyclodextrin comprising: 1, 2, 3, 4, 5, 6, 7, 8, 9, 10, or more sulfobutyl ether group substitutions of hydroxy groups.

In some embodiments, the cyclodextrin of the second complex contained in the liposomes of the antifolate -based liposome composition (i.e., the complex formed by a thera-peutic agent (including a salt and free form thereof), and a cyclodextrin) is a derivatized cyclodextrin of Formula I:

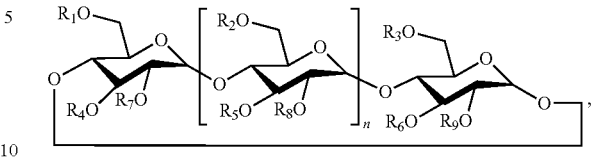

wherein: n is 4, 5, or 6; and wherein $R_1$, $R_2$, $R_3$, $R_4$, $R_5$, $R_6$, $R_7$, $R_8$, and $R_9$ are each, independently, —H, a straight chain or branched $C_1$-$C_8$-alkylene group, a 2-hydroxylpropyl-3- group; or an optionally substituted straight-chain or branched $C_1$-$C_6$ group, wherein at least one of $R_1$, $R_2$, $R_3$, $R_4$, $R_5$, $R_6$, $R_7$, $R_8$ and $R_9$ is a straight-chain or branched $C_1$-$C_8$-alkylene group or a 2-hydroxylpropyl-3- group In some embodiments, the cyclodextrin of the second complex contained in the liposomes of the antifolate-based liposome composition is a derivatized cyclodextrin of Formula II:

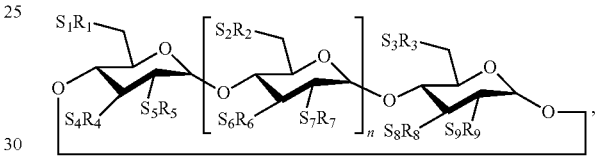

wherein: n is 4, 5, or 6; and wherein $R_1$, $R_2$, $R_3$, $R_4$, $R_5$, $R_6$, $R_7$, $R_8$, and $R_9$ are each, independently, —O— or a —O— ($C_2$-$C_6$ alkylene)-$SO_3^-$ group; wherein at least one of $R_1$ and $R_2$ is independently a —O—($C_2$-$C_6$ alkylene)-$SO_3^-$ group; and $S_1$, $S_2$, $S_3$, $S_4$, $S_5$, $S_6$, $S_7$, $S_8$, and $S_9$ are each, independently, a —H or a H or a pharmaceutically acceptable cation. In further embodiments, the wherein the pharmaceutically acceptable cation is selected from: an alkali metal such as $Li^+$, $Na^+$, or $K^+$; an alkaline earth metal such as $Ca^{+2}$, or $Mg^{+2}$, and ammonium ions and amine cations such as the cations of ($C_1$-$C_6$)-alkylamines, piperidine, pyrazine, ($C_1$-$C_6$)-alkanolamine and ($C_4$-$C_8$)-cycloalkanolamine.

In some embodiments, the liposomes in the antifolate-based liposome composition comprise between 100 to 100,000 of the second complex formed by the therapeutic agent, and the cyclodextrin. In additional embodiments, the liposome composition comprises liposomes that have a diameter in the range of 20 nm to 200 nm. In some embodiments, liposomes in the composition comprise between 100 to 100,000 antifolate-based agent/cyclodextrin complexes. In some embodiments, the cyclodextrin of the second complex is different from the cyclodextrin of the antifolate -based agent complex. In some embodiments, the liposome comprises the same cyclodextrin in the second complex and the antifolate agent-based complex. In some embodiments, the liposome comprises a cyclodextrin in the second complex that is different from the cyclodextrin of the antifolate-based agent complex.

According to some embodiments, the liposomes of the antifolate-based liposome compositions comprise oxidized phospholipids. In further embodiments, the phospholipids that are oxidized are a member selected from the group consisting of phosphatidylserines, phosphatidylinositols, phosphatidylethanolamines, phosphatidylcholines and 1-palmytoyl-2-arachidonoyl-sn-gly cero-2-phosphate.

In additional embodiments, the antifolate-based liposome compositions comprise oxidized 1-palmitoyl-2-arachidonoyl-sn-glycero-3-phosphorylchloine (OxPAPC). In further embodiments, the oxPAPCs are epoxyisoprostane-containing phospholipids. In further embodiments, the oxPAPC is 1-palmitoyl-2-(5,6-epoxyisoprostane E2)-sn-glycero-3-phosphocholine (5,6-PEIPC), 1-palmitoyl-2-(epoxy-cyclopentenone)-sn-glycero-3-phosphorylchloine (PECPC) and/or 1-palmitoyl-2-(epoxy-isoprostane E2)-sn-glycero-4-phosphocholine (PEIPC).

According to some embodiments, the provided antifolate-based liposome compositions further comprise one or more of an immunostimulatory agent, a detectable marker and a maleimide, wherein the immunostimulatory agent, the detectable marker or the maleimide is attached to the PEG or the exterior of the liposome. In some embodiments, the immunostimulating agent is at least one is a member selected from the group: a protein immunostimulating agent; a nucleic acid immunostimulating agent; a chemical immunostimulating agent; a hapten; and an adjuvant. In some embodiments, the immunostimulating agent is at least one selected from the group: a fluorescein; a fluorescein isothiocyanate (FITC); a DNP; a beta glucan; a beta-1,3-glucan; and a beta-1,6-glucan. In some embodiments, the immunostimulatory agent and the detectable marker is the same. In some embodiments, the liposome composition comprises a hapten. In further embodiments, the hapten comprises one or more of fluorescein or Beta 1,6-glucan.

In some embodiments, the liposomes of the disclosed antifolate-based liposome compositions further comprises at least one cryoprotectant selected from the group consisting of mannitol; trehalose; sorbitol; and sucrose. In additional embodiments, the provided liposomal composition is in unit dosage form. In some embodiments, pharmaceutical compositions comprising the liposome compositions disclosed herein are provided.

In some embodiments, the disclosure is directed to the use of the disclosed antifolate-based liposome compositions in the treatment of disease. In some embodiments, the disclosure is directed to use of the liposome compositions in the manufacture of a medicament for the treatment of disease.

In some embodiments, the disclosure provides a method of killing a hyperproliferative cell comprising contacting a hyperproliferative cell with a disclosed antifolate-based liposome composition. In further embodiments, the hyperproliferative cell is a cancer cell.

In some embodiments, the disclosure provides a method for treating or preventing disease in a subject needing such treatment or prevention, the method comprising administering an effective amount of a antifolate-based liposome composition provided herein to a subject in need thereof. In some embodiments, the administration is parenteral. In some embodiments, the administration is intravenous. In some embodiments, the administration is subcutaneous In additional embodiments, the disclosure provides a method for treating cancer in a subject, comprising administering an effective amount of a antifolate-based liposome composition disclosed herein to a subject having or at risk of having cancer. In further embodiments, the cancer is a member selected from the group: lung cancer, pancreatic cancer, breast cancer, ovarian cancer, prostate cancer, head and neck cancer, gastric cancer, gastrointestinal cancer, colorectal cancer, esophageal cancer, cervical cancer, liver cancer, kidney cancer, biliary duct cancer, gallbladder cancer, bladder cancer, sarcoma (e.g., osteosarcoma), brain cancer, central nervous system cancer, and melanoma; and a hematologic malignancy such as for example, a leukemia, a lymphoma and other B cell malignancies, myeloma and other plasma cell dyscrasias. In some embodiments, the administration is parenteral. In some embodiments, the administration is intravenous. In some embodiments, the administration is subcutaneous In other embodiments, the disclosure provides a method for treating cancer in a subject, comprising administering an effective amount of a antifolate-based liposome composition to a subject, wherein the liposome comprises a targeting moiety with specific affinity for an antigen expressed on the surface of a cancer cell, and wherein the subject has or is at risk of having a cancer cell that expresses the antigen. In further embodiments, the antigen is a folate receptor. In some embodiments, the administration is parenteral. In some embodiments, the administration is intravenous. In some embodiments, the administration is subcutaneous.

A method for treating cancer that comprises administering an effective amount of an antifolate-based liposome composition provided herein to a subject, wherein the liposome comprises a targeting moiety with specific affinity for an antigen expressed on the surface of a cancer cell, and wherein the subject has or is at risk of having a cancer cell that expresses the antigen. In some embodiments, the administration is parenteral. In some embodiments, the administration is intravenous. In some embodiments, the administration is subcutaneous Also provided is maintenance therapy that comprises administering an effective amount of a liposome composition disclosed herein to a subject that is undergoing or has undergone cancer therapy. In some embodiments, the administration is parenteral. In some embodiments, the administration is intravenous. In some embodiments, the administration is subcutaneous.

Formulations.

In some embodiments, the liposome composition is provided as a pharmaceutical composition containing the liposome and a carrier, e.g., a pharmaceutically acceptable carrier. Examples of pharmaceutically acceptable carriers contained in the provided pharmaceutical compositions include normal saline, isotonic dextrose, isotonic sucrose, Ringer's solution, and Hanks' solution. In some embodiments, a buffer substance is added to maintain an optimal pH for storage stability of the pharmaceutical composition. In some embodiments, the pH of the pharmaceutical composition is between 6.0 and 7.5. In some embodiments, the pH is between 6.3 and 7.0. In further embodiments, the pH is 6.5. Ideally the pH of the pharmaceutical composition allows for both stability of liposome membrane lipids and retention of the entrapped entities. Histidine, hydroxyethylpiperazine-ethylsulfonate (HEPES), morpholipoethylsulfonate (MES), succinate, tartrate, and citrate, typically at 2-20 mM concentration, are exemplary buffer substances. Other suitable carriers include, e.g., water, buffered aqueous solution, 0.4% NaCl, and 0.3% glycine. Protein, carbohydrate, or polymeric stabilizers and tonicity adjusters can be added, e.g., gelatin, albumin, dextran, or polyvinylpyrrolidone. The tonicity of the composition can be adjusted to the physiological level of 0.25-0.35 mol/kg with glucose or a more inert compound such as lactose, sucrose, mannitol, or dextrin. These compositions can routinely be sterilized using conventional, sterilization techniques known in the art (e.g., by filtration). The resulting aqueous solutions can be packaged for use or filtered under aseptic conditions and lyophilized, the lyophilized preparation being combined with a sterile aqueous medium prior to administration.

The provided liposome compositions can also contain other pharmaceutically acceptable auxiliary substances as required to approximate physiological conditions, such as pH adjusting and buffering agents, and tonicity adjusting agents, for example, sodium acetate, sodium lactate, sodium chloride, potassium chloride, and calcium chloride. Additionally, the liposome suspension may include lipid-protective agents which protect lipids against free-radical and lipid-peroxidative damages on storage. Lipophilic free-radical quenchers, such as alpha-tocopherol and water-soluble iron-specific chelators, such as ferrioxamine, are suitable.

The liposome concentration in the provided fluid pharmaceutical formulations can vary widely depending upon need, e.g., from less than about 0.05% usually or at least about 2-10% to as much as 30 to 50% by weight and will be selected primarily by fluid volumes, and viscosities, in accordance with the particular mode of administration selected. For example, the concentration may be increased to lower the fluid load associated with treatment. This may be particularly desirable in patients having atherosclerosis-associated congestive heart failure or severe hypertension. Alternatively, liposome pharmaceutical compositions composed of irritating lipids may be diluted to low concentrations to lessen inflammation at the site of administration.

Some embodiments relate to a method of delivering a targeted pegylated liposome containing complexes of a platinum-based chemotherapeutic agent and one or more polyglutamate molecules. An exemplary method comprises the step of administering a liposome composition comprising a targeted pegylated liposome containing complexes of a platinum-based chemotherapeutic agent and one or more polyglutamate molecules (e.g., a composition as described herein) in an amount sufficient to deliver an effective dose of the platinum-based chemotherapeutic agent to the tumor.

Some embodiments relate to a method of delivering a targeted pegylated liposome containing complexes of a platinum-based chemotherapeutic agent and a cyclodextrin. An exemplary method comprises the step of administering a liposome composition comprising a targeted pegylated liposome containing complexes of a platinum-based chemotherapeutic agent and a cyclodextrin (e.g., a composition as described herein) in an amount sufficient to deliver an effective dose of the platinum-based chemotherapeutic agent to the tumor.

The amount of liposome composition administered will depend upon the particular cyclodextrin or polyglutamate complexed therapeutic agent encapsulated inside the liposomes, the disease state being treated, the type of liposomes being used, and the judgment of the clinician. Generally the amount of liposome pharmaceutical composition administered will be sufficient to deliver an effective dose of the particular therapeutic agent.

The quantity of liposome composition necessary to deliver an effective dose can be determined by routine in vitro and in vivo methods, common in the art of drug testing. See, for example, D. B. Budman, A. H. Calvert, E. K. Rowinsky (editors). Handbook of Anticancer Drug Development, L W W, 2003. Effective dosages for various therapeutic compositions are known to those skilled in the art. In some embodiments, a therapeutic entity delivered via the pharmaceutical liposome composition and provides at least the same or higher activity than the activity obtained by administering the same amount of the therapeutic entity in its routine non-liposome formulation. Typically the dosages for the liposome pharmaceutical composition is in a range for example, between about 0.005 and about 500 mg of the therapeutic entity per kilogram of body weight, most often, between about 0.1 and about 100 mg therapeutic entity/kg of body weight.

Pharmaceutical compositions comprising the provided liposome compositions are also provided. Pharmaceutical compositions are sterile compositions that comprise a sample liposome and preferably a platinum-based chemotherapeutic agent, cyclodextrin, polyglutamate, platinum-polyglutamate complex, and/or platinum-cyclodextrin complex, preferably in a pharmaceutically-acceptable carrier.

Unless otherwise stated herein, a variety of administration routes are available. The particular mode selected will depend, upon the particular active agent selected, the particular condition being treated and the dosage required for therapeutic efficacy. The provided methods can be practiced using any known mode of administration that is medically acceptable and in accordance with good medical practice. In some embodiments, the administration route is an injection. In further embodiments, the injection is by a parenteral route elected from an intramuscular, subcutaneous, intravenous, intraarterial, intrapentoneal, intraarticular, intraepidural, intrathecal, intravenous, intramuscular, or intra sternal injection. In some embodiments, the administration route is an infusion. In additional embodiments, the administration route is oral, nasal, mucosal, sublingual, intratracheal, ophthalmic, rectal, vaginal, ocular, topical, transdermal, pulmonary, or inhalation.

In some embodiment, the liposomes are prepared as an infusion composition, an injection composition, a parenteral composition, or a topical composition. In further embodiments, the injection includes one or more of: intraperitoneal injection, direct intratumor injection, intra-arterial injection, and intravenous injection, subcutaneous injection, intramuscular injection, delivery via transcutaneous and intranasal route. In a further embodiment, the liposome composition is a liquid solution or a suspension. However, solid forms suitable for solution in, or suspension in, liquid vehicles prior to injection are also provided herein. In some embodiments, the liposome composition is formulated as an enteric-coated tablet or gel capsule according to methods known in the art.

In some embodiments, the liposome compositions are administered to a tumor of the central nervous system using a slow, sustained intracranial infusion of the liposomes directly into the tumor (e.g., a convection-enhanced delivery (CED)). See, Saito et al., Cancer Research 64:2572-2579 (2004); Mamot et al., J. Neuro-Oncology 68:1-9 (2004). In other embodiments, the liposome compositions are directly applied to tissue surfaces. Sustained release, pH dependent release, and other specific chemical or environmental condition-mediated release administration of the components of the liposome (e.g., depot injections and erodible implants) are also provided. Examples of such release-mediating compositions are further provided herein or otherwise known in the art.

For administration by inhalation, the compositions can be conveniently delivered in the form of an aerosol spray presentation from pressurized packs or a nebulizer, with the use of a suitable propellant, e.g., dichlorodifluoromethane, trichlorofluoromethane, ichlorotetrafluoroethane, carbon dioxide or other suitable gas. In the case of a pressurized aerosol, the dosage unit can be determined by providing a valve to deliver a metered amount.

When it is desirable to deliver the compositions systemically, they can formulated for parenteral administration by injection, e.g., by bolus injection or continuous infusion. Formulations for injection can be presented in unit dosage form, e.g., in ampoules or in multi-dose containers. Pharmaceutical parenteral formulations include aqueous solutions of the ingredients. Aqueous injection suspensions can contain substances which increase the viscosity of the suspension, such as sodium carboxymethyl cellulose, sorbitol, or dextran. Alternatively, suspensions of liposomes can be prepared as oil-based suspensions. Suitable lipophilic solvents or vehicles include fatty oils such as sesame oil, or synthetic fatty acid esters, such as ethyl oleate or triglycerides.

Alternatively, the liposome compositions can be in powder form or lyophilized form for constitution with a suitable vehicle, e.g., sterile pyrogen-free water, before use.

The provided liposome compositions can also be formulated in rectal or vaginal compositions such as suppositories or retention enemas, e.g., containing conventional suppository bases such as cocoa butter or other glycerides.

The provided liposome compositions have applications, in vivo, ex vivo and in vitro. In some embodiments, the compositions have in vitro applications. In vitro use may include uses such as cell culturing and tissue engineering where selective treatment of a subpopulation of cells is desired. For example, during the culture of stem cells from a normal patient or a patient suffering from cancer, the cells can be treated with a sample composition or sample liposome as discussed to address cancerous subpopulations of cells. The cancerous subpopulation may arise because the donor originally has cancer or because the cells spontaneously transform during in vitro procedures.

In some embodiments, the liposome compositions are provided in a kit comprising a container with the liposomes, and optionally, a container with the entity (antigen) targeted or preferentially bound by liposomes, and an instruction, e.g., procedures or information related to using the liposome composition in one or more applications. Such instruction can be provided via any medium, e.g., hard paper copy, electronic medium, or access to a database or website containing the instruction.

The embodiments, provide pharmaceutical compositions. Pharmaceutical compositions are sterile compositions that comprise a delivery vehicle such as a liposome encapsulating a platinum-cyclodextrin complex or a platinum-polyglutamate complex, preferably in a pharmaceutically-acceptable carrier.

When it is desirable to deliver the compositions systemically, they may be formulated for parenteral administration by injection, e.g., by bolus injection or continuous infusion. Formulations for injection may be presented in unit dosage form, e.g., in ampoules or in multi-dose containers. Pharmaceutical parenteral formulations include aqueous solutions of the ingredients. Aqueous injection suspensions may contain substances that increase the viscosity of the suspension, such as sodium carboxymethyl cellulose, sorbitol, or dextran. Alternatively, suspensions of liposomes may be prepared as oil-based suspensions. Suitable lipophilic solvents or vehicles include fatty oils, such as sesame oil, or synthetic fatty acid esters, such as ethyl oleate or triglycerides.

Alternatively, the liposomal compositions may be in powder form or lyophilized form for constitution with a suitable vehicle, e.g., sterile pyrogen-free water, before use.

Administration

Generally, the compositions of the present invention can be administered to patients by various routes. The particular mode selected will depend, of course, upon the particular active agent selected, the particular condition being treated and the dosage required for therapeutic efficacy. The provided methods, generally speaking, may be practiced using any mode of administration that is medically acceptable, meaning any mode that produces effective levels of a desired response without causing clinically unacceptable adverse effects. Administration routes for the disclosed compositions include injections, by parenteral routes, such as subcutaneous, intravenous (including bolus injection), intramuscular, intraarterial, intraperitoneal, intraarticular, intraepidural, intrathecal, intravenous, intramuscular, intra sternal injection or infusion, or others, as well as oral, nasal, mucosal, sublingual, intratracheal, ophthalmic, rectal, vaginal, ocular, topical, transdermal, pulmonary, and inhalation administration routes.

In one embodiment, the provided pharmaceutical liposome composition is prepared as an infusion composition, an injection composition, a parenteral composition, or a topical composition, either as a liquid solution or suspension. However, solid forms suitable for solution in, or suspension in, liquid vehicles prior to injection can also be prepared. In an additional embodiment, the liposome composition is formulated into an enteric-coated tablet or gel capsule according to methods know in the art.

For delivery of liposomal drugs formulated according to example embodiments, to tumors of the central nervous system, a slow, sustained intracranial infusion of the liposomes directly into the tumor (a convection-enhanced delivery, or CED) may be of particular advantage. See, Saito, et al., Cancer Research, (64): 2572-2579 (2004); Mamot et al., J. Neuro-Oncology (68):1-9 (2004). The compositions may, for example, also be directly applied to tissue surfaces. Sustained release, pH dependent release, or other specific chemical or environmental condition mediated release administration is also specifically provided herein, e.g., by such means as depot injections, or erodible implants. A few non limiting examples are listed below for illustration.

For oral administration, the compounds may readily formulated by combining the disclosed liposomal compositions with pharmaceutically acceptable carriers known in the art. Such carriers enable formulation as for example, tablets, pills, dragees, capsules, liquids, gels, syrups, slurries, films, and suspensions for oral ingestion by a subject to be treated. Suitable excipients for include but are not limited to fillers such as sugars, including lactose, sucrose, mannitol, or sorbitol; cellulose preparations, such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). Optionally, the oral formulations are formulated in saline or buffers for neutralizing internal acid conditions or administered without carriers.

Pharmaceutical preparations that can be used orally include push-fit capsules made of gelatin, as well as soft, sealed capsules made of gelatin and a plasticizer, such as glycerol or sorbitol. The push-fit capsules can contain the liposomal composition suspended in suitable liquids, such as aqueous solutions, buffered solutions, fatty oils, liquid paraffin, or liquid polyethylene glycols. Stabilizers may also be added. All formulations for oral administration should be in dosages suitable for such administration.

For buccal administration, the compositions can take the form of tablets or lozenges formulated in a conventional manner.

For administration by inhalation, the compositions may be conveniently delivered in the form of an aerosol spray presentation from pressurized packs or a nebulizer, with the use of a suitable propellant, e.g., dichlorodifluoromethane, trichlorofluoromethane, ichlorotetrafluoroethane, carbon dioxide or other suitable gas. In the case of a pressurized aerosol, the dosage unit may be determined by providing a valve to deliver a metered amount.

The compositions may also be formulated in rectal or vaginal compositions such as suppositories or retention enemas, e.g., containing conventional suppository bases such as cocoa butter or other glycerides.

The example embodiments, contemplate administration of agents to subjects having or at risk of developing a cancer, including for example a solid tumor cancer, using the compositions and liposomes of example embodiments.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations of the disclosed compositions include without limitation aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include sodium chloride, Ringers injection, isotonic dextrose, sterile water, dextrose and lactated Ringers. Examples of nonaqueous parenteral vehicles include fixed oils of vegetable origin, cottonseed oil, corn oil, sesame oil and peanut oil. Antimicrobial agents in bacteriostatic or fungistatic concentrations are required to be added to parenteral preparations packaged in multiple-dose containers. Such antimicrobial agents include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include, without limitation, phosphate and citrate. Examples of antioxidants include for example sodium bisulfate. Exemplary local anesthetics include for example procaine hydrochloride. Suspending and dispersing agents include sodium carboxymethylcelluose, hydroxypropyl methylcellulose and polyvinylpyrrolidone. Emulsifying agents include for example, Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of a composition in an injectable formulation provided herein can routinely be adjusted such that an injection provides an effective amount to produce the desired pharmacological effect. The exact dose depends on the age, weight and condition of the patient or animal as is known or can routinely be determined by the skilled artisan.

The unit-dose parenteral preparations are packaged in an ampule, a vial or a syringe with a needle. All preparations for parenteral administration must be sterile, as is known and practiced in the art.

Illustratively, intravenous or intraarterial infusion of a sterile aqueous solution containing an active ingredient is an effective mode of administration. Another embodiment is a sterile aqueous or oily solution or suspension containing an active material injected as necessary to produce the desired pharmacological effect.

Injectables are designed for local and systemic administration. In one embodiment, an effective injectable dosage is formulated to contain a concentration of at least about 0.1% w/w up to about 90% w/w or more (preferably more than 1% w/w) of a compound provided herein to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is noted that the concentrations and dosage values may also vary with the age of the individual treated. It is further noted that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compositions provided herein may be suspended in micronized or other suitable form or may be derivatized to produce a more soluble active product or a prodrug. The form of the resulting mixture depends upon factors that include for example, the intended mode of administration and the solubility of a composition provided herein in the selected carrier or vehicle. The effective concentration is sufficient for ameliorating the symptoms of the condition and may be empirically determined.

The compositions provided herein also includes lyophilized powders, which can be reconstituted for administration as solutions, emulsions and other mixtures. The compositions can also be reconstituted and formulated as solids or gels. The lyophilized powder can be prepared for example, by dissolving the active ingredient, or a pharmaceutically acceptable derivative thereof, in a suitable solvent. The solvent may optionally contain an excipient which improves the stability or other pharmacological property of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those in the art, for maintain a desired pH (e.g., about neutral pH). Subsequent sterile filtration of the solution followed by lyophilization under standard conditions known in the art can routinely be applied to obtain the desired formulation. Generally, the resulting solution is apportioned into vials for lyophilization. In some embodiments, each vial contains a single dosage (10-500 mg, preferably 100-300 mg) or multiple dosages of a composition provided herein. The lyophilized powder can be stored under appropriate conditions know in the art (e.g., about 4° C. to room temperature). Reconstitution of the lyophilized powder with water for injection provides an exemplary, non-limiting formulation for use in parenteral administration. For reconstitution, about 1-50 mg, preferably 5-35 mg, more preferably about 9-30 mg of lyophilized powder, is added per mL of sterile water or other suitable carrier. The precise amount depends upon the selected compound. Such amount can be empirically determined using techniques known in the art.

EXAMPLES

Example 1: Liposomal Alpha Polyglutamated Pemetrexed Compositions

Methods:

Production of Polyglutamate-Cisplatin Complexes

To produce polyglutamate—Diammine dicarboxylic acid platinum (DDAP) Complex), an alpha hexaglutamate and Diammine dicarboxylic acid platinum (DDAP) was used. The process of complexation is dependent on the presence of Chlorinated platinum compound and pH conditions. The complexation is achieved by a nucleophilic attack on one or two carboxyl groups of glutamate by the platinate derivative. Briefly the complex was formed by the following procedure. First, the active compound DDAP was weighed and dissolved in 5% dextrose. After the DDAP dissolution step, aG6 is weighed out and added to the DDAP solution and allowed to stir for 1 hour at 37° C. The pH of the solution is adjusted to 6.5-7.0 using 1N NaOH and the solution was stirred overnight at 37° C. The formation of complex was confirmed visually. However when the pH was adjusted to acidic pH (3-4). The color reverted to its original. The formation of light brown color indicated the formation of the complex. This observation was confirmed using HPLC Data not shown.

Production of Pentaglutamated Pemetrexed-DDAP Complex (PGPD) Liposomes

Briefly PGPD is encapsulated in liposomes by the following procedure. First, the lipid components of the liposome membrane are weighed out and combined as a concentrated solution in ethanol at a temperature of around 65° C. In this example, the lipids used are hydrogenated soy phosphatidylcholine, cholesterol, and DSPE-PEG-2000 (1,2-distearoyl-sn-glycero-3-phosphoethanolamine-N-[methoxy(polyethylene glycol)-2000]). The molar ratio of HSPC: Cholesterol: PEG-DSPE is approximately 3:2:0.15. Next, PGPD is prepared as described in claim 0001 The PGPD drug solution is heated up to 65° C. The ethanolic lipid solution is injected into the PGPD solution using a small-bore needle. During this step the drug solution is well stirred using a magnetic stirrer. The mixing is performed at an elevated temperature (63° C.-72° C.) to ensure that the lipids are in the liquid crystalline state (as opposed to the gel state that they attain at temperatures below the lipid transition temperature Tm=51° C.-54° C.). As a result, the lipids are hydrated and form multiple bilayer (multilamellar) vesicles (MLV) containing PGPD in the aqueous core.

Downsizing of MLV's Using Filter Extrusion

The MLVs are fragmented into unilamellar (single bilayer) vesicles of the desired size by high-pressure extrusion using two passes through stacked (track-etched polycarbonate) membranes. The stacked membranes have two layers with a pore size of 200 nm and six layers with a pore size of 100 nm. During extrusion, the temperature is maintained above the Tm to ensure plasticity of the lipid membranes. Because of the extrusion, large and heterogeneous in size and lamellarity MLVs turn into small, homogenous (100-120 nm) unilamellar vesicles (ULV) that sequester the drug in their interior. A Malvern Zetasizer Nano ZS instrument (Southborough, MA) with back scattering detector (90°) was used for measuring the hydrodynamic size (diameter) at 25° C. in a quartz micro cuvette. The samples were diluted 50-fold in formulation matrix before analysis.

Purification of Liposomes

After the ULV's containing PGPD have been produced, the extra-liposomal PGPD is removed using columns for small volume or tangential flow diafiltration against a suitable buffer for large volume. Although any buffer solution can be used, in this example the buffer used is 5 mM HEPES, 145 mM Sodium Chloride, pH 6.7. Upon completion of purification, filter sterilization is performed using a 0.22-micron filter Production of Alpha Hexaglutamated Pemetrexed (αHgPMX) Liposomes The foregoing description of the specific embodiments, will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A liposome composition comprising a pegylated liposome encapsulating an ionically bound complex of a platinum-based chemotherapeutic agent or a salt thereof and polyglutamated antifolates having 4-10 glutamates linked by alpha or gamma carboxy group linkages, and one or more pharmaceutically acceptable carriers.

2. The liposome composition of claim 1, wherein the platinum-based chemotherapeutic agent is cisplatin or a cisplatin analog, or wherein the platinum-based chemotherapeutic agent is a member selected from the group: cisplatin, oxaliplatin, stratoplatin, paraplatin, platinol, cycloplatin, dexormaplatin, spiroplatin picoplatin, nedaplatin, triplatin, tetraplatin, lipoplatin, lobaplatin, ormaplatin, zeniplatin, platinum-triamine, traplatin, enloplatin, JIM-216, 254-S, NK 121, CI-973, DWA 2114R, NDDP, and dedaplatin.

3. The liposome composition of claim 1, wherein each liposome comprises between 100 to 100,000 ionically bound complexes formed by the platinum-based chemotherapeutic agent or salt thereof and the polyglutamated antifolates.

4. The liposome composition of claim 1, wherein the liposome has a diameter in the range of 20 nm to 200 nm or in the range of 80 nm to 120 nm.

5. The liposome composition of claim 1, wherein the polyethylene glycol of the liposome has a number average molecular weight (Mn) of 200 to 5000 daltons.

6. The liposome composition of claim 1, which comprises a steric stabilizer selected from the group consisting of poly-L-lysine (PLL); monosialoganglioside (GM1); poly(vinyl pyrrolidone) (PVP); poly(acrylamide) (PAA); poly(2-methyl-2-oxazoline); poly(2-ethyl-2-oxazoline); phosphatidyl polyglycerol; poly[N-(2-hydroxypropyl) methacrylamide]; amphiphilic poly-N-vinylpyrrolidones; L-amino-acid-based polymer; and polyvinyl alcohol.

7. The liposome composition of claim 1, wherein the liposome comprises at least one of an anionic lipid and a neutral lipid, or wherein the liposome comprises at least one is a member selected from the group: DSPE; DSPE-PEG-maleimide; DSPE-PEG-FITC; HSPC; HSPC-PEG; cholesterol; cholesterol-PEG; and cholesterol-maleimide.

8. The liposome composition of claim 1, wherein the liposome comprises oxidized phospholipids, optionally wherein the phospholipids are a member selected from the group consisting of phosphatidylserines, phosphatidylinositols, phosphatidylethanolamines, phosphatidylcholines and 1-palmytoyl-2-arachidonoyl-sn-glycero-2-phosphate.

9. The liposome composition of claim 1, wherein the liposome comprises oxidized 1-palmitoyl-2-arachidonoyl-sn-glycero-3-phosphorylchloine (OxPAPC), optionally wherein the oxPAPCs are epoxyisoprostane-containing phospholipids, or wherein the oxPAPC is 1-palmitoyl-2-(5,6-epoxyisoprostane E2)-sn-glycero-3-phosphocholine (5,6-PEIPC), 1-palmitoyl-2-(epoxy-cyclo-pentenone)-sn-glycero-3-phosphorylcholine (PECPC) and/or 1-palmitoyl-2-(epoxy-isoprostane E2)-sn-glycero-4-phosphocholine (PEIPC).

10. The liposome composition of claim 1, wherein the liposome is anionic or neutral, or wherein the liposome is cationic.

11. The liposome composition of claim 1, wherein the liposome has a zeta potential that is:
    (a) less than or equal to zero,
    (b) between 0 to −150 mV or between −30 to −50 mV,
    (c) greater than zero, or
    (d) between 1 and 100 mV, between 5 to 60 mV, or between 10 to 50 mV.

12. The liposome composition of claim 1, wherein the pH of the internal phase of the liposome is between 2.5 and 7.5.

13. The liposome composition of claim 1, which further comprises a targeting moiety attached to one or both of a PEG and the exterior of the liposome, and wherein the targeting moiety has a specific affinity for a surface antigen on a target cell of interest, optionally wherein the targeting moiety is attached to one or both of the PEG and the exterior of the liposome by a covalent bond herein.

14. The liposome composition of claim 13, wherein the targeting moiety is a polypeptide, optionally, wherein the targeting moiety is an antibody or a fragment of an antibody.

15. The liposome composition of claim 13, wherein the targeting moiety binds the surface antigen with an equilibrium dissociation constant (Kd) in a range of $0.5 \times 10^{-10}$ to $10 \times 10^{-6}$ as determined using surface plasmon resonance analysis.

16. The liposome composition of claim 13, wherein the targeting moiety specifically binds one or more folate receptors selected from the group: folate receptor alpha (FR-α), folate receptor beta (FR-β), and folate receptor delta (FR-δ).

17. The liposome composition of claim 13, wherein the targeting moiety comprises one or more members selected from the group: an antibody, a humanized antibody, an antigen binding fragment of an antibody, a single chain antibody, a single-domain antibody, a bi-specific antibody, a synthetic antibody, a pegylated antibody, and a multimeric antibody.

18. The liposome composition of claim 13, wherein each PEGylated liposome comprises from 30 to 500 targeting moieties or 30 to 200 targeting moieties.

19. The liposome composition of claim 13, wherein the liposome does not comprise a targeting moiety attached to one or both of a PEG and the exterior of the liposome.

20. The liposome composition of claim 1, which further comprises at least one cryoprotectant selected from the group consisting of mannitol; trehalose; sorbitol; and sucrose.

21. A method of killing a hyperproliferative cell comprising contacting a hyperproliferative cell with the liposome composition of claim 1, optionally wherein the hyperproliferative cell is a cancer cell.

22. A method for treating or preventing disease in a subject needing such treatment or prevention, the method comprising administering an effective amount of the liposome composition of claim 1 to a subject in need thereof, optionally wherein the disease is cancer and the subject has or at risk of having cancer.

23. The method of claim 22, wherein the cancer is a member selected from the group: lung cancer, pancreatic cancer, breast cancer, ovarian cancer, prostate cancer, head and neck cancer, gastric cancer, gastrointestinal cancer, colorectal cancer, esophageal cancer, cervical cancer, liver cancer, kidney cancer, biliary duct cancer, gallbladder cancer, bladder cancer, sarcoma (e.g., osteosarcoma), brain cancer, central nervous system cancer, and melanoma; and a hematologic malignancy such as for example, a leukemia, a lymphoma and other B cell malignancies, myeloma and other plasma cell dyscrasias.

24. A method of delivering a liposome composition to a tumor expressing an antigen on its surface, the method comprising: administering the liposome composition of claim 13 to a subject having a tumor expressing the antigen bound by the liposome targeting moiety in an amount to deliver a therapeutically effective dose of the liposome composition to the tumor, optionally wherein the administration is parenteral or intravenous.

25. A method for treating cancer that comprises administering an effective amount of the liposome composition of claim 13 to a subject having or at risk of having a cancer cell that expresses on its surface the antigen bound by the liposome targeting moiety, optionally wherein the administration is parenteral or intravenous.

26. A maintenance therapy that comprises administering an effective amount of the liposome composition of claim 1 to a subject that is undergoing or has undergone cancer therapy, optionally wherein the administration is parenteral or intravenous.

27. A pharmaceutical composition comprising the liposome composition of claim 1.

28. The liposome composition of claim 1, wherein the polyglutamated antifolate is a member selected from the group: polyglutamated methotrexate (MTX), polyglutamated pemetrexed (PMX), polyglutamated lometrexol (LTX), polyglutamated AG2034, polyglutamated raltitrexed (RTX), polyglutamated piritrexim, polyglutamated pralatrexate, polyglutamated AG2034, polyglutamated GW 1843, polyglutamated aminopterin, and polyglutamated LY309887.

29. The liposome composition of claim 1, wherein the polyglutamated antifolate contains 4-6 glutamates linked by carboxyl group linkages.

30. The liposome composition of claim 28, wherein the polyglutamated antifolate contains 4-6 glutamates linked by carboxyl group linkages.

* * * * *